US010676511B2

(12) United States Patent
Gershoni et al.

(10) Patent No.: US 10,676,511 B2
(45) Date of Patent: Jun. 9, 2020

(54) CORONAVIRUSES EPITOPE-BASED VACCINES

(71) Applicant: RAMOT AT TEL-AVIV UNIVERSITY LTD., Tel Aviv (IL)

(72) Inventors: Jonathan Gershoni, Herzliya (IL); Natalia T. Freund, Savyon (IL)

(73) Assignee: RAMOT AT TEL-AVIV UNIVERSITY LTD., Tel Aviv (IL)

(*) Notice: Subject to any disclaimer, the term of this patent is extended or adjusted under 35 U.S.C. 154(b) by 0 days.

(21) Appl. No.: 15/760,878

(22) PCT Filed: Sep. 15, 2016

(86) PCT No.: PCT/IL2016/051029

§ 371 (c)(1),
(2) Date: Mar. 16, 2018

(87) PCT Pub. No.: WO2017/046801

PCT Pub. Date: Mar. 23, 2017

(65) Prior Publication Data

US 2018/0334480 A1 Nov. 22, 2018

Related U.S. Application Data

(60) Provisional application No. 62/219,926, filed on Sep. 17, 2015.

(51) Int. Cl.

*C07K 14/005* (2006.01)
*A61K 39/215* (2006.01)
*A61K 39/12* (2006.01)
*A61P 31/14* (2006.01)

(52) U.S. Cl.

CPC ............ *C07K 14/005* (2013.01); *A61K 39/12* (2013.01); *A61K 39/215* (2013.01); *A61P 31/14* (2018.01); *C07K 2319/735* (2013.01); *C12N 2770/20022* (2013.01); *C12N 2770/20034* (2013.01); *C12N 2770/20051* (2013.01)

(58) Field of Classification Search

CPC ........... C12N 2770/20022; C12N 2770/20034; C12N 7/00; C12N 2770/20021; C12N 15/86; C12N 2770/20011; C12N 2770/20043; C12N 2770/20023; C12N 2770/20033; C12N 2770/20051; C12N 2770/20071; C12N 2770/20032; C12N 2770/20045; C07K 14/005; C07K 16/10; C07K 14/165; C07K 2319/735; A61K 39/12; A61K 39/215; A61P 31/14

See application file for complete search history.

(56) References Cited

FOREIGN PATENT DOCUMENTS

WO 2014/134439 A1 9/2014

OTHER PUBLICATIONS

Wu RP, Meng JZ, He YX. [Construction and screening of SARS-CoV S protein-specific phage displayed antifen libary]. Bing Du Xue Bao. May 2013;29(3):280-6. Chinese. PubMed PMID: 23905471.*

Du L, Zhao G, Kou Z, Ma C, Sun S, Poon VK, Lu L, Wang L, Debnath AK, Zheng BJ, Zhou Y, Jiang S. Identification of a receptor-binding domain in the S protein of the novel human coronavirus Middle East respiratory syndrome coronavirus as an essential target for vaccine development. J Virol. Sep. 2013;87(17):9939-42.*

Zhong X, Qi G, Yang J, Xing G, Liu J, Yang X. [High-efficiency expression of a receptor-binding domain of SARS-CoV spike protein in tobacco chloroplasts]. Sheng Wu Gong Cheng Xue Bao. Jun. 2014;30(6):920-30. Chinese. PubMed PMID: 25212009.*

Sjöberg M, Lindqvist B, Garoff H. Activation of the alphavirus spike protein is suppressed by bound E3. J Virol. Jun. 2011;85(11): 5644-50. Epub Mar. 23, 2011.*

“Juxtapose.” www.merriam-webster.com. Accessed Jul. 10, 2019.*

Bailey et al., “Meme Suite: tools for motif discovery and searching”, Nucleic Acids Research, (2009), vol. 31, web server issue, pp. W202-W208.

Bublil et al., “Computational prediction of the cross-reactive neutralizing epitope corresponding to the monoclonal antibody b12 specific for HIV-1 gp120”, FASEB J., (2006), vol. 20, pp. 1762-1774.

Bublil et al., “Stepwise Prediction of Conformational Discontinuous B-Cell Epitopes Using the Mapitope Algorithm”, Proteins: Structure, Function, and Bioinformatics, (2007), vol. 68, pp. 294-304.

Chang et al, “Cell adhesion as a novel approach to determining the cellular binding motif on the severe acute respiratory syndrome coronavirus spike protein”, Journal of Virological Methods, (2014), vol. 201, pp. 1-6.

Chen et al., “Crystal Structure of the Receptor-Binding Domain from Newly Emerged Middle East Respiratory Syndrome Coronavirus”, Journal of Virology, (2013), vol. 87, No. 19, pp. 10777-10783.

Coughlin et al., “Neutralizing Human Monoclonal Antibodies to Severe Acute Respiratory Syndrome Coronavirus: Target, Mechanism of Action and Therapeutic Potential”, Rev Med Virol., (2012), vol. 22, No. 1, pp. 2-17.

Du et al, “A Truncated Receptor-Binding Domain of MERS-CoV Spike Protein Potently Inhibits MERS-CoV Infection and Induces Strong Neutralizing Antibody Responses: Implication for Developing Therapeutics and Vaccines”, PLoS ONE, (2013), vol. 8, issue 12, p. e81587 (9 pages).

(Continued)

*Primary Examiner* — Rachel B Gill

(74) *Attorney, Agent, or Firm* — Vorys, Sater, Seymour and Pease LLP; Anthony Venturino

(57) ABSTRACT

Provided are polypeptides derived from the coronaviruses (CoVs) Spike protein (S) characterized by high affinity and specificity the S receptor and its neutralizing antibodies. Further provided are compositions and vaccines, and vaccine-based therapies targeting CoVs, and SARS and MERS viruses in particular.

20 Claims, 19 Drawing Sheets
(16 of 19 Drawing Sheet(s) Filed in Color)
Specification includes a Sequence Listing.

(56) References Cited

OTHER PUBLICATIONS

Du et al., "Recombinant receptor-binding domain of SARS-CoV spike protein expressed in mammalian, insect and *E. coli* cells elicits potent neutralizing antibody and protective immunity", Virology, (2009), vol. 393, pp. 144-150.
Du et al., "A Conformation-Dependent Neutralizing Monoclonal Antibody Specifically Targeting Receptor-Binding Domain in Middle East Respiratory Syndrome Coronavirus Spike Protein", Journal of Virology, (2014), vol. 88, No. 12, pp. 7045-7053.
Enshell-Seuffers et al., "The rational design of a 'type 88' genetically stable peptide display vector in the filamentous bacteriophage fd", Nucleic Acids Research, (2001), vol. 29, No. 10, 13 pages.
Freund et al., "Phage Display Selection, Analysis, and Prediction of B Cell Epitopes", Curr. Protoc. Immunol., (2009), vol. 86, pp. 9.8.1-9.8.30.
Freund et al., "Reconstitution of the receptor-binding motif of the SARS coronavirus", Protein Engineering, Design & Selection, (2015), pp. 1-9.
Gershoni et al., "Epitope Mapping: The First Step in Developing Epitope-Based Vaccines", Biodrugs, (2007), vol. 21, No. 3, pp. 145-156.
Ho et al., "Design and biological activities of novel inhibitory peptides for SARS-CoV spike protein and angiotensin-converting enzyme 2 interaction", Antiviral Research, (2006), vol. 69, pp. 70-76.
Hu et al., "Screening and Identification of Linear B-Cell Epitopes and Entry-Blocking Peptide of Severe Acute Respiratory Syndrome (SARS)-Associated Coronavirus Using Synthetic Overlapping Peptide Library", J. Comb. Chem., (2005), vol. 7, pp. 648-656.
Hwang et al., "Structural Basis of Neutralization by a Human Anti-severe Acute Respiratory Syndrome Spike Protein Antibody, 80R", The Journal of Biological Chemistry, (22006), vol. 281, No. 45, pp. 34610-34616.
Kaplan et al., "A general insert label for peptide display on chimeric filamentous bacteriophages", Analytical Biochemistry, (2012), vol. 420, pp. 68-72.
Lin et al., "Generating Stable Chinese Hamster Ovary Cell Clones to Produce a Truncated SARS-CoV Spike Protein or Vaccine Development", Biotechnol. Prog., (2010), vol. 26, pp. 1733-1740.
Ma et al., "Searching for an ideal vaccine candidate among different MERS coronavirus receptor-binding fragments—the importance of immunofocusing in subunit vaccine design", Vaccine, (2014), vol. 32, No. 46, pp. 6170-6176.
Marra et al, "The Genome Sequence of the SARS-Associated Coronavirus", Science, (2003), vol. 300, No. 5624, pp. 1399-1404.
Mayrose et al., "Pepitope: epitope mapping from affinity-selected peptides", Bioinformatics, (2007), vol. 23, No. 23, pp. 3244-3246.
Mayrose et al., "Epitope mapping using combinatorial phage-display libraries: a graph-based algorithm", Nucleic Acids Research, (2007), vol. 35, No. 1, pp. 69-78.
Rota et al., "Characterization of a Novel Coronavirus Associated with Severe Acute Respiratory Syndrome", Science, vol. 300, No. 5624, p. s1394-1399.
Rubinstein et al., "Computational characterization of B-cell epitopes", Molecular Immunology, (2008), vol. 45, pp. 3477-3489.
Ryvkin et al., "Deep Panning: Steps towards Probing the IgOme", PLoS ONE, (2012), vol. 7, No. 8, p. e41469 11 pages.
Siman-Tov et al., "The use of epitope arrays in immunodiagnosis of infectious disease: Hepatitis C virus, a case study", Analytical Biochemistry, (2013), vol. 432, pp. 63-70.
Smith et al., "Single-step purification of polypeptides expressed in *Escherichia coli* as fusions with glutathione S-transferase", Gene, (1988), vol. 67, pp. 31-40.
Struck et al., "A hexapeptide of the receptor-binding domain of SARS corona virus spike protein blocks viral entry into host cells via the human receptor ACE2", Antiviral Research, (2012), vol. 94, pp. 288-296.
Sui et al., "Potent neutralization of severe acute respiratory syndrome (SARS) coronavirus by a human mAb to S1 protein that blocks receptor association", PNAS, (2004), vol. 101, No. 8, pp. 2536-2541.
Tang et al., "Identification of human neutralizing antibodies against MERS-CoV and their role in virus adaptive evolution", PNAS, (2014), pp. E2018-E2026.
Tarnovitski et al., "Mapping a Neutralizing Epitope on the SARS Coronavirus Spike Protein: Computational Prediction Based on Affinity-selected Peptides", J. Mol. Biol., (2006), vol. 359, pp. 190-201.
Weiss-Ottolenghi et al., "Profiling the IgOme: Meeting the challenge", FEBS Letters, (2014), vol. 588, pp. 318-325.
Wong et al., "A 193-Amino Acid Fragment of the SARS Coronavirus S Protein Efficiently Binds Angiotensin-converting Enzyme 2", The Journal of Biological Chemistry, (2004), vol. 279, No. 5, pp. 3197-3201.
Xiao et al., "The SARS-CoV S glycoprotein: expression and functional characterization", Biochemical and Biophysical Research Communications, (2003), vol. 312, pp. 1159-1164.
Yeager et al., "Human aminopeptidase N is a receptor for human coronavirus 229E", Nature, (1992), vol. 357, pp. 420-422.
Ying et al., "Exceptionally Potent Neutralization of Middle East Respiratory Syndrome Coronavirus by Human Monoclonal Antibodies", Journal of Virology, (2014), vol. 88, No. 14, pp. 7796-7805.
Ying et al., "Junctional and allele-specific residues are critical for MERS-CoV neutralization by an exceptionally potent germline-like antibody", Nature Communications, (2015), vol. 6, No. 8223, pp. 1-10.
Yu et al., "Structural basis for the neutralization of MERS-CoV by a human monoclonal antibody MERS-27", Scientific Reports, (2015), vol. 5, No. 13133, pp. 1-11.
Yuan et al., "GenBank Accession: AAR86788.1, spike [SARS coronavirus ShanghaiQXC1]", (2004), one page.
Yuan et al., "GenBank Accession: AY463056.1, SARS coronavirus ShanghaiQXC1, complete genome", (2004), nine pages.
Zhu et al., "Potent cross-reactive neutralization of SARS coronavirus isolates by human monoclonal antibodies", PNAS, (2007), vol. 104, No. 29, pp. 12123-12128.

* cited by examiner

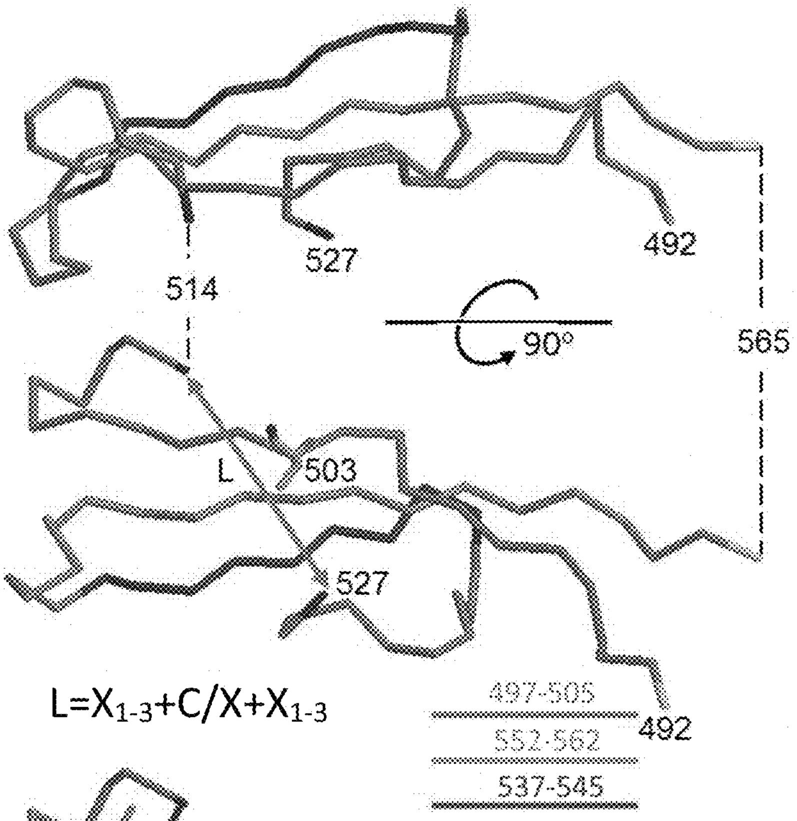
Fig. 9B
Fig. 9C
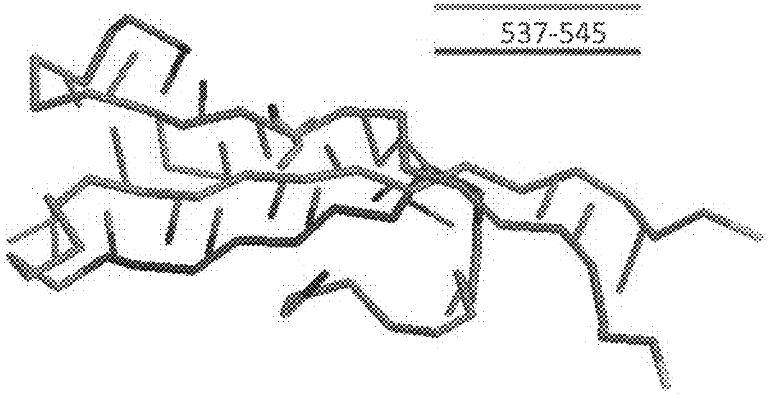
Fig. 9D
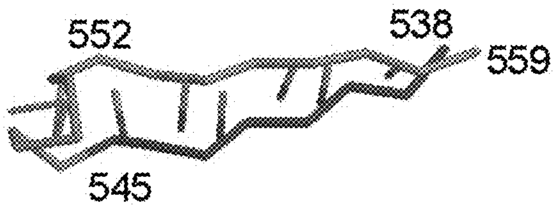
Fig. 9E

Fig. 11B
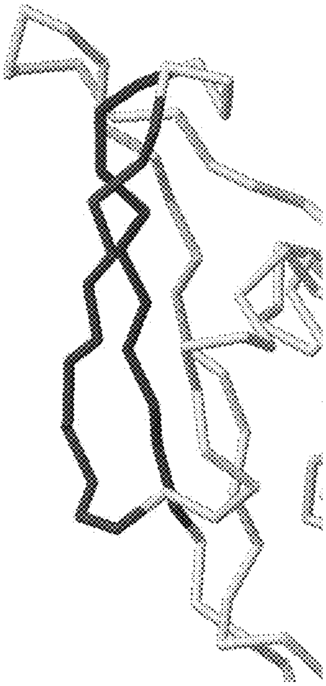
Fig. 11C
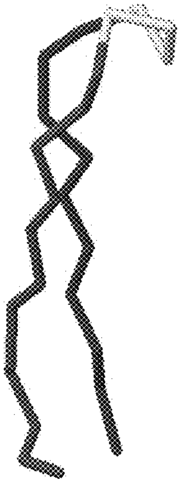
Fig. 11D
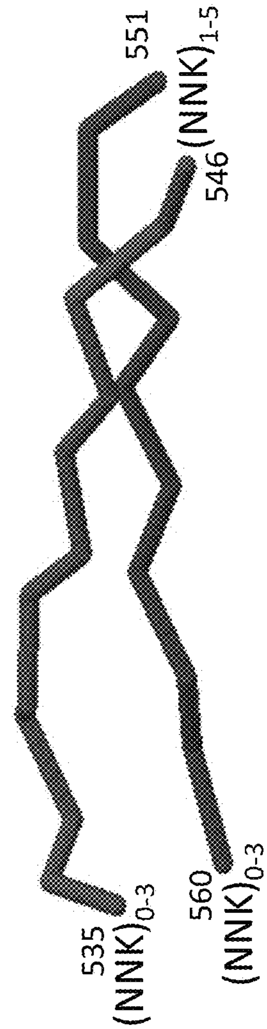
Fig. 11E
$(NNK)_{0-3}$ W E D G D Y Y R K Q L S $(NNK)_{1-5}$ G G W L V A S G S T $(NNK)_{0-3}$

CORONAVIRUSES EPITOPE-BASED VACCINES

SEQUENCE LISTING

The Sequence Listing submitted in text format (.txt) filed on Aug. 7, 2018, named "SequenceListing.txt", created on Jul. 5, 2018 (75.3 KB), is incorporated herein by reference.

FIELD OF THE INVENTION

The present invention relates to the field of vaccines, specifically vaccines targeted at coronaviruses (CoVs). More specifically, the present invention provides CoV epitope-based polypeptides.

BACKGROUND OF THE INVENTION

The outbreak of the Severe Acute Respiratory Syndrome (SARS) epidemic in year 2002 motivated an international WHO-coordinated collaborative effort to discover the etiologic agent of this emerging disease. By March 2003 this effort culminated with the discovery and cloning of the SARS coronavirus (SARS CoV) (Marra et al. 2003; Rota et al. 2003) and within the same year its cellular receptor, Angiotensin-Converting Enzyme 2 (ACE2) was identified (W. Li et al. 2003). The extracellular aspect of S protein can further be divided into two functional sub-domains; 51 responsible for receptor recognition (amino acids 13-666) and S2 (amino acids 667-1195) which in response to 51 binding to ACE2, undergoes conformational rearrangements that enable viral fusion with the target-cell membrane (Du et al. 2009).

In general, in all CoVs, the Receptor Binding Domain (RBD) can be located within the first few hundred amino acid residues of 51, or further downstream (e.g., as in human coronavirus 229E. The RBD of SARS CoV was identified as a minimal 193-amino acid long sequence starting around residue N318. However, efforts to produce smaller independently-folding, functional receptor-binding peptides of 51 were unsuccessful. The co-crystallization of the RBD bound to its receptor ACE2, revealed that the actual binding interface lies within an extended excursion juxtaposed along the edge of the core of the RBD and constitutes the Receptor Binding Motif (RBM, residues S432-T486) (F. Li et al. 2005).

Several studies demonstrated anti-SARS human antibodies that target the SARS CoV RBM, reviewed in (Coughlin and Prabhakar 2012)). One such antibody is the human monoclonal antibody (mAb) 80R, which neutralizes SARS CoV in vitro and in vivo (Sui et al. 2004). The epitope of mAb 80R overlaps extensively with the binding surface recognized by ACE2, as is shown in the crystal structure of 80R:RBD and by competition studies for binding to S1 domain (Sui et al. 2004). Co-crystallization of mAb 80R with the RBD reveals that 9 of the 23 contact residues contained within the RBM coincide precisely with those that mediate ACE2 binding (Hwang et al. 2006), illustrating the prominence of the RBM as a bi-functional bioactive surface.

More recently, the MERS epidemic caused by the Middle East Respiratory Syndrome CoV (MERS, or EMC/2012), is an emerging public health hazard. The etiologic agent of MERS is also a CoV, this member is carried by bats and infects camels who directly or indirectly transmit it to humans. Thus far a few thousand individuals have been infected in the Middle East, Korea, Hong Kong. MERS, like SARS, causes severe respiratory track disease however with a markedly higher (>40%) mortality rate.

While considerable efforts are being made in attempt to produce prophylactic vaccines for SARS and more recently for MERS, there is currently no effective vaccine for any of these viruses. Hence there is a genuine need for an effective prophylactic CoVs vaccine. The present invention addresses this need.

BACKGROUND REFERENCES

Bailey, T. L., et al. (2009), 'MEME SUITE: tools for motif discovery and searching', *Nucleic Acids Res,* 37 (Web Server issue), W202-8.

Bublil, E. M., Yeger-Azuz, S., and Gershoni, J. M. (2006), 'Computational prediction of the cross-reactive neutralizing epitope corresponding to the monclonal antibody b12 specific for HIV-1 gp120', *FASEB J,* 20 (11), 1762-74.

Bublil, E. M., et al. (2007), 'Stepwise prediction of conformational discontinuous B-cell epitopes using the Mapitope algorithm', *Proteins,* 68 (1), 294-304.

Chang, H. H., et al. (2014), 'Cell adhesion as a novel approach to determining the cellular binding motif on the severe acute respiratory syndrome coronavirus spike protein', *J Virol Methods,* 201, 1-6.

Chen, Y., et al. (2013) 'Crystal structure of the receptor-binding domain from newly emerged Middle East respiratory syndrome coronavirus', *J Virol.* 87:10777-83.

Coughlin, M. M. and Prabhakar, B. S. (2012), 'Neutralizing human monoclonal antibodies to severe acute respiratory syndrome coronavirus: target, mechanism of action, and therapeutic potential', *Rev Med Virol,* 22 (1), 2-17.

Du, L., et al. (2014), 'A conformation-dependent neutralizing monoclonal antibody specifically targeting receptor-binding domain in Middle East respiratory syndrome coronavirus spike protein', *J Virol* 88:7045-53.

Enshell-Seijffers, D., Smelyanski, L., and Gershoni, J. M. (2001), 'The rational design of a 'type 88' genetically stable peptide display vector in the filamentous bacteriophage fd', *Nucleic Acids Res,* 29 (10), E50-0.

Freund, N. T., Enshell-Seijffers, D., and Gershoni, J. M. (2009), 'Phage display selection, analysis, and prediction of B cell epitopes', *Curr Protoc Immunol, Chapter* 9 (86), 9.8.1-9.8.30.

Freund, N. T., et al. (2015), 'Reconstitution of the receptor-binding motif of the SARS coronavirus', *Protein Eng Des Sel.* Gershoni, J. M., et al. (2007), 'Epitope mapping: the first step in developing epitope-based vaccines', BioDrugs, 21 (3), 145-56.

Ho, T. Y., et al. (2006), 'Design and biological activities of novel inhibitory peptides for SARS-CoV spike protein and angiotensin-converting enzyme 2 interaction', *Antiviral Res,* 69 (2), 70-6.

Hu, H., et al. (2005), 'Screening and identification of linear B-cell epitopes and entry-blocking peptide of severe acute respiratory syndrome (SARS)-associated coronavirus using synthetic overlapping peptide library', *J Comb Chem,* 7 (5), 648-56.

Hwang, W. C., et al. (2006), 'Structural basis of neutralization by a human anti-severe acute respiratory syndrome spike protein antibody, 80R', *J Biol Chem,* 281 (45), 34610-6.

Kaplan, G. and Gershoni, J. M. (2012), 'A general insert label for peptide display on chimeric filamentous bacteriophages', *Anal Biochem,* 420 (1), 68-72.

Ma, C. L., et al. (2014), 'Searching for an ideal vaccine candidate among different MERS coronavirus receptor-binding fragments—the importance of immunofocusing in subunit vaccine design', *Vaccine* 32:6170-6.

Marra, M. A., et al. (2003), 'The Genome sequence of the SARS-associated coronavirus', *Science,* 300 (5624), 1399-404.

Mayrose, I., et al. (2007a), 'Epitope mapping using combinatorial phage-display libraries: a graph-based algorithm', *Nucleic Acids Res,* 35 (1), 69-78.

Mayrose, I., et al. (2007b), 'Pepitope: epitope mapping from affinity-selected peptides', *Bioinformatics,* 23 (23), 3244-6.

Rota, P. A., et al. (2003), 'Characterization of a novel coronavirus associated with severe acute respiratory syndrome', *Science,* 300 (5624), 1394-9.

Rubinstein, N. D., et al. (2008), 'Computational characterization of B-cell epitopes', *Mol Immunol,* 45 (12), 3477-89.

Ryvkin, A. H. et al. (2012), 'Deep Panning: steps towards probing the IgOme', *PLoS One* 7:e41469.

Siman-Tov, D. D., et al. (2013), 'The use of epitope arrays in immunodiagnosis of infectious disease: hepatitis C virus, a case study', *Anal Biochem,* 432 (2), 63-70.

Smith, D. B., and K. S. Johnson. (1988), 'Single-step purification of polypeptides expressed in *Escherichia coli* as fusions with glutathione S-transferase', *Gene* 67:31-40.

Struck, A. W., et al. (2012), 'A hexapeptide of the receptor-binding domain of SARS corona virus spike protein blocks viral entry into host cells via the human receptor ACE2', *Antiviral Res,* 94 (3), 288-96.

Sui, J., et al. (2004), 'Potent neutralization of severe acute respiratory syndrome (SARS) coronavirus by a human mAb to 51 protein that blocks receptor association', *Proc Natl Acad Sci USA,* 101 (8), 2536-41.

Tang, X. C., et al. (2014), 'Identification of human neutralizing antibodies against MERS-CoV and their role in virus adaptive evolution', *Proc Natl Acad Sci USA* 111: E2018-26.

Tarnovitski, N., et al. (2006), 'Mapping a neutralizing epitope on the SARS coronavirus spike protein: computational prediction based on affinity-selected peptides', *J Mol Biol,* 359 (1), 190-201.

Weiss-Ottolenghi, Y., and J. M. Gershoni. (2013), 'Profiling the IgOme: Meeting the challenge', *FEBS Lett.*

Wong, S. K., et al. (2004), 'A 193-amino acid fragment of the SARS coronavirus S protein efficiently binds angiotensin-converting enzyme 2', *J Biol Chem,* 279 (5), 3197-201.

Xiao, X., et al. (2003), 'The SARS-CoV S glycoprotein: expression and functional characterization', *Biochem Biophys Res Commun,* 312 (4), 1159-64.

Yeager, C. L., et al. (1992), 'Human aminopeptidase N is a receptor for human coronavirus 229E', *Nature,* 357 (6377), 420-2.

Ying, T., et al. (2014) 'Exceptionally potent neutralization of Middle East respiratory syndrome coronavirus by human monoclonal antibodies' *J Virol* 88:7796-805.

Ying, T., et al. (2015), 'Junctional and allele-specific residues are critical for MERS-CoV neutralization by an exceptionally potent germline-like antibody', *Nature* Communications, 6:8223, 1-10.

Yu, X., et al. (2015), 'Structural basis for the neutralization of MERS-CoV by a human monoclonal antibody MERS-27', *Sci Rep* 5:13133.

Zhu, Z., et al. (2007), 'Potent cross-reactive neutralization of SARS coronavirus isolates by human monoclonal antibodies', *Proc Natl Acad Sci USA,* 104 (29), 12123-8.

SUMMARY OF THE INVENTION

According to one aspect, the invention relates to a polypeptide comprising an amino acid sequence of at least one reconstituted Receptor Binding Motif (RBM) of viral Spike protein, specifically, Coronavirus (CoV) spike protein, or any fragments thereof. More specifically, the reconstituted RBM of the invention may comprise at least one linker and at least one fragment of the native RBM. In some specific embodiments, the native RBM is a 30 to 200 amino acid sequence comprised within the Receptor Binding Domain (RBD) of said Spike protein forming a binding interface that interacts with the viral receptor. In some specific embodiments, the native RBM is an extended 30 to 100 or more amino acid excursion, juxtaposed along the edge of the core of the RBD and tacked to the core via a tacking segment. In some specific embodiments, the reconstituted RBM may comprise at least one linker, specifically, exogenous linker. In more specific embodiments, at least one of said linker/s may replace or is added to at least one of: the tacking segment, any part or amino acid residue/s thereof, and any RBM fragment/s or amino acid residue/s thereof. In some embodiments, the linker/s may replace at least one amino acid residues not directly involved or participate in receptor and/or neutralizing antibodies (nAb/s) binding. In yet some further embodiments, the linker/s may replace at least one amino acid residue involved directly or indirectly involved in receptor and/or nAb/s biding.

In yet a second aspect, the invention relates to a composition comprising an effective amount of at least one polypeptide comprising an amino acid sequence of at least one reconstituted RBM of CoV Spike protein or of any fragment thereof, any derivative, enantiomer, fusion protein, conjugate or polyvalent dendrimer thereof, as defined by the invention. The composition of the invention may optionally further comprise at least one pharmaceutically acceptable carrier/s, excipient/s, auxiliaries, and/or diluent/s.

A third aspect of the invention relates to an epitope based CoV vaccine comprising at least one polypeptide comprising at least one reconstituted RBM of CoV Spike protein or of any fragment thereof, any derivative, enantiomer, fusion protein, conjugate or polyvalent dendrimer thereof, as defined by the invention. In more specific embodiments, the vaccine of the invention may optionally further comprise at least one pharmaceutically acceptable carrier/s, excipient/s, auxiliaries, and/or diluent/s.

A further aspect of the invention provides a method for preventing, inhibiting, reducing, eliminating, protecting or delaying the onset of an infection or infectious clinical condition caused by coronavirus in a subject in need thereof. More specifically, the method comprising the step of administrating to the subject an effective amount of at least one polypeptide comprising an amino acid sequence of at least one reconstituted RBM of CoV Spike protein or of any fragment thereof, any derivative, enantiomer, fusion protein, conjugate or polyvalent dendrimer thereof, or of any composition or vaccine comprising the same.

The invention further provides the use of the reconstituted RBM polypeptide as defined by the invention in the preparation of an epitope based CoV vaccine for inducing an immune response against a coronavirus in a subject in need thereof.

A further aspect of the invention relates to an isolated polypeptide as defined by the invention, for use in a method of inducing an immune response against a coronavirus in a subject in need thereof.

In yet a further aspect, the invention provides a method for the preparation of a functional reconstituted RBM of a viral Spike protein, said method comprises the step of: (a) providing/constructing a conformer library of RBMs of said viral Spike protein, comprising plurality of bacteriophages, each expressing a reconstituted RBM comprising an amino acid sequence of at least one fragment of an RBM of a viral Spike protein and at least one exogenous combinatorial linker; (b) screening said library with a binding molecule; and (c) identifying and producing reconstituted RBM peptides which bind at least one of said binding molecules.

Still further, the invention relates to a method for producing epitope based CoV vaccine comprising reconstituted RBM. More specifically, the method comprising the step of preparing reconstituted functional RBM/s of a CoV Spike protein by a method as defined by the invention; and (b) admixing at least one of said reconstituted functional RBM/s of a CoV Spike protein or any derivative or enantiomer thereof, or any fusion protein, conjugate, or polyvalent dendrimer comprising the same with at least one adjuvant/s, carrier/s, excipient/s, auxiliaries, and/or diluent/s. These and other aspects of the invention will become apparent by the hand of the following drawings.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A is a backbone representation of the SARS CoV RBD taken from the RBD/80R co-crystal (PDBID: 2GHW, residues I319-T509 (SEQ ID NO: 26), the mAb 80R is not shown). A series of three alpha helices ($\alpha$1-$\alpha$3, blue) and a looped structure (residues N393-F416 (SEQ ID NO: 84), red) flank either side of the central anti-parallel beta sheet ($\beta$1-$\beta$4+$\beta$7). See text for further details.

FIG. 1B is an alternative view of RBD residues I319-A430 (denoted by SEQ ID NO: 28) rotated approximately 90 degrees relative to FIG. 1A to provide an alternative view of $\alpha$1-$\alpha$3 (blue) bordering the compact central core structure.

FIG. 1C is a detailed presentation of the five beta strands ($\beta$1-$\beta$4+$\beta$7) interconnected by a network of hydrogen bonds.

FIG. 2A shows the RBD region, L421 through S500 (also denoted by SEQ ID NO: 1), containing a total of 29 residues that contact mAb 80R (red and blue), 16 of which are exclusive to mAb 80R (red) and additional 13 residues are shared by mAb 80R and ACE2 (blue). Residues of the 16-amino acid loop of the RBM (R444-P459, also denoted by SEQ ID NO:2) are highlighted in green. The amino acids of the RBM region (5432-T486, also denoted by SEQ ID NO: 3) used in the present EXAMPLES are highlighted (light green). A total of 9 tyrosine residues are shown (marked with an asterisk), six of which are direct contact residues for both ACE2 and mAb 80R.

FIG. 2B is a backbone representation of the interaction between a single extended alpha helix of the ACE2 (PDBID: 2AJF; Q24-L45, light blue) and 8 residues located within the RBM region (the RBM region contains residues Y436-T486, also denoted by SEQ ID NO: 4, in grey).

FIG. 2C is a representation of the interaction between 80R mAb and 28 residues located within the RBM (PDBID: 2GHW; the RBM region used herein comprises residues 5432-T486SEQ ID NO: 3, in grey) involving a series of 7 discontinuous antibody segments (colored separately). In FIGS. 2B-2C, the 16-amino acid loop is colored green.

FIG. 4A illustrates the SARS-CoV Receptor Binding Domain (RBD, residues 323-502 of the SARS CoV 51 protein, denoted by SEQ ID NO: 85. The Receptor Binding Motif (RBM, residues 432-486, denoted by SEQ ID NO: 3, orange) sits juxtaposed along the core of the RBD. The loop 443-458, denoted by SEQ ID NO: 7 (blue) functions to tack the RBM to the core.

FIG. 4B shows the RBM area from which the above core and loop were deleted. Two discontinuous peptides are shown (432-443 and 460-486 denoted by SEQ ID NO: 5 and SEQ ID NO: 6, respectively) and a 7 Å gap between them (namely between residues 444 and 459, SEQ ID NO: 2).

FIG. 4C and FIG. 4D are a graphic representation of the sequences of linkers which were affinity selected using mAb 80R from $NNK_3$, and $NNK_4$ RBM "Conformer Libraries" and were used as input for the MEME Suite motif analysis software (Bailey et al. 2009)). The MEME logos illustrate the amino acid distribution in the affinity-selected linkers.

FIG. 4E shows ELISA of the binding of affinity-selected phages to mAb 80R. The overall expression of RBM peptides in each case is measured using the GIL-Ab reagent (Kaplan and Gershoni 2012), wild type phage fth-1 was used as a negative control (S.D. is shown as error bars). Amino acid sequences of the different linkers are GEM; EEP; GDPM (denoted by SEQ ID NO: 9); GDPN (denoted by SEQ ID NO: 10); GEVD (denoted by SEQ ID NO: 11); and GEPL (denoted by SEQ ID NO: 12).

Figure shows ELISA of the binding of wild-type GEM465K and EEP465K phages to mAb 80R compared to that of affinity-selected GEM and EEP in which lysine 465 spontaneously mutated to isoleucine (lysine 465 erfers to position 465 in the SARS-CoV 51 protein as denoted by SEQ ID NO: 31). The overall expression of RBM peptides in each case is measured using the GIL-Ab reagent, wild type phage fth-1 was used as a negative control (S.D. is shown as error bars).

Figure 6:
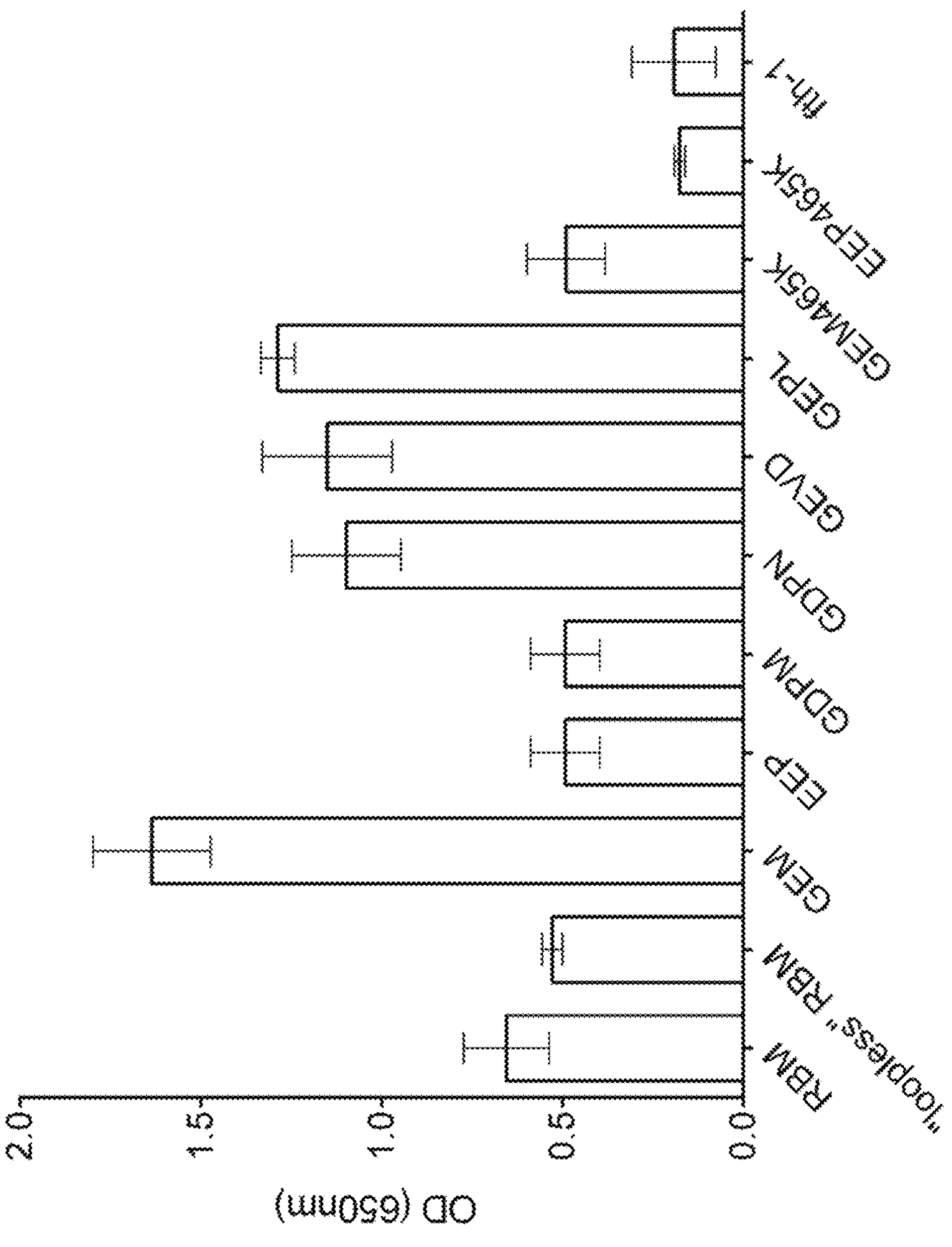

FIG. 6. Binding of mAb 80R affinity-selected phages to the ACE2 receptor

Figure shows ELISA of the binding of immobilized human ACE2 protein to affinity-selected phages. Binding of phages to the ACE2 protein was detected using polyclonal rabbit antibodies specific to M13. (S.D. is shown as error bars). Amino acid sequences of the linkers are as disclosed herein above in FIG. 4.

Figure 7:
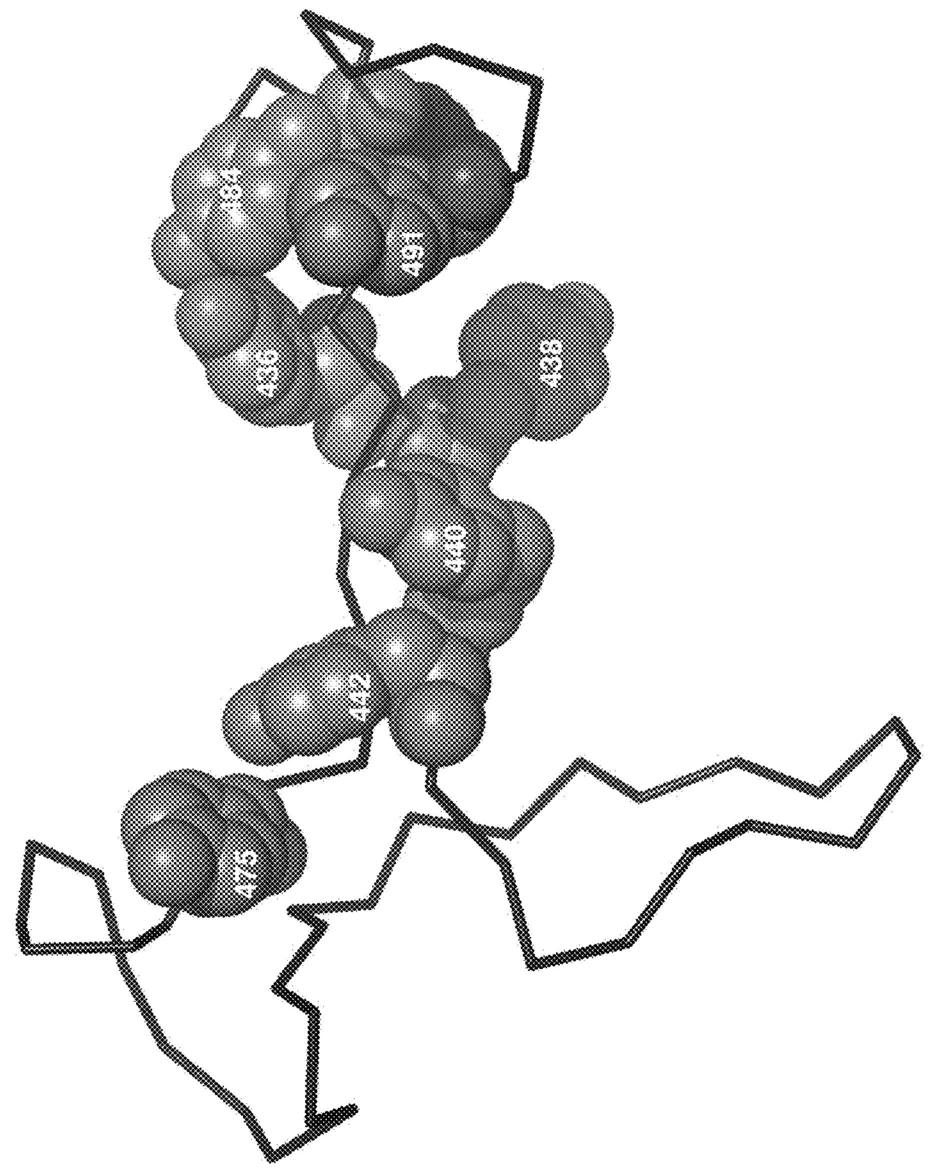

FIG. 7. The distribution of tyrosine residues throughout the RBM region

A graphic representation of the seven tyrosine residues (space-fill) interspersed along the RBM region, six of which are direct contact residues for both ACE2 and mAb 80R (see also FIG. 2).

Figure 8:
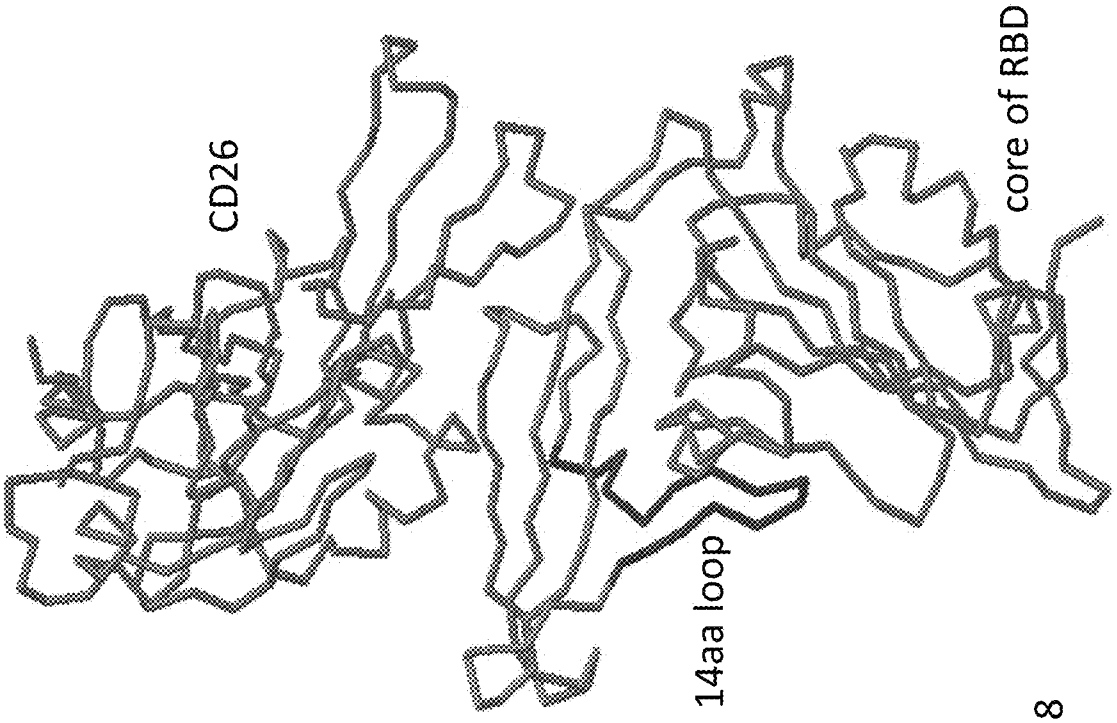

FIG. 8. Schematic representation of the MERS CoV RBD bound to its receptor

Figure shows atomic structure of the MERS RBD bound to its receptor (CD26/DPP4, in purple). The core (in green) of the RBD supports an excursion (marked as RBM, in orange) that contains a 14 aa loop (tacking segment, in red), which does not directly contribute to the recognition of the CD26 receptor. Hence the inventors' proposed another cloning strategy for MERS, as demonstrated in FIGS. 9A-9B.

FIGS. 9A-9E Reconstitution of the MERS CoV RBM

Figure 9A:
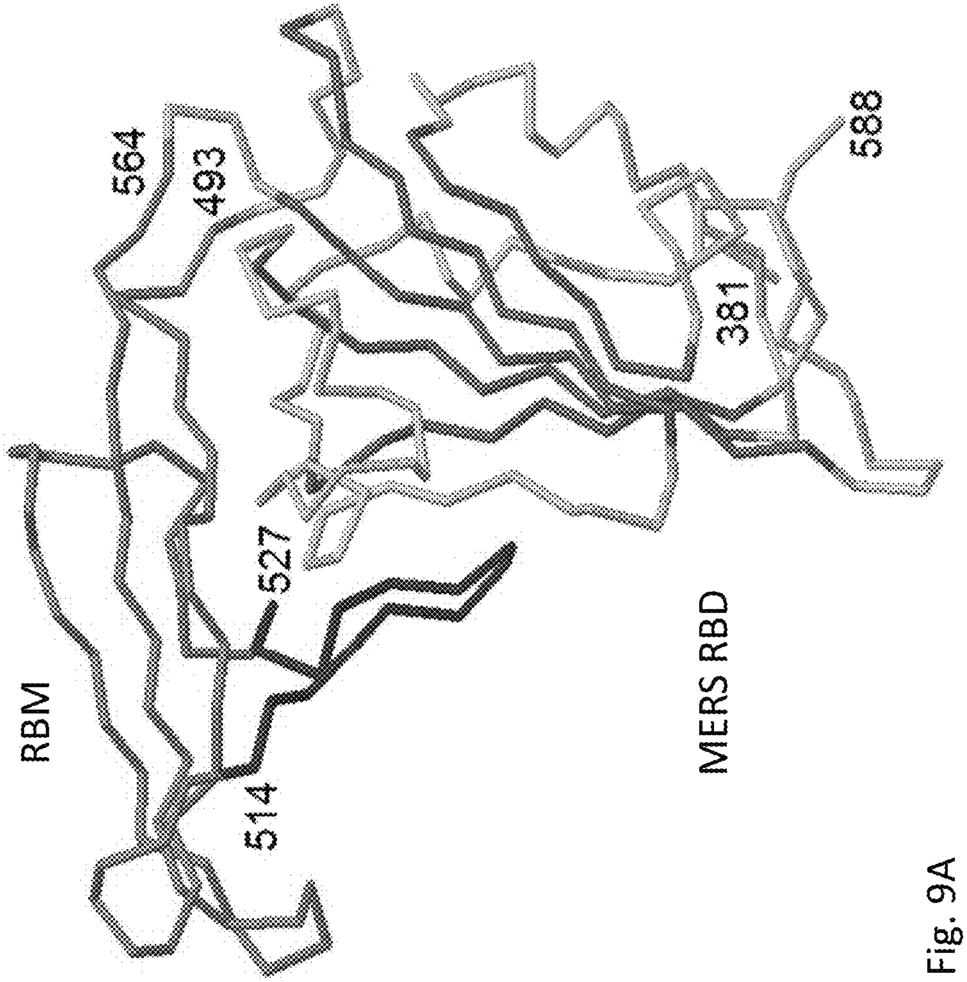

FIG. 9A shows the RBD and RBM (in orange) of MERS CoV. The loop region is shown in blue.

FIG. 9B shows the RBM devoid of the core and loop (connecting residues 514 and 527, SEQ ID NO: 43). Segments shown are of residues 492-514, denoted by SEQ ID NO: 8 and 527-565, denoted by SEQ ID NO: 18).

FIG. 9C shows the area shown in FIG. 9B with a linker (L, in grey) bridging the gap of 18 Å between residues 514 and 527. The three β strands formed by residues 497-505 (denoted by SEQ ID NO: 19), 552-562 (denoted by SEQ ID NO: 20) and 537-545 (denoted by SEQ ID NO: 21) are in green, blue and red, respectively. The presence of Cys-503 in β strand 497-505 (green) may require a linker containing a central cysteine residue flanked by 1-3 random residues (X) on either side.

FIG. 9D shows the extensive hydrogen bonding within the RBM.

FIG. 9E shows hairpin 538-559 (denoted by SEQ ID NO: 83) which represents a target for reconstitution of a partial epitope comprising the amino acid residues 538-545 (denoted by SEQ ID NO: 46), 552-559 (denoted by SEQ ID NO: 47) and a linker. A linker may be introduced to bridge residue 545 with residue 552.

Figure 10:
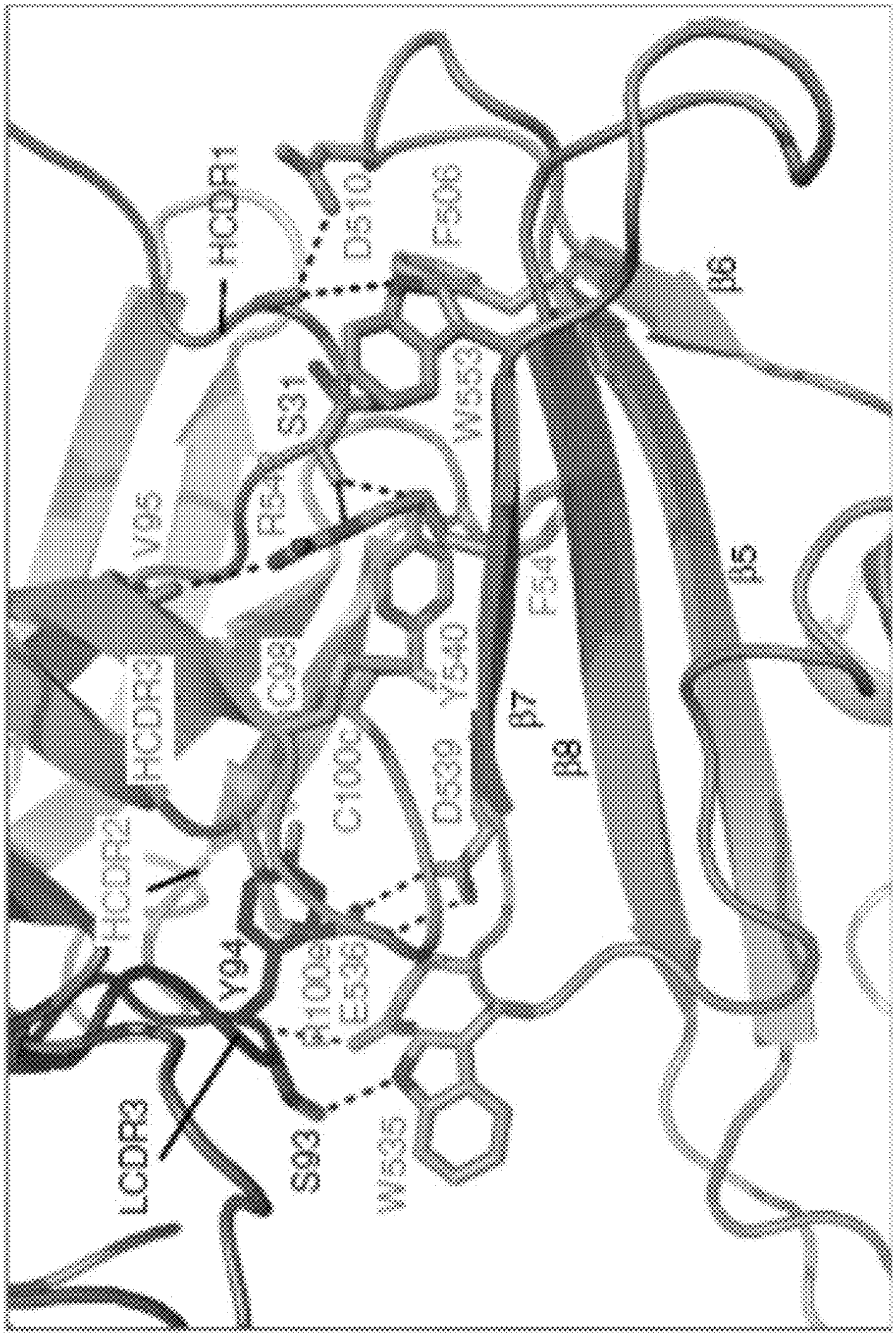

FIG. 10. Schematic presentation of the MERS CoV RBM bound to mAb m336.

Contact is primarily between the CDR loops of the mAb and strand 7. Significant contact residues in MERS CoV RBM are shown (W535, E536, Y540, R542 and W553 contributed by β strand 8). The figure has been adapted from Ying, T., et al. (2015).

Figure 11A:
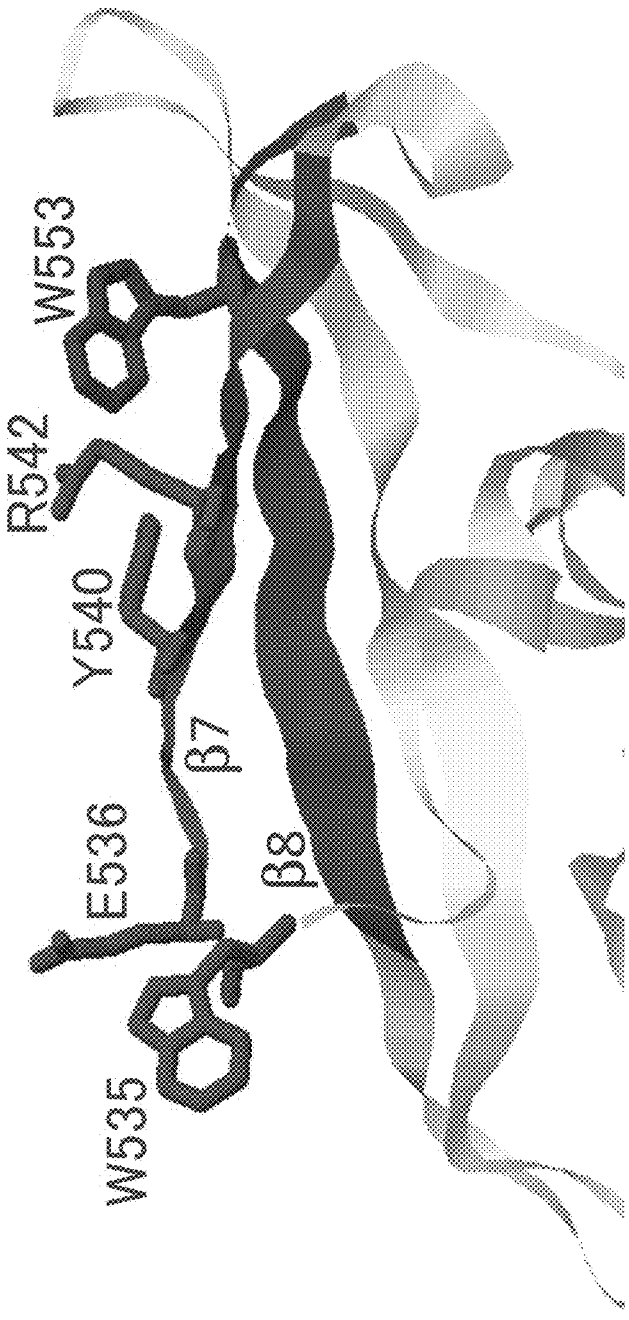

FIGS. 11A-11E. A graphic representation of the binding interface of the MERS-CoV receptor binding motif FIG. 11A is a ribbon diagram indicating the contact residues with the monoclonal antibody mAb m336. The β strand 7 (red) and the β strand 8 (blue) are the two upper most strands shown.

FIG. 11B shows the same region depicted in FIG. 10A illustrated in backbone representation, without the contact residues. The β strand 7 (red) and the β strand 8 (blue) are highlighted.

FIG. 11C shows only β strands 7 and 8 and all of the residues preceding β7 (namely prior to residue 535) and following β8 (namely after 560) were removed.

FIG. 11D is a graphic illustration of β strands 7 and 8 from which the turn connecting amino acid residues 546 to 551 (denoted by SEQ ID NO: 73) were removed and the NNK linkers are indicated.

FIG. 11E shows the amino acid sequences for 535-546 (denoted by SEQ ID NO: 37) and 551-560 (denoted by SEQ ID NO: 38) and indicates the position of the inner and terminal linkers.

Figures 12A, 12B, 12C, 12D, 12E:
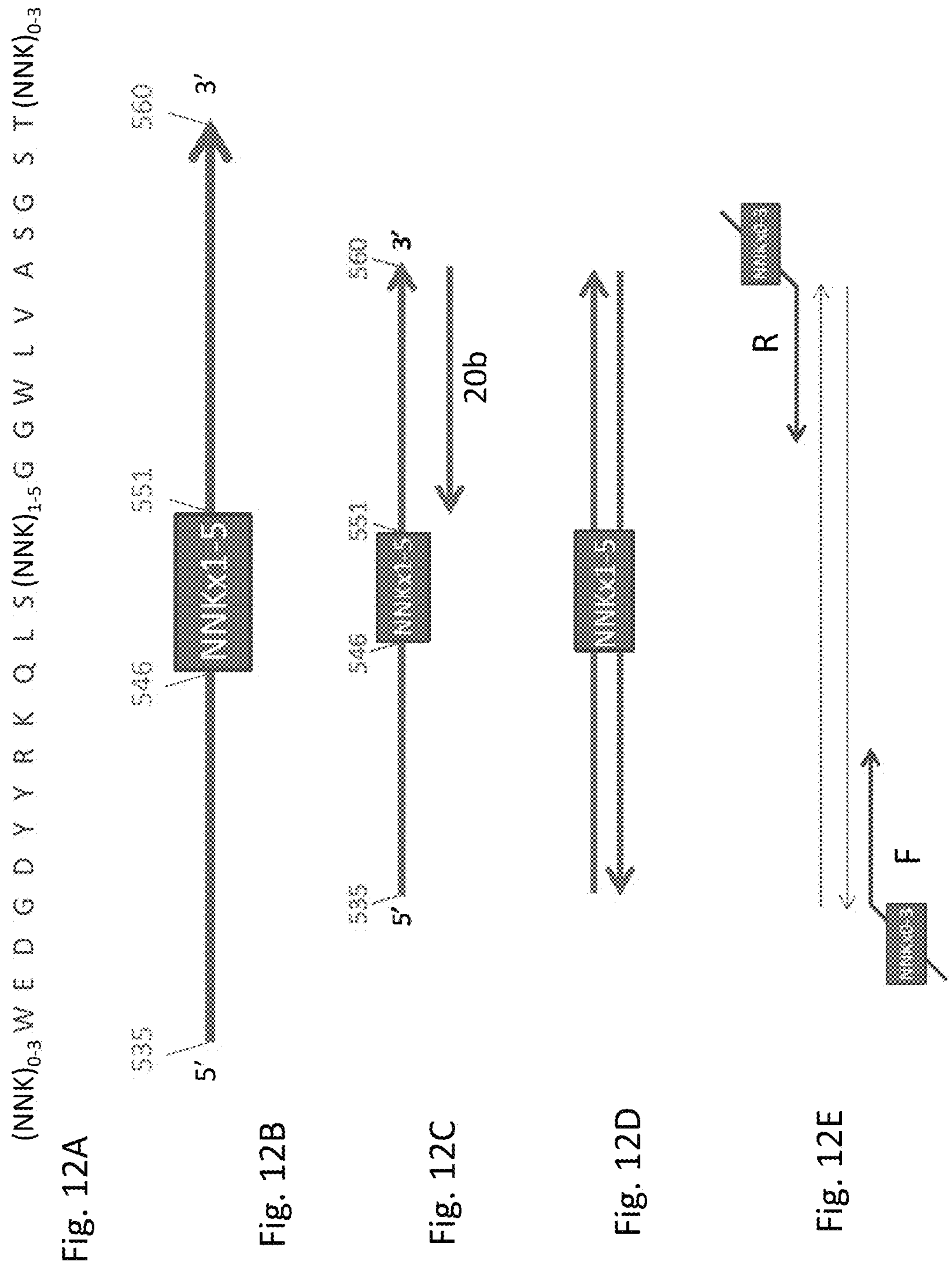

FIGS. 12A-12E. Illustration of the conformer library for preparing MERS-CoV RBM constructs FIG. 12A shows the amino acid sequence of β7 and β8 and indicates the position of the linkers (as in FIG. 11E).

FIG. 12B is a schematic representation of the oligonucleotide encoding amino acid sequences 535-546 (denoted by SEQ ID NO: 37) and 551-560 (denoted by SEQ ID NO: 38) which are separated by an NNK linker of 1, 2, 3, 4, or 5 NNK repeats.

FIG. 12C is a schematic representation of a 20 bases antisense oligonucleotide used to prime the Klenow fill-in of the constructs thus generating double strand DNA templates (shown in FIG. 12D).

FIG. 12E is a schematic illustration of the PCR reaction used to amplify the various ds DNA templates, using forward (F) and reverse (R) primers that at their 5' ends contain 0-3 NNK linkers.

Figure 13:
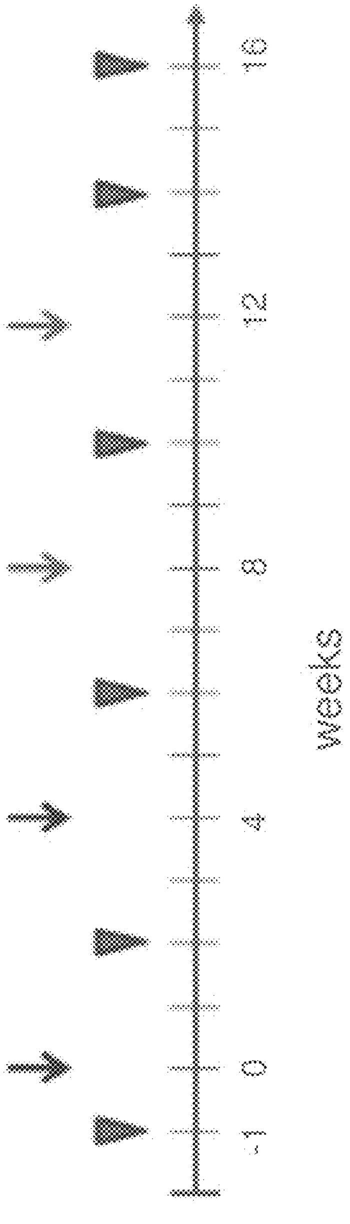

FIG. 13 Vaccination protocol

Polyclonal antisera against MERS-RBM constructs will be generated in rabbits. Each arm of the experiments will consist of a group of 4 female New Zealand White (NZW) rabbits (ca 3 months old) to be immunized with a given antigen in Ribi adjuvant (R-730-Corixa). Rabbits will be immunized by subutaneous (s.c.)+intramuscular (i.m.) routes of administration, injecting a total volume 1 ml/animal/immunization. The immunization and bleed schedule for each animal is illustrated above. Serum collection (triangles). Immunization/boost with MBP-RBM construct (red arrow). Boosts with GST-RBM construct (green arrow).

DETAILED DESCRIPTION OF THE INVENTION

The present invention contends with development of specific and effective vaccines and vaccine-based therapeutic applications targeting viral pathogens, for example, CoVs that may infect any mammalian or avian subjects. Non-limiting examples for such CoVs relate to MERS CoV and SARS CoV in particular. The vaccines are based on exact reconstitution of the functional binding-motif of the CoVs Spike protein (S1) and generation of recombinant peptides characterized by high affinity and specificity to CoVs receptors and neutralizing antibodies.

The present invention is based on the rationale that as the viral 51 is responsible for the host tropism and for immunogenicity in the host, it would be possible to reconstitute the functional part of the viral 51, namely the Receptor Binding Domain (RBD) or more specifically, the Receptor Binding Motif (RBM), that is capable of both of these functions, thereby targeting viral infections most effectively.

Validity of the proposed approach has been presently exemplified by successful reconstitution of the SARS CoV RBM as an independently-folding, functional binding-domain of 51, and expression of about 40-amino acid long RBM-derived peptides in *E. coli*, which was shown to bind both ligands: the viral receptor ACE2 and the neutralizing mAb 80R (FIGS. 1 to 7). On the basis of the above experiments, the inventors have also developed another epitope-based vaccine targeting MERS CoV, wherein they used a similar methodology to reconstitute MERS (FIGS. 8 to 12). The justification for this approach bases on the fact that the two viruses are extremely similar in their general atomic structures for both the RBD and RBM. The products produced by the technology of the invention serve as an immunogens and vaccines for human and/or veterinary use. For example, for MERS CoV reconstituted RBM, an additional application may be the use of said product as a veterinary vaccine to protect camels or any other camelids, such as the llama, alpaca, guanaco, and vicuña of South America.

Specifically to this point, the proposed invention is very well supported with an example for the construction of a product that illustrates the effective reconstitution of the RBM of SARA CoV. The inventors have methodically demonstrated the selection and production of a number of variants (that differ in linker composition and length) that bind both the native receptor and examples of neutralizing antibodies. Thus, it has been proven that the inventors are able to produce lead molecules based on the technology of the invention. In other words, the present disclosure convincingly documents an enabling method for the production of a similar immunogen for MERS and other CoVs.

Particular advantageousness of the proposed approach is in achieving effective immunogen by focusing the immune response to the RBD neutralizing surface, i.e. RBM. More specifically, to focus the immune response to the RBD neutralizing surface, the inventors expressed a functional RBM as an isolated independent immunogen. It is important to stress that the mere knowledge of the RBM sequence and its components is insufficient to ensure RBM functionality. To guarantee a neutralizing immune response one must express RBM such that it assumes its highly conformational nature. Uniqueness of the proposed approach is that it enables to reconstitute functional RBM (for example FIGS. 1A-1B, 9A-9E) and to achieve an effective immunogen (EXAMPLES 1 to 5).

The approach of the present invention is further distinguished from previous efforts to achieve CoV vaccines basing on the entire RBD peptide in that it produces a product that consists of less than half the entire RBD (ca. 35%) residues and contains unnatural (namely non-native) sequences bridging at least two discontinuous RBM peptides. Non-limiting examples for such discontinuous reconstituted RBM, may comprise the MERS CoV 492-514 and 530-566 (as denoted by SEQ ID NO: 8 and 65, respectively) or fragments thereof connected via at least one linker. In some alternative embodiments, the reconstituted RBM may comprise the MERS CoV residues 491-514 and 530-567 (as denoted by SEQ ID NO: 66, 67, respectively), connected via at least one linker. In yet some further embodiments, such fragments may comprise MERS CoV 51 residues 491-513 and 528-567 (as denoted by SEQ ID NO: 68, 69, respectively), or residues 493-513 and 528-564 (as denoted by SEQ ID NO: 70, 71, respectively). Still further, the reconstituted RBM of the invention may comprise MERS CoV amino acid residues 493-514 and 527-564 (as denoted by SEQ ID NO: 44, 45, respectively) or fragments thereof connected via at least one linker. Moreover, the inventors introduce additional modifications to achieve expression of a functional RBM, such as a deletion of the tacking segment, specifically, the 14aa loop (comprising residues 515-529 denoted by SEQ ID NO: 14 or in some embodiments, residues 514-527 denoted by SEQ ID NO: 43) that otherwise interferes with the correct folding and function of the desired immunogen. This knowledge is critical and non-obvious, and represents a key feature of the present invention.

In yet some further embodiments, were the reconstituted RBM of the invention comprise a partial sequence of the native RBM, any sequences or amino acid residue/s thereof. In some embodiments, the linker/s may replace at least one amino acid residues not directly involved or participate in receptor and/or neutralizing antibodies (nAb/s) binding. More specifically, residues not directly involved in binding or contact, include residues that may not serve necessarily as "contact residues", but impact receptor and/or nAb/s binding, for example by conferring or maintaining certain conformation required for said binding. These specific residues may be replaced, substituted, excluded or removed in/from the functional reconstituted RBM polypeptides of the invention. In yet some further alternative embodiments, residues that may function as "contact residues" for the receptor and/or nAbs, may be replaced by at least one linker/s. In yet some further embodiments, at least one residue involved directly or indirectly in receptor and/or nAb/s binding, may be replaced by said linkers. not involved in the receptor and/or nAbs interactions, may be replaced. Thus, in certain embodiments, sequences or residues that are not essential for binding and may be replaced by at least one linker, include for example, residues 545-552 or 546-551 (as denoted by SEQ ID NO: 72, 73, respectively). In some further embodiments, discontinuous reconstituted MERS-CoV RBM may comprise residues 538-544 and 553-559, (as denoted by SEQ ID NO: 74, 75, respectively), in further embodiments, such fragments may comprise MERS CoV 51 residues 535-546 and 551-560 (as denoted by SEQ ID NO: 37, 38, respectively). In yet some further alternative embodiments, the reconstituted RBM polypeptides of the invention may comprise at least 1, 2, 3, 4, 5, 6, 7, 8, 9, 10, 11, 1, 13, 14, 15, 16, 17, 18, 19, 20, 21, 22, 23, 24, 25, 26, 27, 28, 29, 30 or more residues that directly or indirectly participate in receptor and/or nAb/s binding.

It should be appreciated that in certain embodiments, the MERS-CoV fragments referred to herein by amino acid residues position, refer to the MERS-CoV 51 protein amino acid sequence as denoted by SEQ ID NO: 34.

The need for vaccines against emerging threats is unquestionable. This is all the more important when the viral threat has a relatively high mortality rate and is internationally spread. The previous epidemic of the SARS CoV affected thousands of people worldwide. Over the years this disease seems to have become less worrisome, most probably due to the fact that less than 10% of those infected develop serious or fatal disease. In contrast, the MERS CoV is already of a much greater concern. The immediate implications of the MERS epidemic in countries of the Middle and Far East are of obvious concern in these geographic regions. The spread of the disease via camels and during the Haj pilgrimage makes the disease a bona fide threat. The fact that it has already spread to the Far East and hundreds of cases have been reported in Korea and in China emphasizes the fact that there is an emerging pandemic that could be devastating should the virus gain greater efficacy in spreading from person to person. Hence there is a genuine need for an effective prophylactic MERS vaccine. The present invention addresses this need, specifically, by providing reconstituted RBM molecules that may be used as efficient vaccines.

Thus, according to a first aspect, the invention relates to an isolated recombinant polypeptide comprising an amino acid sequence of at least one reconstituted Receptor Binding Motif (RBM) of a viral Spike protein, or of any fragments thereof. More specifically, the reconstituted RBM of the invention may comprise at least one linker and at least one fragment of the native RBM. In some specific embodiments, the native RBM is a 30 to 200 amino acid sequence comprised within the Receptor Binding Domain (RBD) of said Spike protein forming a binding interface that interacts with the viral receptor. It should be further noted that in some embodiments, the native RBM is an extended 30 to 100 or more amino acid excursion, juxtaposed along the edge of the core of the RBD and tacked to the core via a tacking segment. In some specific embodiments, the reconstituted RBM comprises at least one exogenous linker. More specifically, at least one of said linker/s may replace at least one of: the tacking segment, any part or amino acid residue/s thereof and any RBM fragment or amino acid residue/s. In some embodiments, the linker/s may replace at least one amino acid residues not directly involved or participate in receptor and/or neutralizing antibodies (nAb/s) binding. In yet some further alternative embodiments, residues that may function as "contact residues" for the receptor and/or nAbs, may be replaced by at least one linker/s. In yet some further embodiments, at least one residue involved directly or indirectly in receptor and/or nAb/s binding, may be replaced by said linkers.

The polypeptide of the invention is derived from a particular region of the receptor binding domain of a spike protein, or any other peplomer, that interacts with the viral receptor on the target cell. A "peplomer", as used herein, a glycoprotein structural unit found on viral capsid or the lipoprotein envelope of enveloped viruses, e.g. H and N spikes of influenza virus. The peplomers are essential for both host specificity and viral infectivity. The term "peplomer" or "spike" is typically used to refer to a grouping of heterologous proteins on the virus surface that function together. The term receptor binding domain (RBD) as used herein refers to a region, segment or domain within a polypeptide studding (or covering) the envelope of a virus that is associated with or mediates the binding of the virus to a host cell, in particular to a host cell receptor. Polypeptides studding the envelope of a virus are commonly referred to as spikes or spike proteins. Influenza virus, for instance, has two types of spikes, the hemagglutinin protein (HA) and the protein neuraminidase (NA). Another example is the spike glycoprotein (S) of MERS-CoV that targets the cellular receptor dipeptidyl peptidase 4 (DPP4). Interaction between the spike protein and DPP4 is mediated by a RBD on the viral spike. It has been reported that MERS-CoV RBD consists of a core and a receptor-binding subdomain (which is also referred to herein as a "receptor binding motif", RBM). RBM may be identified by any method known in the art based on the interaction formed between the spike protein and a host cell. Particular RBD encompassed by the present disclosure are of the spike proteins of MERS CoV and SARS CoV, the amino acid sequences of which are denoted by the amino acid sequences SEQ ID NO: 43 and SEQ ID NO: 31, respectively.

The reconstituted RBM polypeptides may comprise at least one amino acid residue derived from the RBM of the CoV 51 proteins specified above.

The term receptor binding motif (RBM) as used herein refers to a region within the RBD that is in direct contact with the host cell or the viral receptor on the host cell. In other words the term refers to a region within a polypeptide studding (or covering) the envelope of a virus, specifically within the RBD thereof, that mediates binding between the virus and host cell though non-covalent interactions. For example and as described herein, the co-crystallization of the SARS-CoV RBD bound to its receptor ACE2 revealed that the actual binding interface lies within an extended excursion juxtaposed along the edge of the core of the RBD and constitutes the Receptor Binding Motif. The RBM may be identified by any method known in the art based on the interaction formed between the spike protein and a host cell.

In certain embodiments, the RBM of the viral spike protein may be an extended 30, 31, 32, 33, 34, 45, 46, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 96, 97, 98, 99, 100, 110, 120, 130, 140, 150, 160, 170, 180, 190, 200 or more amino acid excursion. As noted above, at least part of the RBM participates in receptor interaction.

As indicated above, the invention provides reconstituted RBMs that comprise at least one linker and at least one fragment derived from a native RBM. Reconstituted RBM, as used herein refers to a recombinant or synthetically non-natural RBM, build up again from parts, reconstructed, recombined and recomposed of fragments of the native RBM, that may in certain embodiments attached or linked together by at least one linker. As noted above, the reconstituted RBM of the invention comprise at least one fragment or amino acid residue or sequence of the native or natural RBM, and at least one exogenous linker. Specific embodiments for the reconstituted RBMs provided by the invention are described in more detail herein after. Native protein as used herein refers to a protein in its properly folded and/or assembled form, which is operative and functional. The native state of a protein may possess all four levels of bio-molecular structure, with the secondary through quaternary structure being formed from weak interactions along the covalently-bonded backbone. In still further embodiments, this term relates to the RBM of the natural S1 protein as appropriately expressed and presented in the natural viral envelop or capsid. More specific embodiments refer to RBM of the S1 protein of different CoVs, specifically, the RBMs of S1 proteins of SARS-CoV and MERS-CoV. In yet some further particular non limiting embodiments, this term refers to the RBMs derived from S1 proteins of SARS-CoV (SEQ ID NO. 31) and MERS-CoV (SEQ ID NO. 34).

Thus, in some embodiments, the reconstituted RBMs of the invention may comprise the sequence of the native RBM, were residues, fragments or segments that are not directly involved or participate in receptor interaction or receptor contact may be replaced by at least one linker. It should be however understood that the reconstituted RBMs of the invention may comprise at least part, and preferably, most or all residues that participate in interaction with the receptor. In yet some further alternative embodiments the linker/s of the reconstituted RBMs of the invention may replace at least one amino acid residues involved directly or indirectly in receptor and/or nAb/s binding. Nevertheless, it should be understood that in some embodiments, the reconstituted RBMs of the invention may comprise at least one or more, specifically, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 2, at least 23, at least 24, at least 25, at least 26, at least 27, at least 28, at least 29 at least 30 or more amino acid RBM amino acid residues that are directly or indirectly involved in in receptor and/or nAb/s binding.

In this connection, it should be noted that in certain embodiments, amino acid sequences or amino acid residues that are not directly or indirectly involved in interaction with various neutralizing antibodies, may be also replaced, removed, excluded or substituted by at least one linker. The reconstituted RBMs of the invention may comprise the amino acid sequence of the native RBM, or of any fragment thereof. "Fragment" with respect to polypeptide sequences means polypeptides that comprise at least 10%, at least 20%, at least 30%, at least 40%, at least 50%, at least 60%, at least 70%, at least 80%, at least 90% or at least 95% of the complete segment of the native RMB of said viral spike protein, specifically the CoV S1. In some embodiments, fragments of the RBMs may comprise at least 5, at least 10, at least 15, at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more and at least 100 amino acids or more of said spike RBMs.

As indicated above, the reconstituted RBM of the invention comprises at least one linker that replaces in some embodiments, the tacking segment of the native RBM, or any part or amino acid residue/s thereof. As such, in some embodiments the reconstituted RBM of the invention lacks at least part of the native tacking segment. In further embodiments, the reconstituted RBM of the invention may comprise more than one linker, for example, 2, 3, 5, 6, 7, 8, 9, 10 or more that replace at least part of the tacking segment, or a sequence that comprise at least part of the tacking segment. It should be further appreciated that in some particular embodiments, in addition to linker/s that replace the tacking segment, the reconstituted RBM of the invention may further comprise at least one linker that replace/s at least one amino acid residue/s located in other segments of the native RBM. In yet some further embodiments, the reconstituted RBM polypeptide of the invention may comprise at least one linker that replaces at least one amino acid residue of the RBM, or any fragments thereof not directly involved in reception and/or nAb/s binding. Alternatively, the linker/s may replace at least one amino acid residue of the RBM directly or indirectly involved and participate in reception and/or nAb/s binding.

Still further, the reconstitute RBM polypeptides of the invention may comprise between about 10 to 100 amino acid residues, specifically, between about 20 to 50 amino acid residues. Specifically, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 45, 46, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 96, 97, 98, 99, 100 or more amino acid residues. In some specific embodiments, the reconstitute RBM polypeptides of the invention may comprise at least one amino acid sequence derived from the RBM of a Coronavirus (CoV) S1 protein.

Thus, the main goal of the present invention is to provide means to combat Coronaviruses (CoVs) infections and to prevent spread of such infections via other animals to humans and/or to domestic animals as well as to prevent human to human infections. CoVs are common in humans and usually cause mild to moderate upper-respiratory tract illnesses. There are four main sub-groupings of coronaviruses, known as alpha, beta, gamma, and delta. The six coronaviruses known to-date as infecting humans are: alpha coronaviruses 229E and NL63, and beta coronaviruses OC43, HKU1, SARS-CoV (the coronavirus that causes severe acute respiratory syndrome, SARS), and MERS-CoV (the coronavirus that causes Middle East Respiratory Syndrome, or MERS). The SARS-CoV is a lineage B beta Coronavirus and the MERS-CoV is a lineage C beta Coronavirus.

Coronaviruses are species in the genera of virus belonging to one of two subfamilies Coronavirinae and Torovirinae in the family Coronaviridae, in the order Nidovirales. Herein this term refers to the entire family of Coronavirinae (in the order Nidovirales). Coronaviruses are enveloped viruses with a positive-sense single-stranded RNA genome and with a nucleocapsid of helical symmetry. The genomic size of coronaviruses ranges from approximately 26 to 32 kilobases, the largest for an RNA virus. The name "coronavirus" is derived from the Latin corona, meaning crown or halo, and refers to the characteristic appearance of virions under electron microscopy (E.M.) with a fringe of large surface projections creating an image reminiscent of a crown. This morphology is created by the viral spike (S) peplomers, which are proteins that populate the surface of the virus and determine host tropism.

There are many CoVs that naturally infect animals, the majority of these usually infect only one animal species or, at most, a small number of closely related species, but not humans. CoV strains that are particular subject of the present invention, due to their extreme virulence and hazard in humans, are those that have been transmitted from animals to humans. For example, SARS-CoV can infect people and animals, including monkeys, Himalayan palm civets, raccoon dogs, cats, dogs, and rodents. MERS-CoV has also been found to infect people and animals, including camels and bats. Therefore, in certain embodiments, the Coronavirus may be a CoV infecting mammalian subject/s, avian subject/s or any other vertebrates.

Thus the term Coronaviruses (designated herein CoVs) for the purposes of the present invention encompasses four main sub-groupings of coronaviruses, known as Alpha, Beta, Gamma, and Delta. More specifically, under this term is meant the enveloped viruses with a positive-sense RNA genome (ssRNA+) and with a nucleocapsid of helical symmetry; and also large RNA viruses with the genomic size of ranges from approximately 26 to 32 kilobases; and further viruses with the characteristic morphology of large, bulbous surface projections under electron microscopy, which is created by the viral spike (S) peplomers, i.e. viral surface proteins determining host tropism and immunogenicity.

The present invention in particular concerns the two novel coronaviruses that have emerged in humans in the twenty-first century: severe acute respiratory syndrome coronavirus (SARS-CoV) and Middle East respiratory syndrome coronavirus (MERS-CoV), both of which cause acute respiratory distress syndrome (ARDS) and are associated with high mortality rates. There are currently no clinically approved vaccines or antiviral drugs available for either of these infections; thus, the development of effective therapeutic and preventive strategies that can be readily applied to new emergent strains is a research priority.

In the specific case of the SARS CoV, a defined receptor-binding domain on S mediates the attachment of the virus to its cellular receptor, angiotensin-converting enzyme 2 (ACE2) (see below). Some CoVs, specifically the members of Beta CoV subgroup A, also have a shorter spike-like protein called hemagglutinin esterase (HE).

In some non-limiting embodiments, the present invention may be particularly applicable to the six CoVs that can infect humans, specifically the Alpha CoVs 229E and NL63, and Beta CoVs OC43, HKU1, SARS-CoV and MERS-CoV. Specifically for the Beta-CoVs, which are of the greatest clinical importance concerning humans, these are OC43, and HKU1 of the A lineage, SARS-CoV of the B lineage, and MERS-CoV of the C lineage. MERS-CoV is the first Beta CoV belonging to lineage C that is known to infect humans. The Alpha and Beta CoVs genera descend from the bat gene pool. It should be further noted that human CoVs are difficult to grow in the laboratory. Coronaviruses infecting animals are also contemplated, in particular the bat coronaviruses HKU4 and HKU5.

Within the above group of human CoVs, of particular relevance to the present invention are the SARS CoV associated with Severe Acute Respiratory Syndrome, and the MERS CoV associated with Middle East Respiratory Syndrome, as for being the primary causes of life-threatening infectious diseases and epidemics in humans.

The other human CoVs are believed to cause a significant percentage of all common colds in human adults (primarily in the winter and early spring seasons). In certain individuals CoVs may further be a direct or indirect cause of pneumonia, i.e. direct viral pneumonia or a secondary bacterial pneumonia.

In some specific embodiments, the Coronavirus may be Middle East Respiratory Syndrome coronavirus (MERS CoV).

The term MERS CoV as known in the art refers to a lineage C beta coronavirus (+RNA 30 kb) whose primary natural reservoir resides in bats that infect domesticated camels as opportunistic hosts, which go on to infect humans. MERS-CoV genomes are phylogenetically classified into two clades, clade A and B. The earliest cases of MERS were of clade A clusters (EMC/2012 and Jordan-N3/2012), and new cases are genetically distinct (clade B). MERS-CoV is distinct from SARS-CoV and distinct from the common-cold coronavirus and known endemic human betacoronaviruses HCoV-OC43 and HCoV-HKU1. Until 23 May 2013, MERS-CoV had frequently been referred to as a SARS-like virus, or simply the novel coronavirus, and early it was referred to colloquially as the "Saudi SARS". Over 1,600 cases of MERS have been reported by 2015 and the case fatality rate is >30%. 182 genomes have been sequenced by 2015 (94 from humans and 88 from dromedary camels). All sequences are >99% similar. The genomes can be divided into two clades—A and B—with the majority of cases being cased by clade B. Human and camel strains are intermixed suggesting multiple transmission events.

Like other coronaviruses, the MERS-CoV virion utilizes a large surface spike (S) glycoprotein for interaction with and entry into the target cell. The S glycoprotein consists of a globular 51 domain at the N-terminal region, followed by membrane-proximal S2 domain, a transmembrane domain and an intracellular domain.

Determinants of cellular tropism and interaction with the target cell are within the S 1 domain, while mediators of membrane fusion have been identified within the S2 domain. Through co-purification with the MERS-CoV SI domain, dipeptidyl peptidase 4 (DPP4) was identified as cellular receptor for MERS-CoV. DDP4 is expressed on the surface of several cell types, including those found in human airways, and possesses ectopeptidase activity, although this enzymatic function does not appear to be essential for viral entry.

More specifically, Dipeptidyl peptidase-4 (DPP4), also known as adenosine deaminase complexing protein 2 or CD26 (cluster of differentiation 26) is a protein that, in humans, is encoded by the DPP4 gene (a nucleic acid sequence thereof has for example the accession number Gene ID: 1803).

The protein encoded by the DPP4 gene is an antigenic enzyme expressed on the surface of most cell types and is associated with immune regulation, signal transduction and apoptosis. It is an intrinsic membrane glycoprotein and a serine exopeptidase that cleaves X-proline dipeptides from the N-terminus of polypeptides. The substrates of CD26/DPPIV include proline (or alanine)-containing peptides and also include growth factors, chemokines, neuropeptides, and vasoactive peptides. DPP4 plays a major role in glucose metabolism.

It should be therefore appreciated that the reconstituted RBM of the invention is capable of interacting and binding the cellular receptor for MERS-CoV.

The newer MERS-CoV, first reported in the summer of 2012 in a pneumonia patient in Saudi Arabia, has been associated with symptoms include renal failure and severe acute pneumonia with often fatal outcome. The complete genome of the ChinaGD01 strain is under Acc. Num. KT006149. Of particular relevance is the sequences of the MERS-CoV-Jeddah-human-1 (Acc. Num. KF958702) and the MERS-CoV-Jeddah-camel-1 (Acc. Num. KF917527) isolates that are 100% identical and contain characteristic, suggesting direct cross-species transmission from the camels to the patient.

As noted in the following examples (specifically, Example 6), the MERS-CoV RBM contains three strands (residues 497-506, 536-544, 553-565, as denoted by SEQ ID Nos: 22, 23 and 24, respectively). In yet some further embodiments, the three strands of MERS-CoV SS1 RBM may include residues 497-505, 537-545, 552-562, as denoted by SEQ ID NOs: 19, 21 and 20, respectively), a single disulfide bond (between Cys 503 and Cys 526) and an amino acid loop serving as the tacking segment that tacks the RBM to the core. Thus, in more specific embodiments, the native RBM may comprise any one of: (a) residues 498 to 562 (denoted by SEQ ID NO: 79), residues 498 to 564 (denoted by SEQ ID NO: 78), or residues 498-565 (SEQ ID NO: 15) of the MERS-CoV Spike protein (as denoted by SEQ ID NO: 34); (b) residues 498 to 562 with at least one flanking amino acid residue/s; or (c) any fragments thereof. As noted above, the native MERS-CoV RBM may comprise the amino acid sequence of at least any one of residues 498-562, residues 498-564, or residues 498-656 as denoted by SEQ ID NOs. 79, 78 and 15, respectively, any fragments thereof, or alternatively, may comprise further flanking residues. In some non-limiting embodiments, the native MERS RBM may comprise residues 483-568 (as also denoted by SEQ ID NO: 16). Alternatively, the RBM may comprise residues 491-567 (as denoted by SEQ ID NO: 13).

In yet some further embodiments, the RBM may comprise residues 498-565 (denoted by SEQ ID NO: 15), still further, the RBM may comprise residues 492-566, or alternatively, residues 493-564, as denoted by SEQ ID NO: 15, 76, 42, respectively.

Still further, the tacking segment may be an amino acid loop comprising any one of: (d) residues 515 to 527 of the MERS-CoV Spike protein (as denoted by SEQ ID NO: 86); (e) residues 515 to 527 with at least one flanking amino acid residue/s; or (f) any fragments thereof. In certain embodiments as an alternative loop, the invention further encompasses a loop comprising residues 512-530 of MERS (as denoted by SEQ ID NO: 17). In yet some further embodiments, the loop may comprise residues 515-529, or alternatively, residues 514-527, as denoted by SEQ ID NO: 14 and 86, respectively.

It should be appreciated that in certain embodiments, the 51 MERS-CoV-derived segments, are referred to by amino acid residue positions that in certain embodiments refer to the 51 MERS-CoV amino acid sequence as denoted by SEQ ID NO: 34.

In more specific embodiments, the polypeptide of the invention may comprise reconstituted RBM comprising at least one linker that replace/s the loop (tacking segment) or any part or at least one amino acid residue thereof. In yet further embodiments, the reconstituted RBM of the invention may further comprise additional linker/s that may replace or may be added to further residues of other RBM segments (that are located out of the loop).

In some embodiments, the reconstituted RBM may comprise at least two linkers replacing residues 515 to 525 (also denoted by SEQ ID NOs: 25) and residues 527 to 529 of the MERS-CoV Spike protein. In some specific embodiments, this linker retains the original Cys526 residue of MERS-CoV.

In yet some other embodiments, the reconstituted RBM may comprise at least one linker replacing residues 515 to 525 of the MERS-CoV Spike protein (SEQ ID NO: 25).

Still further, the reconstituted RBM may comprise at least one linker replacing residues 515 to 529 of the MERS-CoV Spike protein (SEQ ID NO: 14).

In yet some other embodiments, the reconstituted RBM may comprise at least one linker replacing residues 514 to 527 of the MERS-CoV Spike protein (SEQ ID NO: 43).

As indicated above, in some particular embodiments, the reconstituted RBM of the invention may comprise at least one linker that replaces the loop tacking segment or any part thereof and optionally at least one further linker that replaces at least one amino acid residue located in other parts of the RBM. In certain embodiments, such additional linker/s may replace for example Cys503. In more specific embodiments, such additional linker may be an amino acid linker that replaces Cys503 with any other amino acid residue, for example, Ser or Gly.

In some alternative embodiments, the linker may replace residues other than Cys503, and therefore retain the Cys503.

In yet some further embodiments, the reconstituted RBM may comprise at least one linker that may replace or may be added to other parts or fragments of the native RBM. More specifically, at least one of the linker/s may replace at least one RBM fragment or amino acid residue/s not directly involved in receptor binding.

In some other embodiments, the reconstituted RBM may comprise at least one linker replacing residues 545 to 552 of the MERS-CoV Spike protein (SEQ ID NO: 72).

In some other embodiments, the reconstituted RBM may comprise at least one linker replacing residues 546 to 551 of the MERS-CoV Spike protein (SEQ ID NO: 73).

Thus, in accordance with said embodiment, the reconstituted RBM of the invention may comprise residues 535-546 and 551-560 of MERS-CoV (SEQ ID NO: 37 and SEQ ID NO: 38, respectively). In yet some alternative embodiments, the linker comprised within the reconstituted RBM polypeptide of the invention may replace at least one RBM fragment or amino acid residue directly or indirectly involved in receptor and/or nAb/s binding.

It should be appreciated however, that at least some of the reconstituted RBM polypeptides of the invention comprise at least one or more amino acid residue/s directly or indirectly involved in receptor and/or nAb/s binding.

It is to be understood that when referring to MERS residues, the amino acid sequences of these fragments are derived from the MERS-CoV amino acid sequence as denoted by SEQ ID NO: 34.

As shown in FIG. 10, several amino acid residues of MERS-CoV native RBM are essential for the interaction with the neutralizing antibody m336. Thus, in some specific embodiments, the reconstituted RBM of the invention may comprise sequences that include at least part of these residues. In more specific embodiments, the reconstituted RBM of the invention may comprise at least one of W 535, E536, Y540, R542 or W553. In further embodiments, the reconstituted RBM of the invention may comprise at least one, at least two, at least three, at least four or all five indicated residues.

The reconstituted RBM polypeptides of the invention comprise at least one linker. The term "linker" in the context of the invention concerns an amino acid sequence of from about 1 to about 10 or more amino acid residues positioned within and/or flanking the reconstituted RBM of the invention. The linker may be positioned in the central region of the reconstituted RBM of the invention and/or in at least one of its termini, namely at the C-terminus and/or at the N-terminus thereof. The linker is covalently linked or joined to the amino acid residues in its vicinity. For example, a linker in accordance with the invention may be of 1, 2, 3, 4, 5, 6, 7, 8, 9 or 10 or more amino acid residues long. Linkers are often composed of flexible amino acid residues, for example but not limited to glycine and serine so that the adjacent protein domains are free to move relative to one another. The design of a linker that enables proper folding of the various domains of a protein is well known in the art.

However, the term linker in accordance with the present invention encompasses any amino acid residue, as dictated by the encoding NNK nucleic acid motif.

In some embodiments the linker according to the present invention encompasses 1-10, 1-9, 1-8, 1-7, 1-6, 1-5, 1-4, 1-3 or 1-2 or 1 amino acid residue/s. In other embodiments the linker encompasses 1, 2, 3, 4, 5, 6, 7, 8, 9, 10 or more amino acid residues, and thus, in certain embodiments the linkers may be referred to as $NNK_1$, $NNK_2$, $NNK_3$, $NNK_4$, $NNK_5$, $NNK_6$ $NNK_7$, $NNK_8$, $NNK_9$ and $NNK_{10}$.

In some specific embodiments, for MERS-CoV reconstituted RBM polypeptide, useful linkers may include $NNK_1$, $NNK_2$, $NNK_3$, $NNK_4$ and $NNK_5$.

As known in the art, the term "NNK" refers to a nucleic acid triad encoding an amino acid residue, where "N" denotes any nucleotide (namely a natural or a non-natural nucleotide, e.g. nucleotides based on the DNA nucleobases cytosine (C), guanine (G), adenine (A) and thymine (T)) and where "K" denotes a nucleotide based on guanine (G) or thymine (T).

As detailed below, the linkers as herein defined are based on nucleotide triads of the type "NNK". The linker, when present, may have a length of n repeats which may be the same or different one from the other. In particular the linker may include one NNK (denoted as "$NNK_1$"), two NNK (denoted as "$NNK_2$"), "$NNK_3$", "$NNK_4$" when three or four NNKs are present, respectively, etc. Specifically, the index n may have a value of between 0 to 10.

As noted above, the reconstituted RBM of the polypeptide of the invention comprises at least one linker. It should be appreciated that any linkers or any combination of linkers may be used for the polypeptide of the invention. In certain and non-limiting embodiments, an amino acid linker may be used. In more specific embodiments, the linker used by the invention for the MERS-CoV reconstituted RBM polypeptides of the invention, may comprise 1, 2, 3, 4, 5, 6, 7, 8, 9, 10 amino acid residues, or more. In cases that the reconstituted RBM of the polypeptide of the invention comprise two linkers and more, it must be understood that the linkers may be either different or identical.

Non-binding examples of linkers useful in the present invention are disclosed in Table 2, specifically linkers comprising the amino acid sequence of GFDEQ, PYNYH, SQAPL, LHLP and VVAT, as denoted by SEQ ID NO: 49, 51, 53, 55 and 57, respectively, as well as $NNK_3$, $NNK_2$ and $NNK_1$ linkers such as VYS, RQ, SY, FS, C Y, CF, LG, FQS, SIR, A, QLT, IRK, LQ, PT, RTK, RLT and LP. It should be noted that amino acid residues are represented herein in their acceptable one-letter code, and in the sequence listing amino acid sequences of 4 amino acid resides or mole are presented in their three-letter code.

Some specific end non-limiting reconstituted MERS-CoV RBM polypeptides of the invention may comprise the amino acid sequence as denoted by any one of SEQ ID NOs. 48, 50, 52, 54, 56, 58, 59, 60, 61, 62, 63 and 64, and any derivatives, enantiomers and fusion proteins thereof.

In yet some other alternative embodiments, the Coronavirus may be Severe Acute Respiratory Syndrome coronavirus (SARS CoV), and therefore, the reconstituted RBM polypeptides of the invention may be derived from the RBM of SARS CoV.

Specifically SARS-CoV has been associated with a viral disorder characterized by high fever, dry cough, shortness of breath (dyspnea) or breathing difficulties, and atypical pneumonia. The complete SARS-CoV has been analyzed and published by Marra et al. 2003. Since then a large number of SARS strains have been isolated and characterized, and are accessible via the Centers for Disease Control and Prevention (CDC), or the National Center for Biotechnology Information, e.g. the sequence of the SARS-CoV Urbani strain is under Acc. Num. AY278741.

More specially, the SARS coronavirus (SARS-CoV) is a lineage B beta coronavirus that causes severe acute respiratory syndrome (SARS). SARS-CoV is a positive and single stranded RNA virus belonging to a family of enveloped coronaviruses. Its genome is about 29.7 kb. The SARS virus has 13 known genes and 14 known proteins. SARS is similar to other coronaviruses in that its genome expression starts with translation of two large ORFs, 1a and 1b, both of which are polyproteins. The functions of several of these proteins are known, ORFs 1a and 1b encode the replicase and there are four major structural proteins: nucleocapsid, spike, membrane and envelope. It also encodes for eight unique proteins, known as the accessory proteins, all with no known homologues or function. As noted in the following examples, the SARS-CoV RBM contains two anti-parallel beta strands (β5 and β6), a single disulfide bond and a 16-amino acid loop serving as the tacking segment that tacks the RBM to the core.

Thus, in certain embodiments, the native RBM may comprise residues 432 to 486 of the SARS-CoV Spike protein (SEQ ID NO: 3). In more specific embodiments, the tacking segment may be an amino acid loop comprising residues 444 to 459 of the SARS-CoV Spike protein (SEQ ID NO: 2). It should be understood that the specific RBM fragments of the SARS-CoV, referred to herein by the positions of the amino acid residues, refer to the SARS-CoV 51 amino acid sequence as denoted by SEQ ID NO: 31.

In some embodiments, the reconstituted RBM of the polypeptide of the invention may comprise at least one linker added to or replacing at least one of the tacking loop, any part or amino acid residue/s thereof or at least one RBM fragment or amino acid residue not directly involved with receptor and/or nAb/s interaction or binding. In some particular embodiments, the reconstituted RBM of the invention may comprise additional linker/s that may be located in other segments of the RBM. In some embodiments, the at least one linker of the invention may replace any amino acid sequence or amino acid residue/of the SARS-CoV RBM that comprise at least part of the tacking loop as referred to herein.

It should be noted however, that in some embodiments, the reconstituted RBM of the invention may comprise at least one linker that replaces other fragments or amino acid residues of the native RBM, specifically, at least one linker that replaces fragments or amino acid residues not involved in the receptor-virus and/or nAb/s-virus interaction. These fragments or amino acid resides may be within or of out of the loop segment. Still further embodiments encompass reconstituted RBM polypeptides, wherein at least one amino acid residue/s or fragment/s of the RBM directly or indirectly involved in receptor and/or nAb/s binding is replaced with at least one linker. Non-limiting examples for such residues may include R426 or residues 487-489 of the SARS CoV 51 protein of SEQ ID NO: 31, that participate in contact but are not essential for a functional reconstituted RBM polypeptide.

In more specific embodiments the reconstituted RBM of the polypeptide of the invention may comprise an amino acid linker. In some embodiments, the linkers may comprise at least 1, 2, 3, 4, 5, 6, 7, 8, 9, 10 or more amino acid resides. In yet some more particular embodiments, such linker may comprise for example, 3, 4, 5, 6, 7, 8 or more amino acid residues.

In yet further specific embodiments, the linkers used for the reconstituted RBM of the polypeptide of the invention may comprise the amino acid sequence of $Xaa^1_{(n)}$-$Xaa^2$-$Xaa^3$-$Xaa^4$-$Xaa_{(n)}$ as denoted by SEQ ID NO: 27 or any fragment thereof. More specifically, Xaa' may be any amino acid and n is zero or an integer of from 1 to 5, and wherein: $Xaa^2$, may be a Gly, Glu, Leu or Thr; $Xaa^3$, may be Glu or Asp; and $Xaa^4$, may be Glu, Asn, Pro, Met, Val or Asp.

Still further, the linker applicable for the reconstituted RBM of the polypeptide of the invention may comprise the amino acid sequence of $Xaa^1$-$Xaa^2$-$Xaa^3$ or any fragment thereof. It should be noted that Xaa may be any amino acid. In some embodiments, $X^1$, may be a Gly, Glu or Thr; $X^2$, may be Glu; and $X^3$, may be Glu, Asn, Pro, Met, Val or Asp.

In some specific embodiments, the linker may comprise the amino acid sequence of any one of: Gly-Glu-Met (GEM) and Glu-Glu-Pro (GGP).

In yet some further embodiments, the linker may comprise the amino acid sequence of Xaa'-$Xaa^2$-$Xaa^3$-$Xaa^4$ as denoted by SEQ ID NO: 29 or any fragment thereof, wherein Xaa is any amino acid, and wherein:

$X^1$ is a Gly or Leu; $X^2$, is Glu or Asp; and $X^3$, is Pro, Val or Gly; and $X^4$, is Gly, Met, Asn, Asp or Leu.

In some specific embodiments, linker/s comprising the amino acid sequence of any one of: Gly-Asp-Pro-Met, as denoted by SEQ ID NO: 9, Gly-Asp-Pro-Asn as denoted by SEQ ID NO: 10, Gly-Glu-Val-Asp as denoted by SEQ ID NO: 11 and Gly-Glu-Pro-Leu, as denoted by SEQ ID NO: 12, may be also applicable for the reconstituted RBM of the invention.

In some specific embodiments, the polypeptide of the invention may comprise at least one reconstituted SARS-CoV RBM comprising residues ${}_{432}$STGNYNYKYRL${}_{443}$ as denoted by SEQ ID NO: 5 and ${}_{460}$FSPDGKPCTPCTP-PALNCYWPLNDYGFYTT${}_{486}$ as denoted by SEQ ID NO: 6 or any fragments, mutants or derivatives thereof, linked by or attached to said at least one linker. In some specific and non-limiting embodiments, at least one of the linker/s may replace the loop or any amino acid residue/s or any parts thereof, or any sequence comprising said loop or any parts or fragments thereof.

In yet some alternative embodiments, the polypeptide of the invention may comprise at least one reconstituted SARS-CoV RBM that may be a mutated RBM having a K465I mutation. In more specific embodiments, such mutated reconstituted RBM may comprise residues $_{432}$STGNYNYKYRL$_{443}$ as denoted by SEQ ID NO: 5 and $_{460}$FSPDGIPCTPCTPPALNCYWPLNDYG-FYTT$_{486}$ as denoted by SEQ ID NO: 30 or any fragments or derivatives thereof, linked by said at least one linker. In some embodiments, said linker may replace the loop or any parts thereof, or any sequence comprising said loop or any parts thereof. In some particular and non-limiting examples, the reconstituted RBM of the invention may comprise $_{432}$STGNYNYKYRL$_{443}$ as denoted by SEQ ID NO: 5 and $_{460}$FSPDGIPCTPCTPPALNCYWPLNDYGFYTT$_{486}$ as denoted by SEQ ID NO: 30 or any fragments or derivatives thereof, linked by GEM. Such reconstituted RBM may be referred to by the invention as GEM465I.

Still further particular embodiments of the invention provide reconstituted RBM of the polypeptide of the invention that comprises $_{432}$STGNYNYKYRL$_{443}$ as denoted by SEQ ID NO: 5 and $_{460}$FSPDGIPCTPCTPPALNCYWPLN-DYGFYTT$_{486}$ as denoted by SEQ ID NO: 30 or any fragments or derivatives thereof, linked by EEP. Such reconstituted RBM may be referred to by the invention as EEP465I.

Particular and on-limiting examples for reconstituted SARS-CoV RBM polypeptides may comprise the amino acid sequence of at least one of SEQ ID NOs. 89-110, or any derivatives, enantiomers and fusion proteins thereof.

The invention thus provides reconstituted RBMs, specifically, CoV-derived reconstituted RBMs polypeptides. These RBM polypeptides are in some embodiments, isolated and purified polypeptides. In some specific embodiments, these reconstituted RBM polypeptides may be recombinant polypeptides, that may in some embodiments recombinantelly produced. However, the invention further encompasses reconstituted RBMs that are produced synthetically.

An 'isolated polypeptide' is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms. By definition, isolated peptides are also non-naturally occurring, synthetic peptides. Methods for isolating or synthesizing peptides of interest with known amino acid sequences are well known in the art.

The polypeptide of the invention are therefore considered as proteinaceous material. A "proteinaceous material" is any protein, or fragment thereof, or complex containing one or more proteins formed by any means, such as covalent peptide bonds, disulfide bonds, chemical crosslinks, etc., or non-covalent associations, such as hydrogen bonding, van der Waal's contacts, electrostatic salt bridges, etc.

The reconstituted RBM polypeptides of the invention are composed of an amino acid sequence. An 'amino acid/s' or an 'amino acid residue/s' can be a natural or non-natural amino acid residue/s linked by peptide bonds or bonds different from peptide bonds. The amino acid residues can be in D-configuration or L-configuration (referred to herein as D- or L-enantiomers). An amino acid residue comprises an amino terminal part ($NH_2$) and a carboxy terminal part (COOH) separated by a central part (R group) comprising a carbon atom, or a chain of carbon atoms, at least one of which comprises at least one side chain or functional group. $NH_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature are listed in 37 C.F.R. 1.822(b)(2). Examples of non-natural amino acids are also listed in 37 C.F.R. 1.822(b)(4), other non-natural amino acid residues include, but are not limited to, modified amino acid residues, L-amino acid residues, and stereoisomers of D-amino acid residues. Naturally occurring amino acids may be further modified, e.g. hydroxyproline, γ-carboxyglutamate, and O-phosphoserine.

Thus, the reconstituted RBM polypeptides of the invention may comprise natural or non-natural amino acid residues, or any combination thereof.

Further, amino acids may be amino acid analogs or amino acid mimetics. Amino acid analogs refer to compounds that have the same fundamental chemical structure as naturally occurring amino acids, but modified R groups or modified peptide backbones, e.g. homoserine, norleucine, methionine sulfoxide, methionine methyl sulfonium. Amino acid mimetics refers to chemical compounds that have a structure that is different from the general chemical structure of an amino acid, but that function in a manner similar. Amino acids may be referred to herein by either their commonly known three letter symbols or by the one-letter symbols recommended by the IUPAC-IUB Biochemical Nomenclature Commission.

Further, the reconstituted RBM polypeptides of the invention may comprise 'equivalent amino acid residues'. This term refers to an amino acid residue capable of replacing another amino acid residue in a polypeptide without substantially altering the structure and/or functionality of the polypeptide. Equivalent amino acids thus have similar properties such as bulkiness of the side-chain, side chain polarity (polar or non-polar), hydrophobicity (hydrophobic or hydrophilic), pH (acidic, neutral or basic) and side chain organization of carbon molecules (aromatic/aliphatic). As such, equivalent amino acid residues can be regarded as conservative amino acid substitutions.

In the context of the present invention, within the meaning of the term 'equivalent amino acid substitution' as applied herein, is meant that in certain embodiments one amino acid may be substituted for another within the groups of amino acids indicated herein below:

i) Amino acids having polar side chains (Asp, GIu, Lys, Arg, His, Asn, GIn, Ser, Thr, Tyr, and Cys);

ii) Amino acids having non-polar side chains (GIy, Ala, VaI, Leu, lie, Phe, Trp, Pro, and Met);

iii) Amino acids having aliphatic side chains (GIy, Ala VaI, Leu, ile);

iv) Amino acids having cyclic side chains (Phe, Tyr, Trp, His, Pro);

v) Amino acids having aromatic side chains (Phe, Tyr, Trp);

vi) Amino acids having acidic side chains (Asp, GIu);

vii) Amino acids having basic side chains (Lys, Arg, His);
viii) Amino acids having amide side chains (Asn, GIn);
ix) Amino acids having hydroxy side chains (Ser, Thr);
x) Amino acids having sulphur-containing side chains (Cys, Met);
xi) Neutral, weakly hydrophobic amino acids (Pro, Ala, GIy, Ser, Thr);
xii) Hydrophilic, acidic amino acids (GIn, Asn, GIu, Asp), and
xiii) Hydrophobic amino acids (Leu, lie, VaI).

Still further, the reconstituted RBM polypeptide of the invention of the invention may have secondary modifications, such as phosphorylation, acetylation, glycosylation, sulfhydryl bond formation, cleavage and the likes, as long as said modifications retain the functional properties of the original protein, specifically, the ability to interact with the viral receptor and the neutralizing antibodies. Secondary modifications are often referred to in terms of relative position to certain amino acid residues. For example, a certain sequence positioned carboxyl-terminal to a reference sequence within a polypeptide is located proximal to the carboxyl terminus of the reference sequence, but is not necessarily at the carboxyl terminus of the complete polypeptide.

The invention further encompasses any derivatives, enantiomers, analogues, variants or homologues of any of the reconstituted RBM polypeptides disclosed herein. The term “derivative” is used to define amino acid sequences (polypeptide), with any insertions, deletions, substitutions and modifications to the amino acid sequences (polypeptide) that do not alter the activity of the original polypeptides. By the term “derivative” it is also referred to homologues, variants and analogues thereof, as well as covalent modifications of a polypeptides made according to the present invention. It should be noted that the reconstituted RBM polypeptides according to the invention can be produced either synthetically, or by recombinant DNA technology. Methods for producing polypeptides peptides are well known in the art.

In some embodiments, derivatives include, but are not limited to, polypeptides that differ in one or more amino acids in their overall sequence from the polypeptides defined herein, polypeptides that have deletions, substitutions, inversions or additions.

In some embodiments, derivatives refer to polypeptides, which differ from the polypeptides specifically defined in the present invention by insertions of amino acid residues. It should be appreciated that by the terms “insertions” or “deletions”, as used herein it is meant any addition or deletion, respectively, of amino acid residues to the polypeptides used by the invention, of between 1 to 50 amino acid residues, between 20 to 1 amino acid residues, and specifically, between 1 to 10 amino acid residues. More particularly, insertions or deletions may be of any one of 1, 2, 3, 4, 5, 6, 7, 8, 9, or 10 amino acids. It should be noted that the insertions or deletions encompassed by the invention may occur in any position of the modified peptide, as well as in any of the N' or C' termini thereof. It should be appreciated that in cases the deletion/s or insertion/s are in the N or C-terminus of the peptide, such derivatives may be also referred to as fragments.

The reconstituted RBM polypeptide of the invention of the invention may all be positively charged, negatively charged or neutral. In addition, they may be in the form of a dimer, a multimer or in a constrained conformation, which can be attained by internal bridges, short-range cyclizations, extension or other chemical modifications.

The polypeptides of the invention can be coupled (conjugated) through any of their residues to another peptide or agent. For example, the polypeptides of the invention can be coupled through their N-terminus to a lauryl-cysteine (LC) residue and/or through their C-terminus to a cysteine (C) residue.

Further, the reconstituted RBM polypeptide of the invention may be extended at the N-terminus and/or C-terminus thereof with various identical or different amino acid residues. As an example for such extension, the peptide may be extended at the N-terminus and/or C-terminus thereof with identical or different amino acid residue/s, which may be naturally occurring or synthetic amino acid residue/s. An additional example for such an extension may be provided by peptides extended both at the N-terminus and/or C-terminus thereof with a cysteine residue. Naturally, such an extension may lead to a constrained conformation due to Cys-Cys cyclization resulting from the formation of a disulfide bond. Another example may be the incorporation of an N-terminal lysyl-palmitoyl tail, the lysine serving as linker and the palmitic acid as a hydrophobic anchor. In addition, the peptides may be extended by aromatic amino acid residue/s, which may be naturally occurring or synthetic amino acid residue/s, for example, a specific aromatic amino acid residue may be tryptophan. The peptides may be extended at the N-terminus and/or C-terminus thereof with various identical or different organic moieties, which are not naturally occurring or synthetic amino acids. As an example for such extension, the reconstituted RBM polypeptide may be extended at the N-terminus and/or C-terminus thereof with an N-acetyl group.

For every single peptide sequence defined by the invention and disclosed herein, this invention includes the corresponding retro-inverse sequence wherein the direction of the peptide chain has been inverted and wherein all or part of the amino acids belong to the D-series. It should be understood that the present invention includes embodiments wherein one or more of the L-amino acids is replaced with its D isomer.

In yet some further embodiments, the reconstituted RBM polypeptide of the invention of the invention may comprise at least one amino acid residue in the D-form. It should be noted that every amino acid (except glycine) can occur in two isomeric forms, because of the possibility of forming two different enantiomers (stereoisomers) around the central carbon atom. By convention, these are called L- and D-forms, analogous to left-handed and right-handed configurations.

It should be appreciated that in some embodiments, the enantiomer or any derivatives of the reconstituted RBMs of the invention may exhibit at least one of enhanced activity, and superiority. In more specific embodiments, such derivatives and enantiomers may exhibit increased affinity to the nAbs or the viral receptor, enhanced stability, and increased resistance to proteolytic degradation.

The invention also encompasses any homologues of the polypeptides specifically defined by their amino acid sequence according to the invention. The term “homologues” is used to define amino acid sequences (polypeptide) which maintain a minimal homology to the amino acid sequences defined by the invention, e.g. preferably have at least about 65%, more preferably at least about 70%, at least about 75%, even more preferably at least about 80%, at least about 85%, most preferably at least about 90%, at least about 95% overall sequence homology with the amino acid sequence of any of the polypeptide as structurally defined above, e.g. of a specified sequence, more specifically, an amino acid sequence of the polypeptides as denoted by any one of SEQ ID NOs. 48, 50, 52, 54, 56, 58, 59, 60, 61, 62, 63, 64 and 89-110, and any derivatives, enantiomers and fusion proteins thereof.

More specifically, "Homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N-nor C-terminal extensions nor insertions or deletions shall be construed as reducing identity or homology. Methods and computer programs for the alignment are well known in the art.

In some embodiments, the present invention also encompasses polypeptides which are variants of, or analogues to, the polypeptides specifically defined in the invention by their amino acid sequence. With respect to amino acid sequences, one of skill will recognize that individual substitutions, deletions or additions to peptide, polypeptide, or protein sequence thereby altering, adding or deleting a single amino acid or a small percentage of amino acids in the encoded sequence is a "conservatively modified variant", where the alteration results in the substitution of an amino acid with a chemically similar amino acid.

Conservative substitution tables providing functionally similar amino acids are well known in the art and disclosed herein before. Such conservatively modified variants are in addition to and do not exclude polymorphic variants, interspecies homologues, and alleles and analogous peptides of the invention.

More specifically, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. As noted above, the peptides of the invention may be modified by omitting their N-terminal sequence. It should be appreciated that the invention further encompasses the omission of about 1, 2, 3, 4, 5, 6, 7, 8 and more amino acid residues from both, the N' and/or the C' termini of the peptides of the invention.

Certain commonly encountered amino acids which also provide useful substitutions include, but are not limited to, β-alanine (β-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGIy); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (NIe); naphthylalanine (NaI); 4-chlorophenylalanine (Phe(4-C1)); 2-fluorophenyl alanine (Phe(2-F)); 3-fluorophenylalanine (Phe(3-F)); 4-fluorophenylalanine (Phe(4-F)); penicillamine (Pen); 1,2, 3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,4-diaminobutyric acid (Dab); p-aminophenylalanine (Phe(pNH.sub.2)); N-methyl valine (MeVaI); homocysteine (hCys), homophenylalanine (hPhe) and homoserine (hSer); hydroxyproline (Hyp), homoproline (hPro), N-methylated amino acids (e.g., N-substituted glycine). Covalent Modifications of Amino Acids and the Peptide Covalent modifications of the peptide are included and may be introduced by reacting targeted amino acid residues of the peptide with an organic derivatizing agent that is capable of reacting with selected side chains or terminal residues.

Cysteinyl residues most commonly are reacted with α-haloacetates (and corresponding amines) to give carboxymethyl or carboxyamidomethyl derivatives. Cysteinyl residues also are derivatized by reaction with bromotrifluoroacetone, α-bromo-O-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1, 3-diazole. Histidyl residues are derivatized by reaction with diethylprocarbonate (pH 5.5-7.0) which agent is relatively specific for the histidyl side chain. Bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents reverses the charge of the lysinyl residues. Other suitable reagents for derivatizing α-amino-containing residues include imidoesters such as methylpicolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, including phenylglyoxal, 2,3-butanedione, 1,2-cyclohexanedione, and ninhydrin. Such derivatization requires that the reaction be performed in alkaline conditions because of the high pKa of the guanidine functional group. Furthermore, these reagents may react with the groups of lysine as well as the arginine ε-amino group.

Modification of tyrosyl residues has permits introduction of spectral labels into a peptide. This is accomplished by reaction with aromatic diazonium compounds or tetranitromethane. Most commonly, N-acetylimidizol and tetranitromethane are used to create 0-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Aspartyl and glutamyl residues are converted to asparaginyl and glutaminyl residues by reaction with ammonium ions. Conversely, glutaminyl and asparaginyl residues may be deamidated to the corresponding glutamyl and aspartyl residues. Deamidation can be performed under mildly acidic conditions. Either form of these residues falls within the scope of this invention.

Derivatization with bifunctional agents is useful for cross-linking the peptide to a water-insoluble support matrix or other macromolecular carrier. Commonly used cross-linking agents include 1,1-bis(diazoacetyl)-2-phenylethane, glutaraldehyde, N-hydroxysuccinimide esters, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light.

Other chemical modifications include hydroxylation of proline and lysine, phosphorylation of the hydroxyl groups of seryl or threonyl residues, methylation of the α-amino groups of lysine, arginine, and histidine side chains (Creighton, supra), acetylation of the N-terminal amine, and, in some instances, amidation of the C-terminal carboxyl.

Such chemically modified and derivatized moieties may improve the peptide's solubility, absorption, biological half-life, and the like. These changes may eliminate or attenuate undesirable side effects of the proteins in vivo. Adjuvants, Immune Stimulants and Immunogen Formulations It should be appreciated that the invention further encompass any of the peptides of the invention referred herein, any serogates thereof, any salt, base, ester or amide thereof, any enantiomer, stereoisomer or disterioisomer thereof, or any combination or mixture thereof. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts.

The present invention encompasses any fragment, derivative or analogue of any of the reconstituted RBM polypeptides of the invention. In certain embodiments, any of the polypeptides of the invention and derivatives thereof can bind the viral receptor as well as neutralizing antibodies (nAb/s), and more importantly, possess the ability to elicit the production of neutralizing antibodies in a subject vaccinated by the polypeptides of the invention. Thus, in some embodiments a "functional" reconstituted RBM polypeptide of the invention is a peptide possessing the ability to elicit the production of neutralizing antibodies, and/or inducing immunity against the infecting CoV/In certain embodiments, the reconstituted RBMs of the invention may be fused to additional peptide sequences. The invention further encompasses any fusion protein comprising the reconstituted RBMs of the invention as described herein. More specifically, additional peptide sequences can be added to the polypeptides (reconstituted RBMs) of the invention thereby forming fusion proteins, which act to promote stability, purification, and/or detection. For example, a reporter peptide portion (e.g., green fluorescent protein (GFP), β-galactosidase, or a detectable domain thereof) can be used. Purification-facilitating peptide sequences include those derived or obtained from maltose binding protein (MBP), glutathione-S-transferase (GST), or thioredoxin (TRX).

Still further, in certain embodiments, the invention further encompasses any nucleic acid sequence encoding any of the reconstituted RBM polypeptides described herein, as well as any expression vector comprising said encoding nucleic acid sequence, or any host cell expressing the same. As used herein, the term 'polynucleotide' or a 'nucleic acid sequence' refers to a polymer of nucleic acids, such as deoxyribonucleic acid (DNA) or ribonucleic acid (RNA). As used herein, 'nucleic acid' (also or nucleic acid molecule or nucleotide) refers to any DNA or RNA polynucleotides, oligonucleotides, fragments generated by the polymerase chain reaction (PCR) and fragments generated by any of ligation, scission, endonuclease action, and exonuclease action, either single- or double-stranded. Nucleic acid molecules can be composed of monomers that are naturally-occurring nucleotides (such as DNA and RNA), or analogs of naturally-occurring nucleotides (e.g., alpha-enantiomeric forms of naturally-occurring nucleotides), or modified nucleotides or any combination thereof. Herein this term also encompasses a cDNA, i.e. complementary or copy DNA produced from an RNA template by the action of reverse transcriptase (RNA-dependent DNA polymerase).

In this connection an 'isolated polynucleotide' is a nucleic acid molecule that is separated from the genome of an organism. For example, a DNA molecule that encodes any of the reconstituted RBM polypeptides of the invention or any derivative, variant, fragment or fusion protein thereof that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species. The invention further relates to recombinant DNA constructs comprising the polynucleotides of the invention or variants, homologues or derivatives thereof. The constructs of the invention may further comprise additional elements such as promoters, regulatory and control elements, translation, expression and other signals, operably linked to the nucleic acid sequence of the invention. As used herein, the term "recombinant DNA" or "recombinant gene" refers to a nucleic acid comprising an open reading frame encoding one of the proteins of the invention.

Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. Generally, the genetic control elements can include a prokaryotic promoter system or a eukaryotic promoter expression control system. This typically includes a transcriptional promoter, an optional operator to control the onset of transcription, transcription enhancers to elevate the level of RNA expression, a sequence that encodes a suitable ribosome binding site, RNA splice junctions, sequences that terminate transcription and translation and so forth. Expression vectors usually contain an origin of replication that allows the vector to replicate independently of the host cell.

Accordingly, the term control and regulatory elements includes promoters, terminators and other expression control elements. For instance, any of a wide variety of expression control sequences that control the expression of a DNA sequence when operatively linked to it may be used in these vectors to express DNA sequences encoding any desired protein using the method of this invention. A vector may additionally include appropriate restriction sites, antibiotic resistance or other markers for selection of vector-containing cells. Plasmids are the most commonly used form of vector but other forms of vectors which serve an equivalent function and which are, or become, known in the art are suitable for use herein.

In yet a second aspect, the invention relates to a composition comprising an effective amount of at least one polypeptide comprising an amino acid sequence of at least one reconstituted RBM of a viral Spike protein, specifically, CoV Spike protein or any fragments thereof, any derivative, enantiomer, fusion protein, conjugate or polyvalent dendrimer thereof. More specifically, the reconstituted RBM of the invention may comprise at least one linker and at least one fragment of the native RBM. In some specific embodiments, the native RBM is a 30 to 200 amino acid sequence comprised within the RBD of said Spike protein forming a binding interface that interacts with the viral receptor. In more particular embodiments, the native RBM may be an extended 30 to 100 or more amino acid excursion, juxtaposed along the edge of the core of the RBD and tacked to the core via a tacking segment. More specifically, the reconstituted RBM may comprise at least one exogenous linker. In some embodiments, at least one of linker/s replace or may be added to at least one of: the tacking segment, any part or amino acid residue thereof and any RBM fragment or amino acid residue/s not directly involved in receptor and/or nAb/s binding, and RBM residues directly or indirectly involved in receptor and/or nAb/s binding. The composition of the invention may optionally further comprises at least one pharmaceutically acceptable carrier/s, excipient/s, auxiliaries, and/or diluent/s.

In certain embodiments, the composition of the invention may comprise a polypeptide comprising any of the reconstituted RBMs defined by the invention.

The term "pharmaceutical composition" in the context of the invention means that the composition is of a grade and purity suitable for prophylactic or therapeutic administration to human subjects and is present together with at least one of carrier/s, diluent/s, excipient/s and/or additive/s that are pharmaceutically acceptable. The pharmaceutical composition may be suitable for any mode of administration whether oral or parenteral, by injection or by topical administration by inhalation, intranasal spray or intraocular drops. More specifically, pulmonary, oral, transmucosal, intestinal or parenteral delivery, including intramuscular, subcutaneous and intramedullary injections as well as rectal, intrathecal, direct intraventricular, intravenous, intraocular injections or any other medically acceptable methods of administration may be considered as appropriate administration mode for the compositions of the invention.

Pharmaceutical compositions according to the invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general formulations are prepared by uniformly and intimately bringing into association the active ingredients with liquid carriers or finely divided solid carriers or both, and then, if necessary, shaping the product. The compositions may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome-containing formulations.

It should be understood that in addition to the ingredients particularly mentioned above, the formulations may also include other agents conventional in the art having regard to the type of formulation in question, for example those suitable for oral administration may include flavoring agents.

As noted above, any of the compositions of the invention may comprise pharmaceutically acceptable carriers, vehicles, adjuvants, excipients, or diluents. As used herein pharmaceutically acceptable carriers, vehicles, adjuvants, excipients, or diluents, are well-known to those skilled in the art and are readily available to the public. It is preferred that the pharmaceutically acceptable carrier be one which is chemically inert to the active compounds and one which has no detrimental side effects or toxicity under the conditions of use.

The choice of a carrier will be determined in part by the particular active agent, as well as by the particular method used to administer the composition. The carrier can be a solvent or a dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. Each carrier should be both pharmaceutically and physiologically acceptable in the sense of being compatible with the other ingredients and not injurious to the subject. Formulations include those suitable for immersion, oral, parenteral (including subcutaneous, intramuscular, intravenous, intraperitoneal, implantation for slow release and intradermal) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

In yet some further embodiments, the composition of the invention may be an immunogenic composition. Thus, in some embodiments, the immunogenic composition of the invention may induce an immune response in a subject. "Immune response" as used herein means the activation of a host's immune system, e.g., that of a mammal, in response to the introduction of antigen. The immune response can be in the form of a cellular or humoral response, or both.

Still further aspect of the invention relates to an epitope based CoV vaccine comprising at least one polypeptide comprising an amino acid sequence of at least one reconstituted RBM of a viral Spike protein, specifically, CoV spike protein, more specifically, 51 protein, or of any fragment thereof, any derivative, enantiomer, fusion protein, conjugate or polyvalent dendrimer thereof. More specifically, the reconstituted RBM of the invention may comprise at least one linker and at least one fragment of the native RBM. In some specific embodiments, the native RBM is a 30 to 200 amino acid sequence comprised within the RBD of said Spike protein forming a binding interface that interacts with the viral receptor. The native RBM may be an extended 30 to 100 or more amino acid excursion, juxtaposed along the edge of the core of the RBD and tacked to the core via a tacking segment. In some specific embodiments the reconstituted RBM of the vaccine of the invention may comprise at least one exogenous linker. It should be noted that at least one of the linker/s may replace at least one of: the tacking segment, any part or amino acid residue thereof, any RBM fragment or amino acid residue/s not directly involved in receptor binding or any RBM fragment or amino acid residue directly or indirectly involved in said binding. In more specific embodiments, the vaccine of the invention optionally further comprises at least one pharmaceutically acceptable carrier/s, excipient/s, auxiliaries, and/or diluent/s.

In some embodiments, the vaccine provided by the invention may comprise at least one polypeptide comprising any of the reconstituted RBM as defined by the invention and described herein above.

Provided herein are immunogenic compositions, such as vaccines, comprising at least one of reconstituted RBM polypeptide, specifically, reconstituted CoV RBMs, more specifically, reconstituted RBMs of MERS-CoV and SARS-CoV, any fragment, derivative, enantiomer, variant, conjugate and fusion protein thereof, or a combination thereof. The vaccine can be used to protect against any number of strains of CoVs, specifically, any strains of MERS-CoV or any strains or variants of SARS-CoV, thereby treating, preventing, and/or protecting against MERS-CoV or SARS-CoV associated pathologies. The vaccine can significantly induce an immune response of a subject administered the vaccine, thereby protecting against and treating CoVs infections, specifically, MERS-CoV or SARS-CoV infections.

Still further, when provided prophylactically, the reconstituted RBMs of the invention or any derivative, enantiomer, fusion protein or conjugate thereof, may be provided in advance of the CoV infection, specifically, MERS-CoV or SARS-CoV infection, such as to patients or subjects who are at risk for being exposed to MERS-CoV or SARS-CoV or who have been newly exposed to MERS-CoV or SARS-CoV, such as healthcare workers, blood products, or transplantation tissue, and other individuals who have been exposed to a body fluid that contains or may contain MERS-CoV or SARS-CoV. The prophylactic administration of the reconstituted RBMs of the invention or any derivative, enantiomer, fusion protein or conjugate thereof prevents, ameliorates, or delays MERS-CoV or SARS-CoV infection. In subjects who have been newly exposed to MERS-CoV or SARS-CoV but who have not yet displayed the presence of the virus (as measured by PCR or other assays for detecting the virus) in blood or other body fluid, efficacious treatment with the reconstituted RBMs of the invention or any derivative, enantiomer, fusion protein or conjugate thereof partially or completely inhibits or delays the appearance of the virus or minimizes the level of the virus in the blood or other body fluid of the exposed individual.

The efficacy of the reconstituted RBMs of the invention or any derivative, enantiomer, fusion protein or conjugate thereof, can be assessed in various ways well known to the skilled practitioner. For instance, one of ordinary skill in the art will understand that vaccine of the invention is efficacious in treating or inhibiting a MERS-CoV or SARS-CoV infection in a subject by observing that the neutralizing antibodies induced thereby reduce viral load or delays or prevents a further increase in viral load. Viral loads can be measured by methods that are known in the art, for example, using PCR assays to detect the presence of MERS-CoV or SARS-CoV nucleic acid or antibody assays to detect the presence of MERS-CoV protein in a sample (e.g., blood or another body fluid) from a subject or patient, or by measuring the level of circulating anti-MERS-CoV or anti-SARS-CoV antibodies in the patient.

In some embodiments, the vaccine may induce a humoral immune response in the subject administered the vaccine or the immunogenic composition. In some embodiments, the induced humoral immune response may be specific for the specific CoV, specifically, MERS-CoV or SARS-CoV. The humoral immune response may be induced in the subject administered the vaccine by about 1.5-fold to about 100-fold, about 2-fold to about 90-fold, or about 3-fold to about 80-fold. The humoral immune response can be induced in the subject administered the vaccine by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 20-fold, at least about 30-fold, at least about 40-fold, at least about 50-fold, at least about 60-fold, at least about 70-fold, at least about 80-fold, at least about 90-fold, at least about 100-fold, or more.

The humoral immune response induced by the vaccine may include an increased level of neutralizing antibodies associated with the subject administered the vaccine as compared to a subject not administered the vaccine. The neutralizing antibodies may be specific for the MERS-CoV or SARS-CoV, specifically, for the reconstituted RBMs of the invention. The neutralizing antibodies can provide protection against and/or treatment of MERS-CoV or SARS-CoV infection and its associated pathologies in the subject administered the vaccine.

The humoral immune response induced by the vaccine may include an increased level of IgG antibodies associated with the subject administered the vaccine as compared to a subject not administered the vaccine.

The humoral response may be cross-reactive against two or more strains of the particular CoV, specifically, two or more strains of the MERS-CoV or two or more strains of the SARS-CoV. The level of IgG antibody associated with the subject administered the vaccine may be increased by about 1.5-fold to about 100-fold, about 2-fold to about 50-fold, or about 3-fold to about 25-fold as compared to the subject not administered the vaccine. The level of IgG antibody associated with the subject administered the vaccine can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 20-fold, at least about 30-fold, at least about 40-fold, at least about 50-fold, at least about 60-fold, at least about 70-fold, at least about 80-fold, at least about 90-fold, at least about 100-fold, or more.

In yet some further embodiments, the vaccine can induce a cellular immune response in the vaccinated subject, such response may be specific for the reconstituted RBMs of the invention. The induced cellular immune response may include eliciting a $CD8^+$ T cell response, that may according to certain embodiments, include the production of cytokines such as interferon-gamma (IFN-γ), tumor necrosis factor alpha (TNF-alpha), interleukin-2 (IL-2), or any combinations thereof.

In yet some further embodiments, the cellular immune response induced by the vaccine can include eliciting a $CD4^+$T cell response. In some embodiments, the $CD4^+$ T cells may produce IFN-γ, TNF-α, IL-2, or a combination of IFN-γ and TNF-α.

The vaccine may further induce an immune response when administered to different tissues such as the muscle or skin. The vaccine can further induce an immune response when administered via electroporation, or injection, or subcutaneously, or intramuscularly.

Also provided herein are methods of treating, protecting against, and/or preventing disease in a subject in need thereof by administering the vaccine to the subject.

Administration of the vaccine to the subject may induce or elicit an immune response in the subject. The induced immune response can be used to treat, prevent, and/or protect against disease, for example, pathologies relating to CoV infections, specifically, MERS-CoV or SARS-CoV infection. The induced immune response provided the subject administered the vaccine resistance to one or more MERS-CoV strains or to one or more or SARS-CoV strains.

The vaccine dose may range between 0.001 µs to 100 mg active ingredient, specifically, the reconstituted RBMs of the invention/kg body weight/time, and in some embodiments may be 0.01 µg to 100 mg reconstituted RBM/kg body weight/time. The vaccine may be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment may be 1, 2, 3, 4, 5, 6, 7, 8, 9, 10, or more.

The vaccine may be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a camel or any other camelids, such as the llama, alpaca, guanaco, and vicuña of South America, a horse, a cow, a pig, a sheep, a cat, a dog, a rat, or a mouse.

In yet some further embodiments, the subject may be an avian subject, specifically, wild or domestic birds. It should be noted that the vaccine can be administered prophylactically or therapeutically. In prophylactic administration, the vaccines may be administered in an amount sufficient to induce an immune response. In therapeutic applications, the vaccines are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The reconstituted RBM polypeptide of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the reconstituted RBM polypeptide.

The vaccine can be delivered via a variety of routes. Typical delivery routes include parenteral administration, e.g., intradermal, intramuscular or subcutaneous delivery. Other routes include oral administration, intranasal, intravaginal and mucosal administration (such as intranasal, oral, intratracheal, and ocular).

The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant.

The vaccine can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine The vaccine can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine can be incorporated into liposomes, microspheres or other polymer matrices. Liposomes can consist of phospholipids or other lipids, and can be nontoxic, physiologically acceptable and metabolizable carriers that are relatively simple to make and administer.

Vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

Mucosal vaccines may be, for example, liquid dosage forms, such as pharmaceutically acceptable emulsions, solutions, suspensions, syrups, and elixirs. Excipients suitable for such vaccines include, for example, inert diluents commonly used in the art, such as, water, saline, dextrose, glycerol, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol. Excipients also can comprise various wetting, emulsifying, suspending, flavoring (e.g., sweetening), and/or perfuming agents.

Oral mucosal vaccines also may, for example, be tableted or encapsulated for convenient administration. Such capsules or tablets can contain a controlled-release formulation. In the case of capsules, tablets, and pills, the dosage forms also can comprise buffering agents, such as sodium citrate, or magnesium or calcium carbonate or bicarbonate.

Tablets and pills additionally can be prepared with enteric coatings.

It is contemplated that the vaccine may be administered via the human, camel or avian patient's drinking water and/or food.

"Parenteral administration" that is also contemplated by the invention includes subcutaneous injections, submucosal injections, intravenous injections, intramuscular injections, intrasternal injections, transcutaneous injections, and infusion. Injectable preparations (e.g., sterile injectable aqueous or oleaginous suspensions) can be formulated according to the known art using suitable excipients, such as vehicles, solvents, dispersing, wetting agents, emulsifying agents, and/or suspending agents. These typically include, for example, water, saline, dextrose, glycerol, ethanol, corn oil, cottonseed oil, peanut oil, sesame oil, benzyl alcohol, benzyl alcohol, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), propylene glycol, and/or polyethylene glycols. Excipients also may include small amounts of other auxiliary substances, such as pH buffering agents.

The vaccine may include one or more excipients that enhance the vaccinated patient's immune response (which may include an antibody response, cellular response, or both), thereby increasing the effectiveness of the vaccine. The adjuvant(s) may be a substance that has a direct (e.g., cytokine or Bacille Calmette-Guerin ("BCG")) or indirect effect (liposomes) on cells of the canine patient's immune system. Examples of often suitable adjuvants include oils (e.g., mineral oils), metallic salts (e.g., aluminum hydroxide or aluminum phosphate), bacterial components (e.g., bacterial liposaccharides, Freund's adjuvants, and/or MDP), plant components (e.g., Quil A), and/or one or more substances that have a carrier effect (e.g., bentonite, latex particles, liposomes, and/or Quil A, ISCOM). As noted above, adjuvants also include, for example, CARBIGEN™ and carbopol. It should be recognized that this invention encompasses both vaccines that comprise an adjuvant(s), as well as vaccines that do not comprise any adjuvant.

It is contemplated that the vaccine may be freeze-dried (or otherwise reduced in liquid volume) for storage, and then reconstituted in a liquid before or at the time of administration. Such reconstitution may be achieved using, for example, vaccine-grade water.

It is another purpose of the present invention to combat CoVs infections in animals, particularly those relevant for infections in humans. Those relevant to SARS-CoV include monkeys, Himalayan palm civets, raccoon dogs, cats, dogs, and rodents. For MERS-CoV those include camels and bats. Further, CoVs also cause a range of diseases in farm animals and domesticated pets, some of which can be serious and are a threat to the farming industry. Economically significant CoVs of farm animals include porcine CoV (transmissible gastroenteritis CoV, TGE) and bovine CoV, which both result in diarrhea in young animals. Feline CoVs include two forms. Spontaneous mutations in feline enteric CoVs can result in feline infectious peritonitis (FIP)—a disease associated with high mortality. Similarly, there are two types of CoVs that infect ferrets. Ferret enteric CoV causes a gastrointestinal syndrome known as epizootic catarrhal enteritis (ECE), and a more lethal systemic version of the virus (like FIP in cats) known in ferrets as ferret systemic coronavirus (FSC). There are two types of canine CoV (CCoVs), one that causes mild gastrointestinal disease and one that has been found to cause respiratory disease. Mouse hepatitis virus (MHV) is a coronavirus that causes an epidemic murine illness with high mortality, especially among colonies of laboratory mice. In chickens, the infectious bronchitis virus (IBV), a CoV, targets not only the respiratory tract but also the uro-genital tract, and can spread to other organs. The vaccine of the invention as well as any of the compositions and methods described herein may be applicable for any of the disorders mentioned herein.

As noted herein before, the inventive concept behind the present invention is based on deep understanding of the unique structural/functional properties of the viral S1 protein and its components. This term herein refers to one of the functional subunits of the CoV Spike glycoprotein, a class I viral fusion protein that forms the characteristic spikes, or peplomers, found on the viral surface that mediate virus attachment, fusion, and entry into the host cell, and thereby determines the tropism of the virus. During virus maturation, Spike glycoprotein is cleaved into two subunits: S1, which binds to receptors in the host cell, and S2, which mediates membrane fusion. In other words, herein this term refers to a CoV protein referred to by terms Coronavirus Spike Glycoprotein, Spike Protein, Spike Glycoproteins 51, Spike Gp 51, or term under MeSH Unique ID: D064370.

In some embodiments, this term refers to the SARS CoV 51 glycoprotein referred to by SARS coronavirus Shanghai-QXCl 51, GenBank Protein Accession: AAR86788.1, accession AY463059.1. In more specific embodiments, the SARS 51 comprises an amino acid sequence as denoted by SEQ ID NO: 31. In this connection, the invention further refers to the RBD as denoted by SEQ ID NO: 32, 33 or alternatively, SEQ ID NO: 85.

Different putative S1 sequences from SARS-CoV isolates can be obtained from NCBI. It should be therefore appreciated that in certain embodiments, each of these S1 proteins is encompassed by the invention.

Table 1 lists GenBank accession numbers for 102 S gene sequences of SARS-CoVs

TABLE 1

| Epidemic phases | | Strains | Accession | Epidemic | Strains | Accession |
|---|---|---|---|---|---|---|
| 02-04 | 02-03 | SZ1 | AY304489 | 03-late | GZ-B | AY394978 |
| | | SZ3 | AY304486 | | GZ-C | AY394979 |
| interspecies | phase | SZ13 | AY304487 | epidemic | TOR2 | AY274119 |
| | | SZ16 | AY304488 | group | URBANI | AY278741 |
| epidemic | | | | | WHU | AY394850 |
| group | 03-04 | PC4-13 | AY613948 | (56 sequences) | HKU-39849 | AY278491 |
| | | PC4-115 | AY627044 | | CUHK-SU10 | AY282752 |
| | phase | PC4-127 | AY613951 | | CUHK-LC2 | AY394999 |
| (17 sequences) | | PC4-136 | AY613949 | | CUHK-LC4 | AY395001 |
| | | PC4-137 | AY627045 | | FRANKFURT | AY291315 |
| | | PC4-145 | AY627046 | | TW3 | AY502926 |
| | | PC4-199 | AY627047 | | TW8 | AY502931 |
| | | PC4-205 | AY613952 | | TW10 | AY502923 |
| | | PC4-227 | AY613950 | | TW11 | AY502924 |
| | | PC4-241 | AY627048 | | TWH | AP006557 |

TABLE 1-continued

| Epidemic phases | Strains | Accession | Epidemic | Strains | Accession |
|---|---|---|---|---|---|
| | GD03T13 | AY525636 | | TWK | AP006559 |
| | GZ03-01 | AY568539 | | TWS | AP006560 |
| | GZ03-02 | AY613947 | | Sino1-11 | AY485277 |
| 03-early-mid epidemic | GZ02 | AY390556 | | Sino3-11 | AY485278 |
| group | HGZ8L1-A | AY394981 | | Sin845 | AY559093 |
| (27 sequences) | ZS-A | AY394997 | | Sin849 | AY559086 |
| | ZS-B | AY394996 | | Sin850 | AY559096 |
| | ZS-C | AY395003 | | Sin852 | AY559082 |
| | HSZ-Bb | AY394985 | | SIN2677 | AY283795 |
| | HSZ-Bc | AY394994 | | SIN2748 | AY283797 |
| | HSZ-Cb | AY394986 | | Sin3765V | AY559084 |
| | HSZ-Cc | AY394995 | | TC1 | AY338174 |
| | HGZ8L1-B | AY394982 | | TC2 | AY338175 |
| | GZ50 | AY304495 | | TC3 | AY348314 |
| | GZ-A | AY394977 | | AS | AY427439 |
| | JMD | AY394988 | | A11S | AY345986 |
| | BJ01 | AY278488 | | A7N | AY345987 |
| | BJ02 | AY278487 | | STL2 | AY345988 |
| | BJ03 | AY278490 | | TW1 | AY291451 |
| | BJ04 | AY279354 | | TW2 | AY502925 |
| | CUHK-W1 | AY278554 | | TW4 | AY502927 |
| | HZS2-A | AY394983 | | TW5 | AY502928 |
| | HZS2-Bb | AY395004 | | TW6 | AY502929 |
| | HZS2-C | AY394992 | | TW7 | AY502930 |
| | HZS2-D | AY394989 | | TW9 | AY502932 |
| | HZS2-E | AY394990 | | TWC | AY321118 |
| | HZS2-Fb | AY394987 | | TWJ | AP006558 |
| | HZS2-Fc | AY394991 | | TWY | AO996561 |
| | HCZ8L-2 | AY394993 | | GD69 | AY313906 |
| | NS-1 | AY508724 | | HSR | AY323977 |
| | | | | Sin847 | AY559095 |
| | | | | Sin848 | AY559085 |
| Outgroup | B24 | DQ022305 | | SIN2774 | AY283798 |
| (2 sequences) | B41 | DQ084199 | | SIN2500 | AY283794 |
| | | | | PUMC01 | AY350750 |
| | | | | PUMC02 | AY357075 |
| | | | | PUMCO3 | AY357076 |
| | | | | SIN2679 | AY283796 |
| | | | | CUHK-LC1 | AY394998 |
| | | | | CUHK-LC3 | AY395000 |
| | | | | CUHK-LC5 | AY395002 |

In yet some other embodiments, the term S1 protein refers to the MERS CoV S1 glycoprotein referred to by GenBank: AHX00731.1 GI:612348173, Locus AHX00731. In more specific embodiments, the MERS S1 comprises an amino acid sequence as denoted by SEQ ID NO: 34. In this connection, the invention further refers to the RBD as denoted by SEQ ID NO: 35 or alternatively, SEQ ID NO: 36, SEQ ID NO: 81 (residues 381-588) or SEQ ID NO: 82 (residues 367-606).

Further, the present invention pertains to a specific region within the Spike Gp S1, specifically the Receptor Binding Domain (RBD), and more specifically the Receptor Binding Motif (RBM), as being responsible for the S1 bi-functional properties, namely host receptor binding and host immunity receptors. In the case of SARS CoV, it has been demonstrated that the infection is mediated through the interaction of the viral Spike protein (1255 amino acids) and its cellular receptor Angiotensin-Converting Enzyme 2 (ACE2). The SARS CoV RBD (amino acids N318-T509 of S protein, denoted by SEQ ID NO: 87) harbors an extended excursion that contacts ACE2, which is RBM (amino acids 5432-T486, denoted by SEQ ID NO: 3). It has been further demonstrated that RBM is a major antigenic determinant able to elicit production of neutralizing antibodies. Hence, the role of the RBM is a bi-functional bioactive surface that can be demonstrated by antibodies such as the neutralizing human anti-SARS monoclonal antibody (mAb) 80R which targets the RBM and competes with the ACE2 receptor for binding.

A further aspect of the invention provides a method for preventing, inhibiting, reducing, eliminating, protecting or delaying the onset of an infection or an infectious clinical condition caused by coronavirus in a subject in need thereof. More specifically, the method comprising the step of administrating to the subject an effective amount of at least one polypeptide comprising an amino acid sequence of at least one reconstituted RBM of CoV Spike protein, or of any fragment thereof, any derivative, enantiomer, fusion protein, conjugate or polyvalent dendrimer thereof or of any composition or vaccine comprising the same. In some embodiments, the reconstituted RBM of the invention may comprise at least one linker and at least one fragment of the native RBM. In further specific embodiments, the native RBM is a 30 to 200 amino acid sequence comprised within the RBD of said Spike protein forming a binding interface that interacts with the viral receptor. In certain specific embodiments, the RBM is an extended 30 to 100 or more amino acid excursion, juxtaposed along the edge of the core of the RBD and tacked to the core via a tacking segment. In certain embodiments, the reconstituted RBM comprises at least one exogenous linker. It should be noted that in certain embodiments, at least one of said linker/s replaces at least one of the tacking segment, any part or amino residue/s thereof, any RBM fragment or amino acid residue/s not directly involved in receptor and/or nAb/s binding and any RBM fragment or amino acid residue/s directly or indirectly involved in receptor and/or nAb/s binding.

In more specific embodiments, any of the polypeptides of the invention that comprise any of the reconstituted RBM polypeptides defined by the invention, or any compositions or vaccines thereof, may be used by the method of the invention.

Of particular interest are any of the MERS-CoV reconstituted RBM polypeptides, specifically, any of the polypeptides comprising the amino acid sequence of SEQ ID NO: 48, 50, 52, 54, 56, 58, 59, 60, 61, 62, 63, and 64. In yet some further embodiments any of the SARS-CoV polypeptides of the invention, specifically, and of the polypeptides comprising the sequences denoted by SEQ ID NO: 89-110, may be used in the immunogenic compositions and the vaccines of the invention.

It should be noted that the invention further encompasses methods for treating and preventing infectious disease caused by viral pathogens, specifically, CoVs such as MERS-CoV or SARS-CoV. More specifically, MERS CoV associated disorders include but are not limited to respiratory illness (in particular severe acute respiratory illness) with symptoms of fever, cough, and/or shortness of breath. Pneumonia is a common finding on examination. Severe disease from MERS-CoV infection can cause respiratory failure that requires mechanical ventilation and support in an intensive-care unit. Gastrointestinal symptoms, including diarrhea, nausea/vomiting have also been reported. Symptoms also include organ failure, especially of the kidneys, or septic shock. The virus appears to cause more severe disease in older people, in people with weakened immune systems, and in people with background illnesses or chronic diseases as for example diabetes, cancer and chronic lung disease. SARS CoV associated disorders or conditions include high fever (temperature greater than 100.4° F. or 38.0° C.), headache, mild respiratory symptoms, diarrhea, dry cough and develop pneumonia. The term "treatment" in accordance with disorders associated with infectious conditions may refer to one or more of the following: elimination, reducing or decreasing the intensity or frequency of disorders associated with said infectious condition. The treatment may be undertaken when disorders associated with said infection, incidence is beginning or may be a continuous administration, for example by administration every 1 to 14 days, to prevent or decrease occurrence of infectious condition in an individual prone to said condition. Such individual may be for example a subject having a compromised immune-system, in case of cancer patients undergoing chemotherapy or HIV infected subjects. Thus, the term "treatment" is also meant as prophylactic or ameliorating treatment.

The term "prophylaxis" refers to prevention or reduction the risk of occurrence of the biological or medical event, specifically, the occurrence or re occurrence of disorders associated with infectious disease, that is sought to be prevented in a tissue, a system, animal or human by a researcher, veterinarian, medical doctor or other clinician, and the term "prophylactically effective amount" is intended to mean that amount of a pharmaceutical composition that will achieve this goal. Thus, in particular embodiments, the methods of the invention are particularly effective in the prophylaxis, i.e., prevention of conditions associated with infectious viral disease. Thus, subjects administered with said compositions are less likely to experience symptoms associated with said infectious condition that are also less likely to re-occur in a subject who has already experienced them in the past.

The term "amelioration" as referred to herein, relates to a decrease in the symptoms, and improvement in a subject's condition brought about by the compositions and methods according to the invention, wherein said improvement may be manifested in the forms of inhibition of pathologic processes associated with any infectious viral disease, a significant reduction in their magnitude, or an improvement in a diseased subject physiological state.

The term "inhibit" and all variations of this term is intended to encompass the restriction or prohibition of the progress and exacerbation of pathologic symptoms or a pathologic process progress, said pathologic process symptoms or process are associated with.

The term "eliminate" relates to the substantial eradication or removal of the pathologic symptoms and possibly pathologic etiology, optionally, according to the methods of the invention described herein.

The terms "delay", "delaying the onset", "retard" and all variations thereof are intended to encompass the slowing of the progress and/or exacerbation of an infectious disease, specifically, of CoV infection and their symptoms slowing their progress, further exacerbation or development, so as to appear later than in the absence of the treatment according to the invention.

As used herein, "disease", "disorder", "condition" and the like, as they relate to a subject's health, are used interchangeably and have meanings ascribed to each and all of such terms.

The present invention relates to the treatment of subjects, or patients, in need thereof. By "patient" or "subject in need" it is meant any organism who may be affected by the above-mentioned conditions, and to whom the vaccinating and treatment methods herein described is desired, including humans, domestic and non-domestic mammals such as canine and feline subjects, bovine, simian, equine and murine subjects, rodents, domestic or wild birds, aquaculture, fish and exotic aquarium fish. It should be appreciated that the treated subject may be also any reptile or zoo animal. More specifically, the composition/s and method/s of the invention are intended for mammals or avian subjects. By "mammalian subject" is meant any mammal for which the proposed therapy is desired, including human, camelids, bats, equine, canine, and feline subjects, most specifically humans. It should be noted that specifically in cases of non-human subjects, the method of the invention may be performed using administration via injection, drinking water, feed, spraying, oral gavage and directly into the digestive tract of subjects in need thereof.

Single or multiple administrations of the compositions or vaccines of the invention are administered depending on the dosage and frequency as required and tolerated by the patient. In any event, the composition should provide a sufficient quantity of the reconstituted RBMs of the invention to effectively vaccinate and thereby treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Still further, the reconstituted RBMs of the invention or any compositions or kits thereof may be applied as a single daily dose or multiple daily doses, preferably, every 1 to 7 days. It is specifically contemplated that such application may be carried out once, twice, thrice, four times, five times or six times daily, or may be performed once daily, once every 2 days, once every 3 days, once every 4 days, once every 5 days, once every 6 days, once every week, two weeks, three weeks, four weeks or even a month.

The application of the reconstituted RBMs of the invention or any compositions or kits thereof may last up to a day, two days, three days, four days, five days, six days, a week, two weeks, three weeks, four weeks, a month, two months three months or even more. Specifically, application may last from one day to one month. Most specifically, application may last from one day to 7 days. The invention thus provides methods for inhibiting and preventing viral infection, specifically, CoV infections in a subject. It should be appreciated that such method may results in an inhibition, reduction, elimination, attenuation, retardation, decline, prevention or decrease of at least about 5%-99.9999%, about 10%-90%, about 15%-85%, about 20%-80%, about 25%-75%, about 30%-70%, about 35%-65%, about 40%-60% or about 45%-55%, and more specifically may be by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, 99.99%, 99.999%, 99.9999% or about 100%, of the CoV infections, or infectious condition associated therewith as discussed above.

Still further, the invention provides a method of inducing an immune response against a viral infection, specifically, against coronavirus in a subject in need thereof. The method comprising administering to the subject an immunogenic effective amount of at least one polypeptide comprising an amino acid sequence of at least one reconstituted RBM of CoV Spike protein or any fragments thereof, any derivative, enantiomer, fusion protein, conjugate or polyvalent dendrimer thereof, or of any composition or vaccine comprising the same. More specifically, the native RBM is comprised within the Receptor Binding Domain (RBD) of said Spike protein forming a binding interface that interacts with the viral receptor. The RBM is an extended 30 to 100 or more amino acid excursion, juxtaposed along the edge of the core of the RBD and tacked to the core via a tacking segment. More specifically, the reconstituted RBM comprises at least one exogenous linker. In some embodiments, at least one of said linker/s may replace or added to at least one of: the tacking segment, any part or amino acid residue/s thereof and any RBM fragment or amino acid residue/s not directly involved in receptor binding.

It should be appreciated that any of the reconstituted RBM defined by the invention as well as any polypeptides, compositions or vaccines comprising these reconstituted RBMs, may be used for any of the methods of the invention. Of particular interest are any of the MERS-Cov reconstituted RBM polypeptides, specifically, any of the polypeptides comprising the amino acid sequence of SEQ ID NO: 48, 50, 52, 54, 56, 58, 59, 60, 61, 62, 63 and 64. In yet some further embodiments any of the SARS-CoV polypeptides of the invention, specifically, and of the polypeptides comprising the amino acid sequence of SEQ ID NO: 89-110, may be used in the methods of the invention.

Still further embodiments relate to the methods of the invention that may be applicable for any Coronavirus infection or any related disorders. Such infection may be caused by any CoV infecting mammalian subject/s, avian subject/s or any other vertebrates.

In more specific embodiments, the methods of the invention may be applicable for infections caused by coronavirus that may be any one of MERS CoV and SARS-CoV.

The invention further provides the use of the polypeptide as defined by the invention in the preparation of an epitope based CoV vaccine for inducing an immune response against a coronavirus in a subject in need thereof.

A further aspect of the invention relates to an isolated polypeptide as defined by the invention, for use in a method of inducing an immune response against a coronavirus in a subject in need thereof. As disclosed by the examples, a fully functional CoV RBM has been presently reconstituted by the inventors employing phage-display peptide-libraries. This was achieved by generating a vast collection of candidate RBM peptides that present a diversity of conformations. Screening such “Conformer Libraries” with corresponding ligands produced short RBM constructs (ca. 40 amino acids) that can bind both the viral receptor, specifically, the ACE2 receptor, in case of SARS-CoV, or the CD26/PPD4 in case of MERS-CoV, and the neutralizing mAb 80R, 11A or m336, respectively.

More specifically, co-crystallization of ACE2 with the SARS CoV RBD (F. Li et al. 2005) revealed that the specific surface that mediates the binding is contained within an extended looped excursion separate and distinct from the core of the RBD. The RBM is a single sub-domain of the 51 protein that is tacked onto the core of the RBD via three hydrogen bonds contributed by the 16-amino acid loop extending perpendicular to the binding surface itself. The inventors were able to reconstitute a functional RBM containing 9 out of a total of 13 contact residues involved in ACE2 recognition (see FIG. 2A). This was accomplished in two steps. First it was hypothesized that the 16-amino acid loop was not only unnecessary for functional binding, but rather its presence hindered the functional folding of the RBM in the absence of the underlying core. Hence, this obstacle was removed. This however created a new problem, namely the need to bridge the gap between residues L443 and F460. The solution to this was to create libraries of combinatorial linkers and exploit the affinity selection using the mAb 80R, 11A or any other neutralizing antibody as a probe. This proved to be extremely effective and numerous variations of reconstituted RBMs were produced. The fact that the novel structures were recognized by three independent conformation-sensitive probes (mAbs 80R and 11A and the natural receptor ACE2) gives credence to the conclusion that isolated RBM, detached from the core of RBD, can fold independently and assume the functional conformation required for receptor and antibody binding, provided the “correct” linker is implemented to bridge the L443-F460 gap.

Figure 2A:
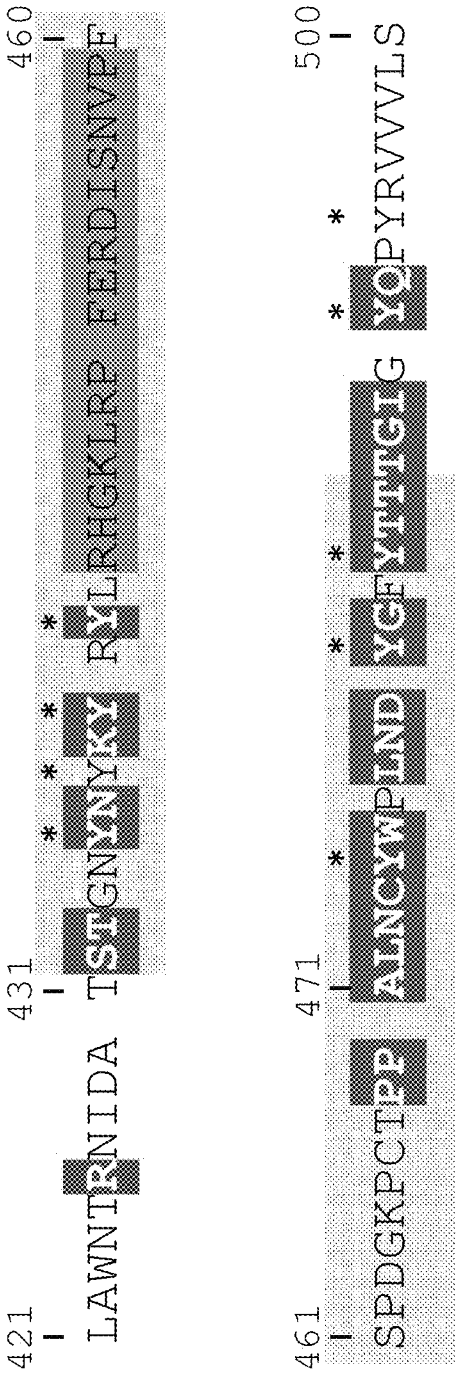
FIGS. 2A-2C. Schematic representation of SARS RBD residues interacting with the ACE2 receptor and the mAb 80R

Another important feature of the constituted RBM is a total of 9 tyrosines interspersed along the RBM extended loop (FIG. 2A and FIG. 7), 6 of them are used as contact residues for both ACE2 and mAb 80R (see FIG. 2A). The inventor hypothesized that these tyrosines contribute to functional binding sites. Hence, short peptides bearing 3 inter-spaced tyrosines, if unrestricted at the ends and free to assume unconstrained conformations, may adapt to the ACE2 helix and more easily associate with ACE2.

It should be noted that since the discovery of the RBD a number of attempts have been made to produce small peptide ligands that can bind ACE2 or act as inhibitors of viral entry via ACE2 (Chang et al. 2014; Ho et al. 2006; Hu et al. 2005; Struck et al. 2012). However, all previous attempts to express the truncated RBDs (Wong et al. 2004), as well as the inventor's initial attempts to reconstitute the RBM, failed to produce effective binders despite the presence of the same tyrosine-rich sequences of the RBM. Thus, one can conclude that the linear sequence of the RBM must fold into the correct conformation in order to assume a functional binding surface.

Previous efforts by the inventors (Bublil et al. 2006; Bublil et al. 2007; Gershoni et al. 2007; Mayrose et al. 2007a; Mayrose et al. 2007b; Rubinstein et al. 2008; Tarnovitski et al. 2006) focusing on mapping of neutralizing-epitopes, provided the first step in the development of "epitope based vaccines". In the present invention, the inventors have made a big leap forward towards accomplishing this goal in demonstrating the ability to reconstitute and produce the neutralizing epitopes as independently-folded and functional bioactive peptides. The production of comprehensive Conformer Libraries has been presently proven effective in the affinity selection of functional binding surfaces.

Thus, another aspect provided by the invention relates to a method for the preparation of a functional reconstituted RBM of a viral Spike protein. In some embodiments, the method of the invention may comprise:

In a first step (a), providing or constructing a conformer library of RBMs of said viral Spike protein, comprising plurality of bacteriophages. More specifically, each of these bacteriophages express a reconstituted RBM comprising an amino acid sequence of at least one fragment of an RBM of a viral Spike protein and at least one exogenous combinatorial linker. The next step (b) involves screening the library with a binding molecule. The final step (c) requires identifying and producing reconstituted RBM peptides which bind at least one of the binding molecules. In some embodiments, the bacteriophages used by the method of the invention may express a reconstituted RBM comprising an amino acid sequence of at least one, at least two, at least three, at least four, at least five, at least six, at least seven, at least eight, at least nine, at least ten or more fragment/s of an RBM of a viral Spike protein. It should be further appreciated that the invention encompasses any reconstituted RBM prepared by the method of the invention.

In some embodiments, the functional reconstituted RBM is capable of eliciting the production of neutralizing antibodies in an immunized subject.

In yet some further specific embodiments, the spike protein may be a Coronavirus (CoV) 51 protein. In some specific embodiments, the 51 protein may be a MERS-CoV or a SARS CoV spike protein. Still further, the reconstituted functional RBM as used by the method of the invention may be any of the reconstituted RBMs as defined by the invention.

As indicated above, the reconstituted RBMS are constructed in conformer libraries containing combinatorial linkers. A "peptide library" is a collection of peptides, that may range from 2 to 100, specifically, from 3 to 90, 4 to 80, 5 to 70, 6 to 60, 7 to 50, 8 to 40, 9 to 30, 10 to 20 or 5 to 25 amino acid residues in length. The collection of peptides may be a random collection or it may be rationally designed based on the composition of the proteinaceous material of which the binding surface is a part.

The greater the number of different peptides in the library, the better. Preferably, in the case of a random peptide library, it may contain more than $10^6$, 10' or more different peptides.

In the peptide library, the peptides may be displayed by any means, such as, for example, peptides displayed on phage, a combinatorial library of synthetic peptides on beads, etc. Phage display libraries of random peptides are well known in the art.

More specifically, as shown by the examples, the functional reconstituted RBMs of the invention were isolated by screening of a conformer peptide library, that enables the screening of library expressing genuine fragments of the native RBM inter-connected with a vast collection (millions) of combinatorial linkers, thus generating a "Conformer Library" where each linker enables the RBM fragments to assume a unique three dimensional conformation. One of the factors contributing to the diversity of a phage-displayed peptide library is the method of library construction. When designing peptide-encoding oligonucleotide DNA to be inserted into the phage genome, the type of genetic code employed is of utmost importance because the observed frequency of amino acids displayed in the library is directly correlated to the number of codons encoding each amino acid. For instance, the standard 64-codon genetic code encodes each of the twenty amino acids and three stop codons with the number of codons per amino acid ranging from one (methionine, tryptophan) to six (leucine, serine, arginine). Amino acids encoded by higher numbers of codons have a greater chance of being incorporated into the library, while amino acids with fewer codons have a lesser chance. This discrepancy results in non-uniform amino acid frequencies and thus, limited peptide diversity. Ideally, a library would contain peptides with even 5% amino acid frequencies (one amino acid out of twenty) per each amino acid position within the peptides. To produce libraries with more even amino acid frequencies, phage-displayed peptide libraries are typically created using a reduced genetic code when designing the insert oligonucleotide DNA encoding the displayed peptides. The oligonucleotides are designed in the 'NNK' format, where N represents equal proportions of guanine, cytosine, thymine, and adenine nucleotides, and K represents equal proportions of thymine and guanine nucleotides. This method encodes all twenty amino acids and one stop codon, while smoothing the number of codons per amino acid to one, two, or three. Although the NNK method of library construction provides each amino acid a more equal opportunity of incorporation into the peptide library, the method still imparts some amino acid sequence bias because the amino acids are encoded by varying numbers codons.

More specifically, for identifying functional reconstituted RBM polypeptides, conformer libraries produced by step (a) of the method of the invention, are screened to identify reconstituted RBMs that contain a sufficient portion of a binding surface, folded and presented in a correct functional structure. In some embodiments, such portion of a binding surface may comprise at least one amino acid residue that participate in binding. By "Functional" as used herein, it is meant that the binding surface is capable of mimicking the native binding surface of the RBD and therefore is capable of binding the receptor as well as several neutralizing antibodies. A "binding surface" as used herein, is that portion of a proteinaceous material that associates with a binding molecule.

The "binding molecule" is any molecule, whether or not proteinaceous, that associates with a binding surface, i.e., binds to the binding surface with specificity dependent on the structure of that surface and with high affinity. The binding molecule-binding surface association is mainly discussed herein from the standpoint of the antibody-antigen and/or a ligand-receptor association, however, it should be noted that such associations may also include a receptor-hormone association, an enzyme-substrate association, or any other protein-protein interaction.

It should be however understood that while the binding molecule may itself be a proteinaceous material, such as an antibody, an enzyme, a ligand, a receptor, etc. in some embodiments, it may not be necessarily proteinaceous. Thus, for example, the binding molecule may be a polynucleotide sequence or a sugar molecule, gangliosides, lipids, etc.

To identify functional reconstituted RBM polypeptides, specifically, the RBMs that are capable of eliciting the production of neutralizing antibodies in the immunized subject, thereby inhibiting and preventing viral entry to the target cells of said subject, the library provided by the invention is screened with "binding molecules" as discussed above.

In some embodiments, the binding molecule may be at least one of: (a) the receptor for said CoV or any fragments thereof; (b) a neutralizing antibody directed against the wild type CoV RBM and any combinations thereof.

As noted herein above, the binding molecule used by the method of the invention may be an antibody, specifically, a neutralizing antibody (nAb). A neutralizing antibody capable of disturbing and eliminating the interaction of the virus with its host cell and thereby prevents and reduces viral entry to the target cell. Non-limiting examples for antibodies used in the invention may include but are not limited to SARS-CoV mAb 80R and mAb 11A, and the MERS-CoV mAb m-336 and the like.

The term 'antibody' as meant herein encompasses the whole antibodies as well as any antigen binding fragment (i.e., 'antigen-binding portion') or single chain thereof. An 'antibody' refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region (abbreviated herein as CH). Each light chain is comprised of a light chain variable region (abbreviated herein as VL) and a light chain constant region (abbreviated herein as CL). The VH and VL regions can be further subdivided into regions of hypervariability, termed 'complementarity determining regions' (CDRs), interspersed with regions that are more conserved, termed "framework regions" (FRs). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term 'antigen-binding portion' of an antibody, as used herein, refers to one or more fragments of an antibody that retain the ability to specifically bind to an antigen. It has been shown that the antigen-binding function of an antibody can be performed by fragments of a full-length antibody. Examples of binding fragments encompassed within the term 'antigen-binding portion' of an antibody include (i) a Fab fragment, a monovalent fragment consisting of the VL, VH, CL and Cm domains; (ii) a F(ab')2 fragment, a bivalent fragment comprising two Fab fragments linked by a disulfide bridge at the hinge region; (iii) a Fd fragment consisting of the VH and Cm domains; (iv) a Fv fragment consisting of the VL and VH domains of a single arm of an antibody, (v) a dAb fragment, which consists of a VH domain; (vi) an isolated complementarity determining region (CDR), and (vii) a combination of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules. Such single chain antibodies are also intended to be encompassed within the term "antigen-binding portion" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. These antibody fragments are obtained using conventional techniques known to those with skill in the art, and the fragments are screened for utility in the same manner as are intact antibodies.

More specifically, an 'antibody fragment' is a portion of an antibody such as F(ab')2, F(ab)2, Fab', Fab, and the like. Regardless of structure, an antibody fragment binds with the same antigen that is recognized by the intact antibody. For example, an anti-(polypeptide according to the present invention) monoclonal antibody fragment binds an epitope of a polypeptide according to the present invention. The term 'antibody fragment' also includes a synthetic or a genetically engineered polypeptide that binds to a specific antigen, such as polypeptides consisting of the light chain variable region, 'Fv' fragments consisting of the variable regions of the heavy and light chains, recombinant single chain polypeptide molecules in which light and heavy variable regions are connected by a peptide linker ('scFv proteins'), and minimal recognition units consisting of the amino acid residues that mimic the hypervariable region.

The term 'epitope' means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Methods for preparing antibodies are known to the art. See, for example, Harlow & Lane (1988) Antibodies: a Laboratory Manual, Cold Spring Harbor Lab., Cold Spring Harbor, N.Y.). Monoclonal antibodies may be prepared from a single B cell line taken from the spleen or lymph nodes of immunized animals, in particular rats or mice, by fusion with immortalized B cells under conditions which favor the growth of hybrid cells. The technique of generating monoclonal antibodies is described in many articles and textbooks, such as the above-noted Chapter 2 of Current Protocols in Immunology. Spleen or lymph node cells of these animals may be used in the same way as spleen or lymph node cells of protein-immunized animals, for the generation of monoclonal antibodies as described in Chapter 2 therein. The techniques used in generating monoclonal antibodies are further described in by Kohler and Milstein, Nature 256; 495-497, (1975), and in U.S. Pat. No. 4,376,110. Antibodies that are isolated from organisms other than humans, such as mice, rats, rabbits, cows, can be made more human-like through chimerization or humanization.

In some embodiments, the binding molecule used for screening the library of the invention, may be the viral receptors, or any fragments thereof.

In some specific embodiments, the CoV RBM may be MERS CoV RBM, and the receptor may be therefore PDD4/CD26 or any fragment thereof.

In some other embodiments, the CoV RBM may be SARS CoV RBM, and the receptor may be Angiotensin-Converting Enzyme 2 (ACE2) or any fragment thereof.

Figures 2B, 2C:
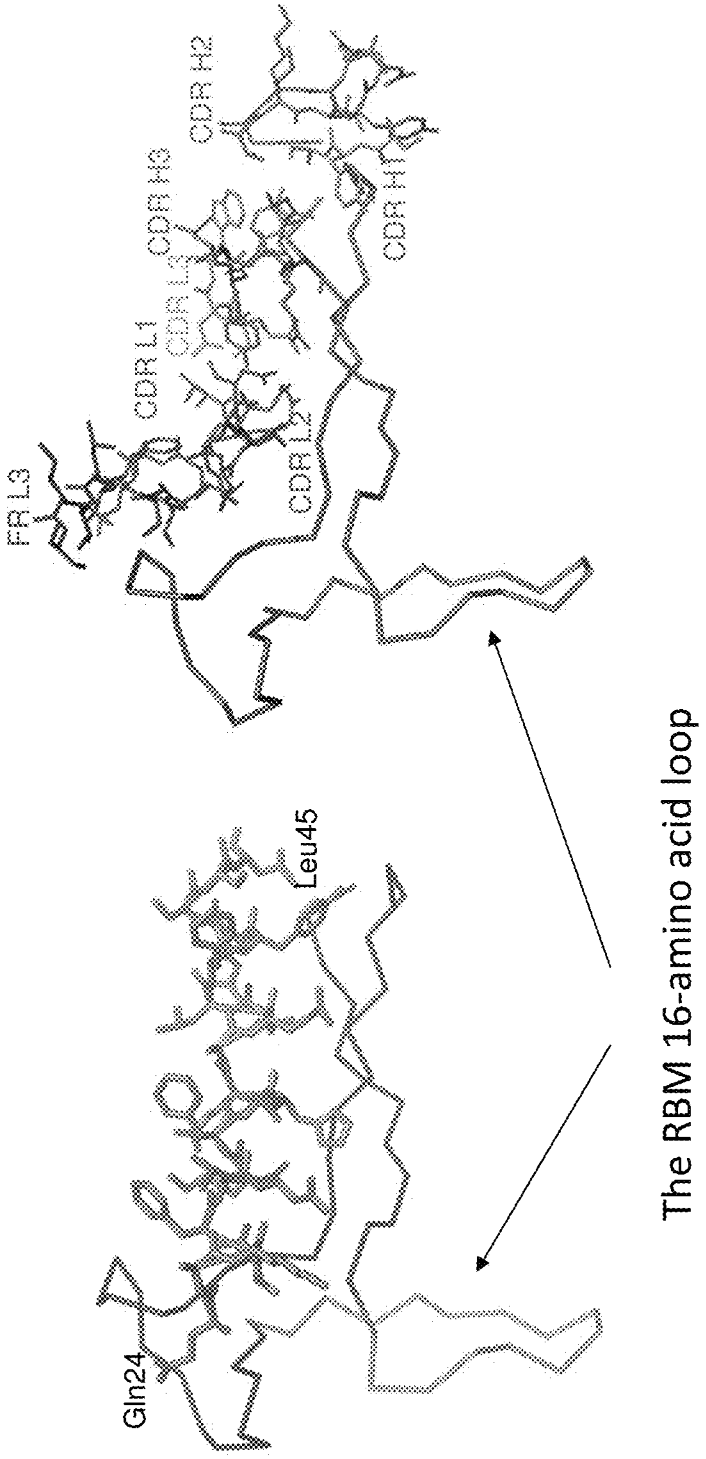

In the present context, Conformer Libraries express constant compositions and sequences of the RBM per se yet differ in the details of their three dimensional conformations. This was accomplished by implementing a vast collection of random combinatorial linkers varying in length and composition. The affinity selection of conformers that satisfy the spatial orientation and display of the native contact residues has been proven very efficient. Validity of this method was supported by the fact that three independent conformation-specific probes detected constructs incorporating the same linkers. These three probes represent two very different modes of interaction with an extended surface of the RBM (FIGS. 2B-2C). The natural ligand, i.e. the viral receptor ACE2 employs a single continuous helix that contacts 10 residues, 8 of which are contained within the RBM (spanning S432-T486, SEQ ID NO: 3), and no contacts within the 16-amino acid structural loop (FIG. 2B, highlighted). The mAb 80R, on the other hand, uses a totally different mode of recognition (FIG. 2C). All three CDR loops of the heavy chain and 2 CDR loops of the light chain in addition to 2 discontinuous segments of the framework contribute 23 contact residues (9 common with those contacting ACE2). Once again no contacts are made with the 16-amino acid loop (FIG. 2C, highlighted). Hence, the inventors conclude that the affinity selected linkers in their ability to satisfy such diverse ligand interactions must enable RBM to assume its natural conformation. Moreover, the fact that the linkers themselves represent a common motif goes to illustrate that a distinct structure and composition of linker is required so to place the contact residues in register and position to be complemented by the binding counter-parts.

It is conceived that the above described approach is applicable to any viral pathogen, specifically, any CoV that has the same general layout/structure with a RBD juxtaposed to a core. For any specific case, the inventors propose to remove/delete the "loop" that functions for RBM tacking to the body of RBD core, any parts thereof or any RBM fragment or amino acid residue not involved, participating or essential to receptor interaction and binding, and thus faces in the opposite direction relative to the binding surface that interacts with the receptor and is the target of neutralizing antibodies. As a result of this deletion, a gap is generated that requires a linker. The inventors have presently demonstrated how to design of a potential linker, in terms of length and composition, by introducing the concept of combinatorial linkers and conformer libraries, and a method for screening these libraries with concrete reagents that have affinity for RBM, i.e. the receptor and neutralizing antibodies.

More specifically, the selection of the correct linker length and composition is based on a pull down and affinity selection of conformers bearing the correct linker, and thereby reconstitution of a recognizable conformation. In the example of SARS, the gap was about 7A and ultimately was bridged with linker 3 and 4 residues in length. With regard to MERS, the same concept is applied. Composition of the successful linkers indicates that they are not random, but rather represent a motif in themselves, thus illustrating the uniqueness of these linkers and the fact that affinity selection not only works but apparently is necessary to discriminate the correct linkers from the vast collection of all other linkers in the conformer library.

The immunogenic peptides conceived by the present invention are applicable for generation of specific vaccines and vaccine-based therapeutic compositions targeting CoVs. A number of methods for producing specific formulation for vaccines are known in the art. A rational systematic approach for the development of vaccine formulations was provided for example by Morefield G. L. in AAPS J. 2011, Vol. 13(2), pp. 191-200.

Thus, in a further aspect, the invention further provides a method for producing epitope based CoV vaccine or immunogenic composition comprising reconstituted RBM. More specifically, the method comprising the step of:

(a) preparing reconstituted functional RBM/s of a CoV Spike protein, specifically, by the method as defined by the invention; and (b) admixing at least one of said reconstituted functional RBM/s of a CoV Spike protein or any derivative or enantiomer thereof, or any fusion protein, conjugate, or polyvalent dendrimer comprising the same with at least one adjuvant/s, carrier/s, excipient/s, auxiliaries, and/or diluent/s.

In yet some further embodiments, the reconstituted RBMs of the invention or any derivative, enantiomer, fusion protein or conjugate thereof may be presented in the vaccines of the invention as a polyvalent antigen by incorporation thereof in a polyvalent dendrimer. This embodiment is based on the knowledge in the art that a multiple antigen peptide carrying a multiplicity of epitopes induces superior immune responses compared to responses following immunization with corresponding equal amounts of monovalent epitopes.

Thus, in some embodiments, the present invention is intended to broadly encompass antigenic products carrying multiple copies of the reconstituted RBM polypeptides of the present invention an in a multiple antigen peptide system.

The present dendritic polymers are antigenic products in which the reconstituted RBM polypeptides are covalently bound to the branches that radiate from a core molecule. These dendritic polymers are characterized by higher concentrations of functional groups per unit of molecular volume than ordinary polymers. Generally, they are based upon two or more identical branches originating from a core molecule having at least two functional groups. The polymers are often referred to as dendritic polymers because their structure may be symbolized as a tree with a core trunk and several branches. Unlike a tree, however, the branches in dendritic polymers are substantially identical.

The dendrite system has been termed the "multiple antigen peptide system" (MAPS), which is the commonly used name for a combination antigen/antigen carrier that is composed of two or more, usually identical, antigenic molecules, specifically, the reconstituted RBM polypeptides of the invention covalently attached to a dendritic core which is composed of principal units which are at least bifunctional/difunctional. Each bifunctional unit in a branch provides a base for added growth. The dendritic core of a multiple antigen peptide system may be composed of lysine molecules. For example, a lysine is attached via peptide bonds through each of its amino groups to two additional lysines. This second generation molecule has four free amino groups each of which can be covalently linked to an additional lysine to form a third generation molecule with eight free amino groups. A peptide may be attached to each of these free groups to form an octavalent multiple peptide antigen (MAP). The process can be repeated to form fourth or even higher generations of molecules. With each generation, the number of free amino groups increases geometrically and can be represented by $2^n$, where n is the number of the generation. Alternatively, the second generation molecule having four free amino groups can be used to form a tetravalent MAP with four peptides covalently linked to the core. Many other molecules, including, e.g., the amino acids Asp and Glu, both of which have two carboxyl groups and one amino group to produce poly Asp or polyGlu with 2n free carboxyl groups, can be used to form the dendritic core of MAPS.

The term "dendritic polymer" is sometimes used herein to define a product of the invention. The term includes carrier molecules which are sufficiently large to be regarded as polymers as well as those which may contain as few as three monomers.

The chemistry for synthesizing dendritic polymers is known and available. With amino acids, the chemistry for blocking functional groups which should not react and then removing the blocking groups when it is desired that the functional groups should react has been described in detail in numerous patents and scientific publications. The dendritic polymers and the entire MAP can be produced on a resin and then removed from the polymer. Ammonia or ethylenediamine may be utilized as the core molecule. In this procedure, the core molecule is reacted with an acrylate ester and the ester groups removed by hydrolysis. The resulting first generation molecules contain three free carboxyl groups in the case of ammonia and four free carboxyl groups when ethylenediamine is employed. The dendritic polymer may be further extended with ethylenediamine followed by another acrylic ester monomer, and repeats the sequence until the desired molecular weight was attained. It is readily apparent to one skilled in the art, that each branch of the dendritic polymer can be lengthened by any of a number of selected procedures. For example, each branch can be extended by multiple reactions with Lys molecules.

Some important features of the dendritic polymer as an immunogenic carrier are that the precise structure is known, there are no "antigenic" contaminants or those that irritate tissue or provoke other undesirable reactions. The precise concentration of the reconstituted RBM polypeptide of the invention is known; and is symmetrically distributed on the carrier; and the carrier can be utilized as a base for more than one reconstituted RBM polypeptide so that multivalent immunogens or vaccines can be produced.

When the MAPS is to be employed to produce a vaccine or immunogenic composition, it is preferred that the core molecule of the dendrimer be a naturally occurring amino acid such as Lys so that it can be properly metabolized. However, non-natural amino acids residues may be also employed. The amino acids used in building the core molecule can be in either the D or L-form.

In brief, in manufacturing vaccine products it is important to have a good understanding of what factors can impact the safety, efficacy, and stability of the formulation all along the development path. The main phases in this process are: biophysical characterization of the antigen, evaluation of stabilizers, investigation of antigen interactions with adjuvants, evaluation of product contact materials such as sterile filter membranes, and monitoring stability both in real time and under accelerated conditions.

Biophysical Characterization Phase refers to evaluation of the physical characteristics of the antigen, i.e. understanding how parameters such as pH, buffer species, and ionic strength impact the folded state of the antigen as well as the propensity of the antigen to aggregate. Knowing how characteristics of the formulation will impact physical stability of the antigen will aid selection of appropriate excipients during the development process.

Empirical Phase refers to initiation of preformulation studies for the systematic development of a vaccine formulation. A logical place to start, is understanding how the physical stability of the antigen is impacted by changes in pH and temperature. The pH of the formulation can impact both the physical stability of the antigen, such as whether the antigen maintains the appropriate folding and if the antigen will aggregate, as well as the chemical stability of the antigen. The pH can impact the chemical degradation rate of many mechanisms of degradation such as hydrolysis, oxidation, and deamidation. The Empirical Phase Diagram offers a convenient way to display how the physical stability of an antigen is impacted with changes in pH and temperature. Generally in this approach, characterization data are taken from various spectroscopic techniques such as second derivative UV/Vis, intrinsic fluorescence, extrinsic fluorescence, and circular dichroism are combined and transformed into data vectors to construct the empirical phase diagram. In addition to pH evaluation, the Empirical Phase Diagram approach can be utilized to determine the impact of other variables on antigen stability like buffer type and concentration, ionic strength, and impact of product contact material.

Evaluation of Stabilizers refers to optimization of formulation parameters such as pH, ionic strength, and buffer species may not prove to be enough to stabilize an antigen for the typically desired 3-year shelf life of vaccine products. In this case stabilizing excipients need to be investigated for incorporation into the vaccine formulation. Evaluation of antigen stabilizers typically begins with investigation of generally regarded as safe (GRAS) excipients. By utilizing GRAS excipients, development may proceed more rapidly as regulatory concerns regarding safety of the formulation excipients will be lower. Since at the early stage of development the primary mechanism of antigen degradation may not be known it is important to evaluate excipients from various classes of stabilizers. Excipient screening such as monitoring of optical density or extrinsic fluorescence can be performed in a 96 well format to allow high-throughput screening of many excipients and excipient combinations at one time.

Correlation of Real-time and Accelerated Stability, refer to analysis of the stability of a formulation under extreme environmental conditions such as high temperatures. Correlation of accelerated stability with real-time data is valuable to support activities such as expiration dating and assessment of the impact of temperature excursions during shipment and storage of the vaccine for clinical trials. When initiating stability studies it is important to understand potential mechanisms of antigen can degradation. In general, physical instability is associated with loss of protein structure and aggregation while common forms of chemical degradation are oxidation and deamidation. In addition to high temperature excursions, it is useful to determine the impact of other factors on formulation stability, such as exposure to environmental stresses such as cycles of freezing and thawing, extended exposure to light, and contact with various storage container materials.

Adjuvants or Adjuvantation refers to enhancement of antigen immunogenicity. A side effect of vaccine antigens becoming more pure as purification technology has advanced is a reduction in the immunogenicity of the antigen. To retain antigen immunogenicity with more highly purified antigens, adjuvants can be incorporated into the vaccine formulation. Adjuvants interact with the immune system through various mechanisms thereby enhancing the immune response. Currently, the most utilized adjuvants in licensed products are aluminum salts and squalene-based oil-in-water emulsions. Aluminum-containing adjuvants, including aluminum hydroxide (AlO(OH) and aluminum phosphate $(Al(OH)_x(PO_4)_y$ adjuvants, have a long history of use and an excellent safety profile.

Sterile Filtration refers to prevention of microbial contamination of vaccines is an important part of producing a safe vaccine formulation. As vaccines are administered to infants, children, and adults who are generally healthy at the time of injection there is a high level of safety that must be ensured when manufacturing the vaccine product. Typically, this can be achieved through aseptic processing and sterile filtration of the vaccine formulation. However, formulations with aluminum-containing adjuvants cannot be sterilized by filtration due to the particle size of the adjuvant being greater than 0.2 Materials used to prepare vaccines with aluminum-containing adjuvants must be sterilized prior to formulation and handled aseptically during the formulation and filling process. Sterile filter membranes are produced with various materials, typical membranes used in vaccine production are cellulose acetate, polyethersulfone and polyvinylidene fluoride.

All scientific and technical terms used herein have meanings commonly used in the art unless otherwise specified. The definitions provided herein are to facilitate understanding of certain terms used frequently herein and are not meant to limit the scope of the present disclosure.

Before specific aspects and embodiments of the invention are described in detail, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, references to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. More specifically, the terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to ±10%.

It should be noted that various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

The examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

EXAMPLES

Materials and Methods

Vectors

The fth-1 vector was developed at Tel Aviv University as described in (Enshell-Seijffers et al. 2001) and used to express inserts of choice at the N-terminus of the recombinant pVIII major coat protein of the fd filamentous bacteriophage.

Monoclonal Antibodies and Proteins

The human mAbs 80R (Sui et al. 2004) and 11A (Sui et al. 2008), which target the RBD of the SARS Co-V, and the human ACE2 protein were produced at the Dana-Farber Cancer Institute, Boston, Mass. Polyclonal rabbit anti-M13 sera and the recombinant pVIII-specific GIL-Ab (Kaplan and Gershoni 2012) as well as the anti-m13 mAb Y2D (Siman-Tov et al. 2013) were produced at Tel Aviv University.

Cloning of the SARS CoV RBM Constructs

The initial SARS CoV RBM construct was produced by cloning residues S432-T486 of the RBD (denoted by SEQ ID NO:3) between the two SfiI restriction sites of the fth-1 recombinant pVIII gene. The "loop less" RBM phage was prepared by cloning the two strands, 432STGNYNYKYRL$_{443}$ (also denoted by SEQ ID NO: 5) and $_{460}$FSPDGKPCTPCTPPALNCYWPLNDYGFYTT$_{486}$ (also denoted by SEQ ID NO: 6), contiguous to one another between the two SfiI restriction sites of the fth-1 recombinant pVIII gene. Using alternative codon usage two unique restriction sites were introduced, one in each strand: the restriction site for KpnI enzyme in the S432-L443 strand and the restriction site for ApaLI enzyme in the 5460-T486 strand. In general, compatible oligonucleotides encoding the relevant construct were designed to create 5' and 3' overhangs compatible to the SfiI cloning sites of the fth-1 vector (Enshell-Seijffers et al. 2001) and annealed to create double stranded inserts that were introduced into the SfiI-digested fth-1 vector; for details see (Freund et al. 2009).

Construction and Analysis of "Conformer Libraries"—Phage-Displayed SARS CoV RBM Linker-Libraries All linker-libraries were cloned into the ApaLI and KpnI cloning sites of the "loop less" RBM vector. Briefly, for the construction of the libraries, two 5' biotinylated oligonucleotides were used. The first contained the "library" sequence flanked by ApaLI and KpnI sites compatible with the ApaLI and KpnI cloning sites of the "loop less" RBM vector. The second oligonucleotide complemented the 3' end of the first and was extended to "fill-in" the complementary strand using Klenow polymerase. The product was digested with ApaLI and KpnI, the short biotinylated segments were removed with streptavidin-conjugated beads, and the insert in the flow-through was collected and cloned into ApaLI and KpnI digested vector. This ligation mix was used to electroporate MC1061 cells; for details see (Freund et al. 2009). The randomness of each library was confirmed by sequencing 20-40 randomly picked colonies. The complexities of linker-libraries with linkers comprised of $NNK_1$, $NNK_2$, $NNK_3$, $NNK_4$ were $7.5\times10^3$, $5\times10^6$, $1.4\times10^7$, $2\times10^7$ respectively.

Screening of SARS CoV "Conformer Libraries"

50 μg of protein G (Sigma Chemical Co., St. Louis, Mo.) in Tris-buffered saline (50 mM Tris-HCl pH 7.5, 150 mM NaCl (TBS)), were used to coat the bottom of Costar 6-well tissue culture plates (Corning Incorporated, Corning, N.Y.) overnight at 4° C. The wells were blocked with 0.25% gelatin in TBS (TBSG), washed briefly with TBS, and then incubated with 20-70 μg/ml of mAb 80R at room temperature for at least 4 hours. Unbound antibody was washed out with TBS, and the plate was incubated overnight at 4° C. with $10^{11}$ phages from the phage-display library, arising from the transformed MC1061 cells described above, suspended in TBSG. After extensive washing, the mAb 80R-bound phages were eluted with glycine-HCl pH 2.2 and neutralized with Tris-HCl pH 9.1.

Two additional rounds of amplification and biopanning were carried out for each screen. In order to confirm mAb 80R binding to affinity-selected phages, single colonies were picked and grown as mini-cultures from which dot-blots on nitrocellulose membrane filters were prepared. The filters were blocked using 5% skim milk in TBS for lhour at room temperature, probed with mAb 80R at 4° C. (2 μg/ml) and subsequently detected using HRP-conjugated antibodies (1:5000, Jackson, West Grove, Pa.). Signals were developed using the enhanced chemo-luminescence reaction (Rhenium, Israel). For details see (Freund et al. 2009).

Phage Preparation (Comprising SARS CoV Constructs)

Phages displaying the peptides of interest were used to infect *E. coli* DH5αF' bacteria. The infected bacteria were grown in 100 ml TY×2 with 20 μg/ml of tetracycline medium overnight and then centrifuged to pellet bacteria. The phage-containing supernatants were transferred to PEG/NaCl solution and incubated at 4° C. overnight to precipitate phages. Following centrifugation, the precipitated phages were re-suspended in TBS and filtered through a 0.45 μm filter, and titered using a plaque assay.

ELISA Tests of SARS CoV Constructs

Nunc-Immuno Modules ELISA wells (Nunc, Roskilde, Denmark) were coated overnight with 5-10 μg/ml of mAb 80R, or ACE2 in phosphate buffered saline (PBS). Next, the plates were washed with PBS, blocked with 5% skim milk in PBS and incubated with a suspension of $10^{10}$ phages/well. Wells were washed with PBS and incubated with polyclonal rabbit anti-M13 antibody. Next, wells were washed and incubated with HRP-conjugated goat anti-rabbit antibody (1:5000, Jackson, West Grove, Pa.). Following an additional round of washing, wells were reacted with the TMB/E ELISA substrate (Merck Millipore, Billerica, Mass.). Absorbance was measured at 650 nm using a micro-plate reader (BioTek, Winooski, Vt., USA). All experiments were repeated at least three times and typically performed in duplicates.

Construction of MERS CoV RBM Linker-Libraries

MERS CoV RBM linker-library was prepared as illustrated in FIG. 12 and as detailed below. An oligonucleotide corresponding to the amino acid sequence of residues 535-546 (having the amino acid sequence WEDGDYYRKQLS defining β strand 7 and denoted by SEQ ID NO: 37) and residues 551-560 (having the amino acid sequence GGWLVASGST defining β strand 8 and denoted by SEQ ID NO: 38) (FIG. 12A) was synthesized with NNK inner linkers of 1, 2, 3, 4, or 5 NNK repeats having various sequences (FIG. 12B).

Next, a 20 nucleotides-long antisense oligonucleotide were used to prime the Klenow fill-in of the constructs, thus generating five of double strand DNA templates that differ only in the number of NNK repeats (FIG. 12D).

Then, the double-stranded DNA templates were amplified by PCR using forward and reverse primers (F and R in FIG. 12E) that at their 5' ends contained 0-3 NNK terminal linker codons.

Thus PCR reactions were carried with the above identified different forward and reverse primers simultaneously in five different reaction mixtures, each using a different template with either 1, 2, 3, 4 or 5 NNK consecutive linkers. A total of 80 libraries was produced containing random NNK linkers at either end as well as in the connecting linkers. The library DNA's are then cloned into Sfi1 cut fth1 vector via Gibson assembly, as described above for the SARS CoV constructs.

Example 1

Analysis of the SARS CoV RBD Structure

Construction of conformer libraries is based on expression of bona fide segments of the CoV Receptor binding motif (RBM) connected via vast collections of combinatorial linkers. The rationale is that various linkers will allow or impose upon the native segments to assume diverse conformations. Those linkers that induce a physiologically relevant conformation will be selected by panning the libraries with discerning ligands.

Figure 1A:
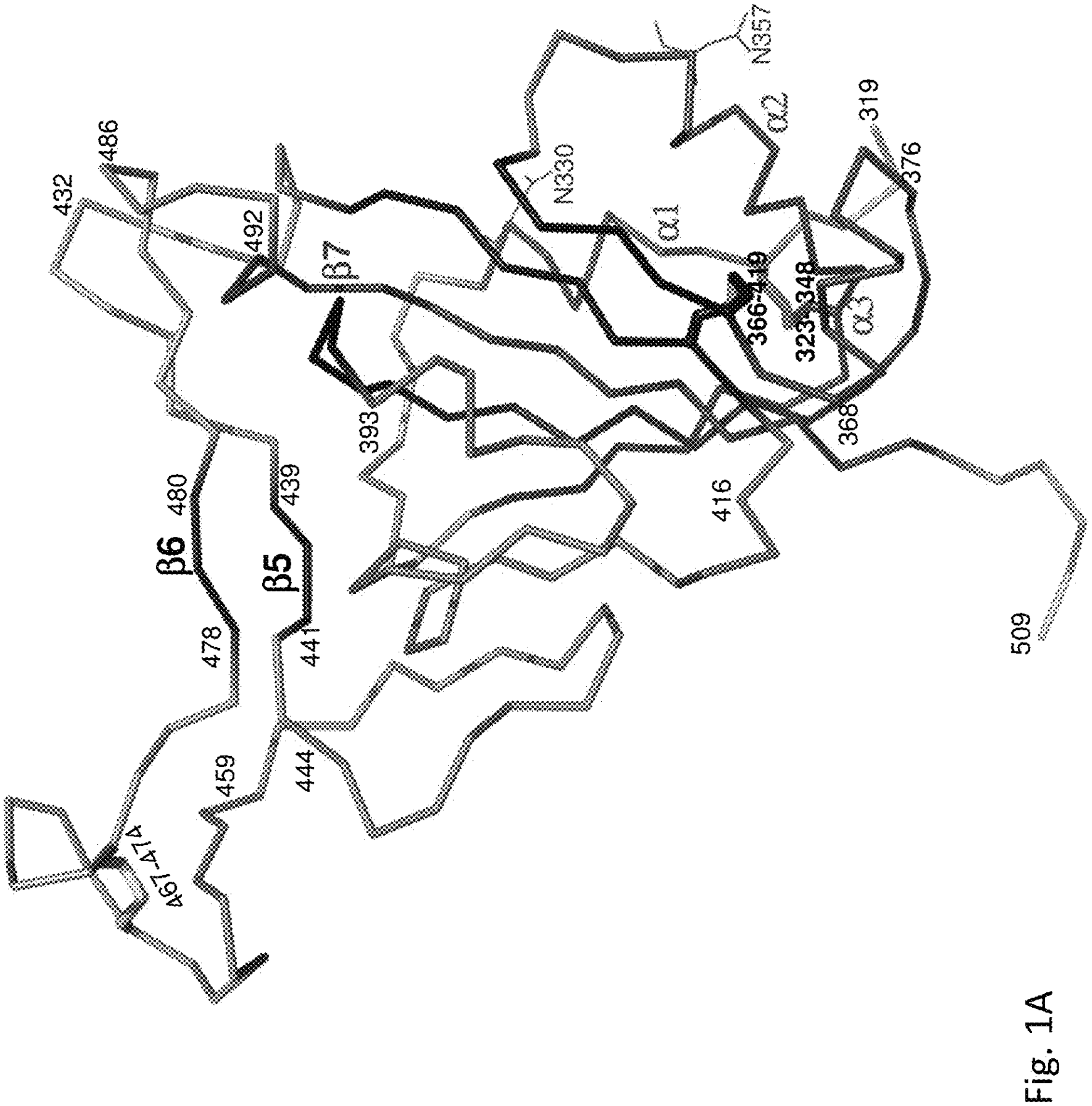
FIGS. 1A-1C. Schematic representation of the SARS CoV RBD structure
Figure 1B:
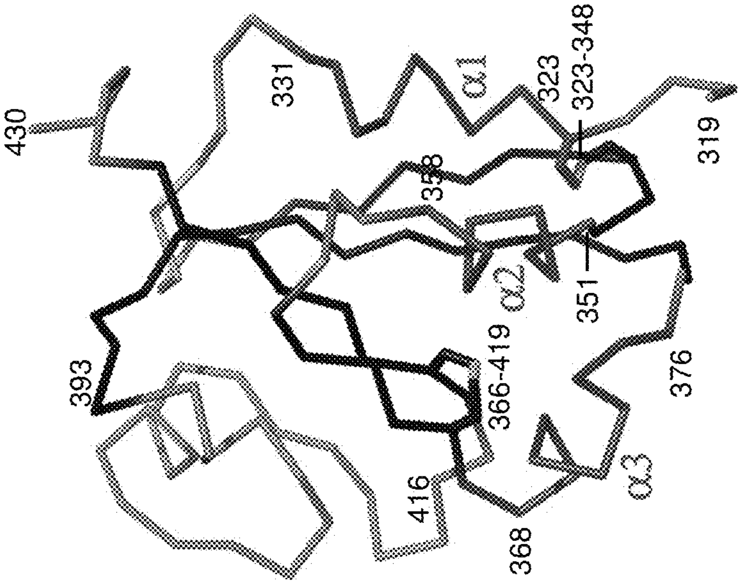
Figure 1C:
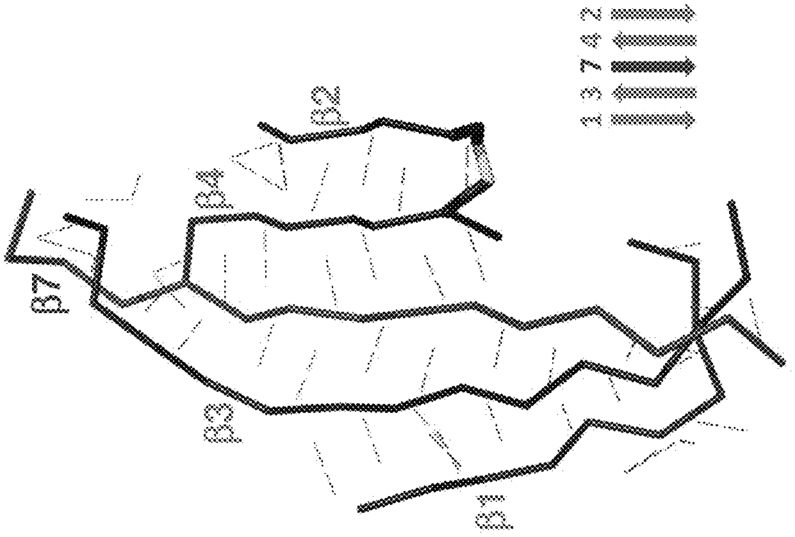

The atomic structure of the SARS CoV Receptor Binding Domain (RBD) was previously described at 2.9 and 2.3 angstrom (A) resolution in complex with its receptor ACE2 and with mAb 80R, respectively. The amino acid sequence of SARS CoV RBD is denoted by SEQ ID NO: 33. The RBD structure from the mAb 80R co-crystal is depicted in FIG. 1A. As can be seen, residues 1319 through A430 (denoted by SEQ ID NO: 28) create a compact core structure containing two glycosylation sites (N330, N357), two disulfide bonds (yellow bars) and a central anti-parallel beta sheet (β1-β4) (FIGS. 1B and 1C). On one side of the beta sheet exists a series of three alpha helices (blue), and on the other side—a looped structure, formed by residues N393-F416 (SEQ ID NO: 84, red, FIG. 1B). The CoV Receptor Binding Motif (RBM) is an excursion from the above core structure spanning residues 5432-T486 (also denoted by SEQ ID NO: 3) that lies on the edge of the core structure. RBM contains two anti-parallel beta strands (β5 and β6, as indicated in FIG. 1A), a single disulfide bond and a 16-amino acid loop (green) that tacks RBM to the core (formed by residues 444-459, also denoted by SEQ ID NO: 2). Finally, an extended beta strand (β7, dark green) stems from residue Y491 to L504 back down through the core serving as a lynch-pin, hydrogen bonding with β3 and β4, and thus holding the entire structure together (FIG. 1C). The inventors basing on the above understanding of the RBD structure could explain why previous attempts to express functional RBDs missing residues N318-N330 and thereby disrupting the disulfide C323-C348 and devoid of (31, or truncations at residues G490 thus deleting the (37 lynch-pin, failed to produce independently folding stable and functional structures (see for example Wong et al. 2004).

Further basing on this understanding, the inventors hypothesized that the segment of the RBM residing between residues 5432 through T486 (SEQ ID NO: 3) is capable of facilitating a vast majority of contacts with ACE2 and mAb 80R (see FIG. 2A). The inventors further hypothesized that despite the extensive overlap between the contacts that interact with these two ligands, their means to bind the RBM region are very different. More specifically, the ACE2 contacts 8 residues (spanning S432 to T486) of a total 9 via a single extended alpha helix (G1n24 through Leu45, see FIG. 2B). In contrast, mAb 80R contacts 23 residues of the RBM via a series of 7 discontinuous segments derived from VH and VL domains (see FIG. 2C). In view of the more elaborate network of contacts employed by mAb 80R the inventors decided to probe candidate RBM structures first with this antibody and followed by subsequent evaluation of ACE2 binding.

Example 2

Development of Cloning Strategy for Different SARS CoV RBM Constructs

Figure 3:
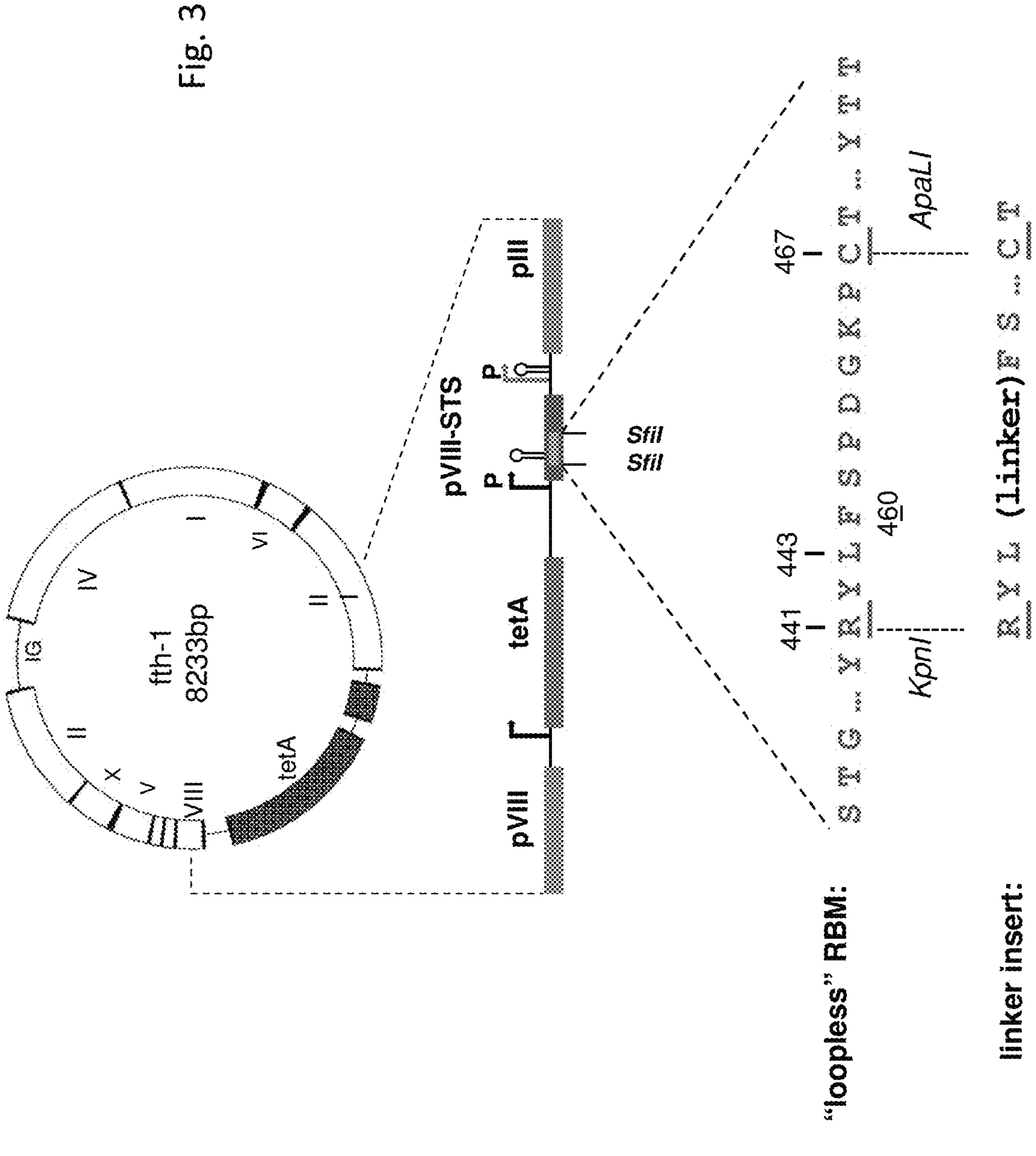
FIG. 3. Illustration of the cloning strategy for different SARS CoV RBM constructs Figure shows a schematic representation of the fth-1 vector, both the wild-type and recombinant (pVIII-STS) copy of the protein VIII (pVIII) genes are indicated. The recombinant protein VIII gene contains a DNA stuffer that encodes for two stop codons and an RNA transcription terminator (hairpin structure), promoters are also indicated. In the present EXAMPLES, the stuffer was removed, and an insert was cloned between the two SfiI sites. The two segments of the RBM region (residues 5432-L443, also denoted by SEQ ID NO: 5 (red) and residues F460-T486, also denoted by SEQ ID NO: 6 (blue)) were cloned into the recombinant pVIII gene generating a "loop less" RBM phage (the 16-amino acid loop was deleted, thereby directly connecting the two segments of RBM). Two unique restriction sites, KpnI and ApaLI, flanking the deleted "loop" are shown. See Materials and Methods for further details.

Initially, the native structure, residues S432 through T486 (denoted by SEQ ID NO: 3), was cloned into the SfiI sites of the phage-display fthl vector (FIG. 3). Despite the fact that this construct contained most of the ACE2 and mAb 80R contact residues, no substantial binding for either ACE2 or mAb 80R was demonstrated.

Figure 4A:
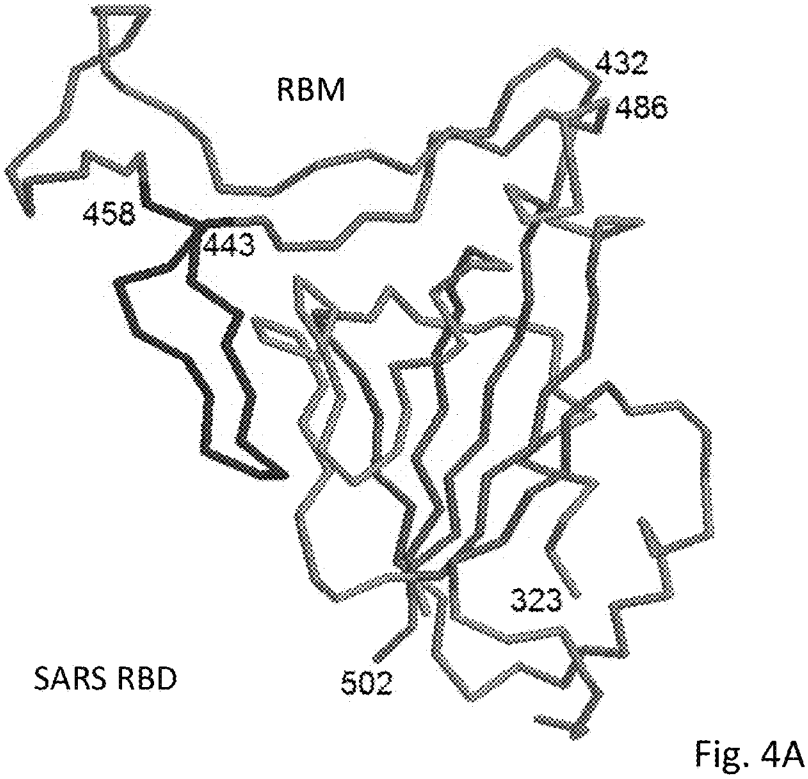
FIG. 4A-4E. Illustration, sequence analysis and screening of SARS CoV RBM linker-libraries
Figure 4B:
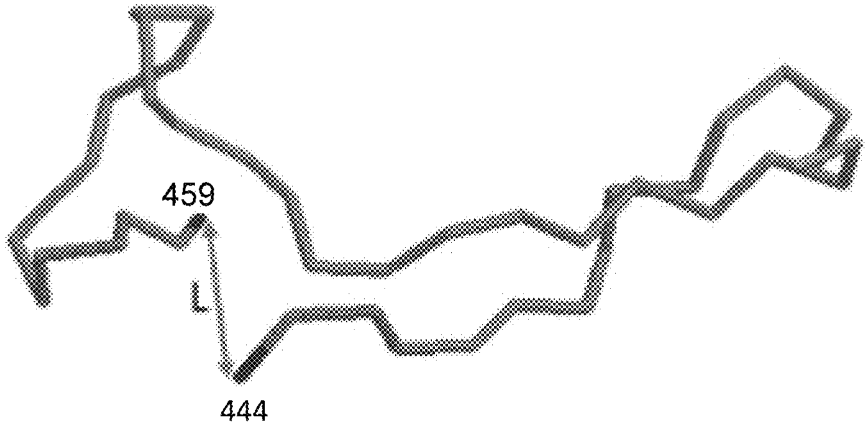

In view of the fact that the 16-amino acid loop (residues R444-F459, also denoted by SEQ ID NO: 2) located within the RBM does not contribute any contacts with the ligands and presumably functions only to tack RBM to the core of RBD, the inventors hypothesized that it might cause some interference in the correct folding of the isolated binding surface. As a result, the inventors removed the loop thus generating a 7 Å gap between residues L443 and F460 (FIG. 3). The RBD and the respective RBM formed after loop deletion are schematically shown in FIG. 4A and in FIG. 4B, respectively (where the residues 444 and 459 are indicated). Simple closure of the gap by juxtaposing L443 directly to F460 did not produce a recognizable structure. Furthermore, introduction of one, two, three or four glycine residues to bridge between L443 and F460, closing the gap with multiple glycine-linkers, was also ineffective in generating a functional RBM.

Consequently, the inventors developed an empirical strategy proposing to identify functional linkers through affinity-selection. Thus, the inventors used mAb 80R as a probe to screen the "loop less" RBM containing combinatorial linkers to bridge the L443/F460 gap. For this, all possible linkers of 1 through 4 residues were constructed and tested for mAb 80R binding. The inventors' rationale was that linkers consisting of 1-4 amino acids in length and comprised of all possible amino acid compositions would generate a comprehensive library of RBM conformers. Screening this library with mAb 80R would allow to affinity-select those constructs harboring a "correct" (suitable) linker length and composition that enables reconstitution of a functional binding surface. The cloning strategy used to construct the linker libraries and a summary of the library complexities are given in the Materials and Methods and in FIG. 3, respectively.

Example 3

Figure 4D:
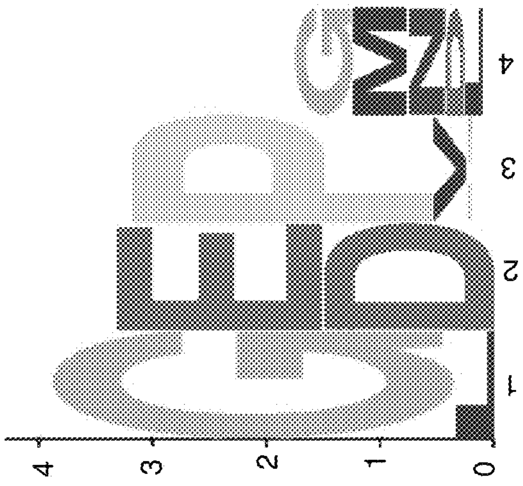
Figure 4C:
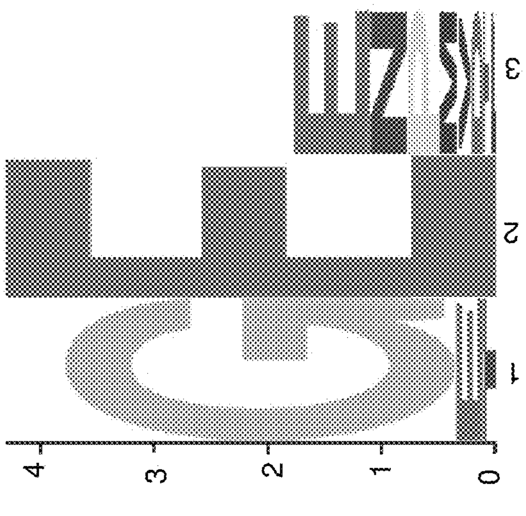

Analysis of SARS CoV RBM Linker-Libraries and Binding of Affinity-Selected Phages to mAb 80R No mAb 80R binders were selected from screening libraries of 1-mer and 2-mer random linkers. Therefore, the inventors concluded that although the entire theoretical complexity of linkers of 1 or 2 amino acids most probably was tested, none were able to effectively position the RBM-derived segments to assume a functional conformation. However, numerous positive clones were affinity-selected from both the 3 and 4-mer linker libraries. The amino acid sequences of the functional linkers were determined and compared as is illustrated in FIGS. 4C, 4D. Of a total of 800 colonies of phage variants screened from the 3-mer and 4-mer linker libraries, 45 positive clones were identified representing 16 unique linkers. Most of the mAb 80R-selected linkers contained a glycine residue in the first position and a negatively charged E or D at position 2. For the 3-mer linkers there was a propensity for residues E, N, P or M for the third position. The third position for the 4-mer linkers was typically P and greater variation for position 4 existed as is illustrated in FIGS. 4C, 4D. Exemplary linkers have the amino acid sequences GEM, EEP, GEE, GEN, GDPM, GDPN, GEVD, GEPL, GEPG, GDPG, GEPM. The amino acid sequences of four amino acid long linker are denoted by SEQ ID NOs: 9, 10, 11, 12, 39, 40 and 41, respectively.

Figure 4E:
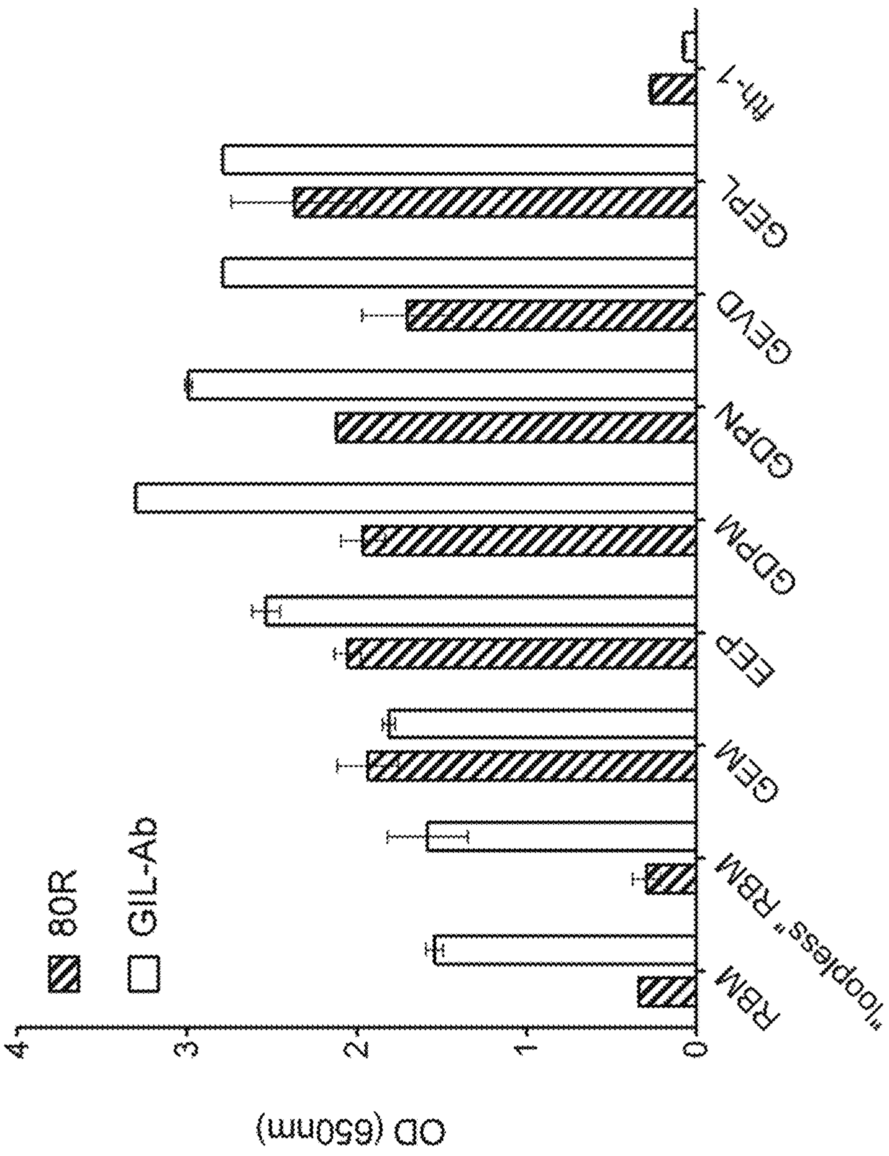

FIG. 4E shows the comparative binding of mAb 80R to the various constructs comprising the above linkers. In order to enable meaningful comparison it was first necessary to confirm that the constructs expressed equally on the phage surface. To this end, the inventors probed the different phages containing various constructs with the GIL-Ab reagent (Kaplan and Gershoni 2012), that specifically quantifies the level of recombinant pVIII in the bacteriophage, thus showing the expression of the constructs per se as compared to their ability to bind mAb 80R (FIG. 4E). This analysis yielded that all constructs are expressed well on the phage surface. Lack of binding was not due to lack of expression, as can be seen by comparing the binding of the initial RBM and "loop less" RBM constructs to the GEM construct which are expressed in similar levels, however bind to mAb 80R very differently.

Example 4

Figure 5:
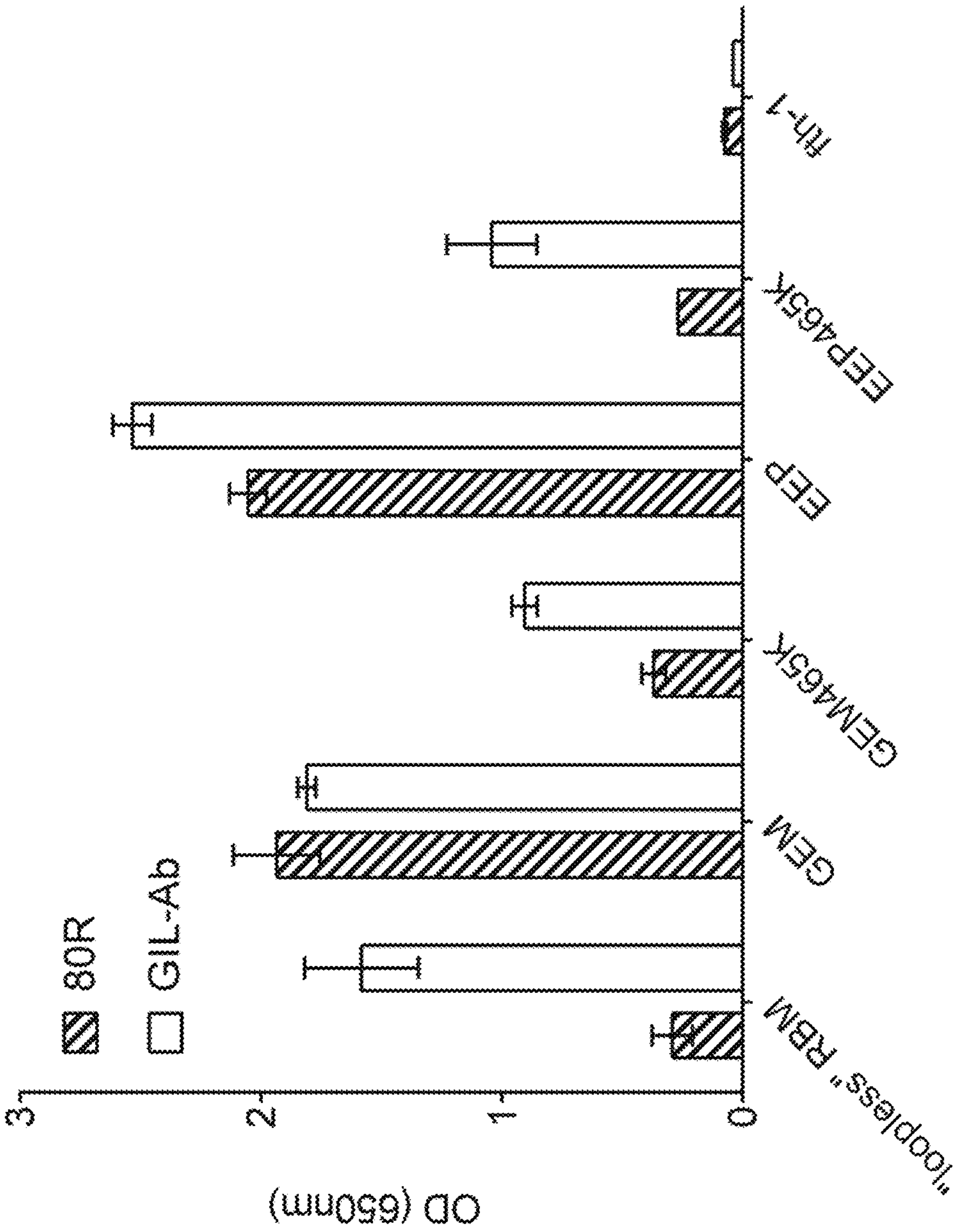
FIG. 5. The impact of the K465I mutation on expression and binding of affinity-selected phages to mAb 80

The Impact of the K465I Mutation in SARS CoV RBM on Expression and Binding of Affinity-Selected Phages mAb 80R During the course of these analyses, the inventors discovered a spontaneous point mutation at residue 465 from K to I (K465I) in some of the selected constructs. The mutated residue is not a contact residue for ACE2 or mAb 80R, this mutation however seemed to improve binding of mAb 80R for some of the linkers. The inventors discovered that reverting the K465I mutation to wild type (i.e. replacing the aliphatic methyl of isoleucine to the original positive charge of lysine at position 465) have led to a drop in binding activity for the two linkers tested, GEM465K and EEP465K (FIG. 5). No gain of binding was seen when the K465I mutation was introduced into the initial RBD construct (data not shown). The inventors further noticed that reversal of the mutation for both positively selected constructs GEM and EEP resulted in a decrease of construct expression, as is indicated by GIL-Ab binding in FIG. 5. On which basis, the inventors concluded that K465I mutation is beneficial for mAb 80R binding and for the affinity selection of those phages containing it.

Example 5

Binding of mAB 80R Affinity-Selected Phages Comprising SARS CoV RBM Constructs to the ACE Receptor From mAb 80R, the inventors tested the panel of functional RBM constructs against an additional "antibody ligand", the neutralizing anti-SARS mAb 11A, which also competes for ACE2 binding. This antibody was isolated using RBD from the late SARS CoV viral isolate, Guang Dong 03. Also in this case the inventors found that RBM harboring the GEM linker was specifically bound by mAb 11A. In view of this experiments, the inventors proceeded to test whether mAb 80R-selected phages can bind to the SARS CoV natural receptor—Angiotensin-Converting Enzyme 2 (ACE2), thus proving further the bi-functional nature of the reconstituted structure (FIG. 6). Five out of six linkers tested, with the exception of EEP linker, bound ACE2 well, with GEM being the best binder.

Example 6

Design of MERS CoV RBM Constructs

The above protocol, which proved to be effective for SARS CoV RBD, was applied, with certain modifications, to achieve reconstitution of the MERS-RBM. As can be seen in FIG. 9A the MERS CoV RBD (Chen et al. 2013), which is a segment of the Spike protein, consists of a core structure harboring five beta strands (depicted in red) and a 70 aa excursion that lies juxtaposed along the core (orange, residues 493-564, SEQ ID N. 42). This feature is recognized by the receptor huDPP4 (also known as CD26, Chen et al. 2013) and a variety of neutralizing antibodies (nAbs), for example the monoclonal antibody m336 (Ying, T. et al. 2015; Ying et al. 2014; Yu et al. 2015) and thus constitutes the receptor binding motif (RBM). From this excursion extends a looped structure (FIG. 9A, 514-527, blue) that does not provide contacts with viral ligands but rather serves to tack the RBM to the core through hydrogen bonding.

The atomic structure of the MERS CoV RBD bound to the CD26 (huDPP4) receptor is demonstrated in FIG. 8. The core of the RBD supports an excursion, RBM, containing a 14aa loop. As evident from FIG. 8 and as detailed above, the loop does not directly contribute to the recognition of the CD26 receptor. The binding interface between the monoclonal antibody mAb m336 and the RBM of MERS CoV is demonstrated in FIG. 10. As evident from the binding interface, the contact is primarily between the mAb CDR loops and the β strand 7, with the significant contact residues being W535, E536, Y540 and R542 of β strand 7 and W553 of β strand 8.

In view of the structure of the RBD and the interactions formed between the RBM and its ligands, expression of the RBM, devoid of the loop, serves as a scaffold for the functional reconstitution of the RBM. FIGS. 9B, 9C and FIG. 9D depict an exemplary reconstituted RBM structure, based on expression of residues 492-514 and 527-565 (as denoted by SEQ ID NO: 8 and SEQ ID NO: 18, respectively) or based on expression of residues 493-514 and 527-564 (as denoted by SEQ ID NO: 44 and SEQ ID NO: 45) as illustrated in FIG. 9A. In yet another alternative, a construct for the expression of residues 491-567 (also denoted by SEQ ID NO: 13), while deleting the 14aa loop (residues 515-529, denoted by SEQ ID NO: 14) was prepared. The gap thus generated is bridged by a specific linker, which length and composition is determined using a library of combinatorial linkers containing all possible amino acids compositions and spanning lengths from 1-10 amino acid residues long, as described herein above. The selection of functional RBM structures is accomplished by screening the combinatorial library of conformers with the neutralizing antibodies directed against the MERS CoV RBD and as well as by its receptor. Further alternative MERS CoV RBM constructs are described in Example 7 below.

It is noteworthy that residue 503 of the RBM is naturally a cysteine residue that disulfide bonds with the residue cysteine 526 (which is deleted). Therefore, the linker design shown in FIG. 9C is prepared in which a cysteine residue is introduced in the linkers. The construction of the linkers is based on the above protocol, namely on introducing NNK codons for those positions intended to express any of the 20 amino acids. For the central position to be biased for cysteine in addition to the other 19 residues, NNK is mixed with an equal amount of TGT codon, in order to ensure better than 50% chance for incorporation of a cysteine residue in a central position flanked by totally random sequences on either side.

Simpler libraries may also be considered such as that suggested in FIG. 9E in which only the loop 538-559 (denoted by SEQ ID NO: 83) which contacts both the huDPP4 and various nAbs is expressed. For this a short 2-5 residue random linker bridging residues 545-552 will be introduced to replace the native sequence, linking segments 538-545 (SEQ ID NO: 46) and 552-559, SEQ ID NO: 47). It is noteworthy that both the full RBM and the smaller loop are extensively hydrogen bonded (FIG. 9D and FIG. 9E) and thus it is expected that expressing the segments in the proper orientation and register should allow them to "zip-up" and assume the correct fold as is the case of SARS CoV.

Example 7

Constructions of MERS CoV RBM Random Libraries Comprising Multiple Linkers

The essence of the construction was focused on β strand 7 that contacts for example the human receptor dipeptidyl peptidase 4 (hDPP4) and also the neutralizing mAb m336, as described above. The construction strategy of MERS CoV RBM random libraries focused on the β strand 7 and on preserving the contact residues W535, E536, Y540 and R542 of (3 strand 7, as illustrated in FIG. 10. However, expression of β7 alone (the upper-most strand) would not conform to a physiologically functional conformation. In order to enable reconstitution of a functional conformation, the β strand 8 was also included in the construct. The β strand 8 hydrogen bonds with β strand 7 and thus holds the strand in place and enables the orientation of the required contact residues. Strands β7 and β8 are the red and blue strands, respectively, depicted in FIG. 11A and FIG. 11B and demonstration of a construct based on β strand 7 and β strand 8 is illustrated in FIG. 11C. The library consisted of introducing a linker sequence connecting residue 546 (the C-terminal region of β strand 7) with residue 551 (the N-terminal region of β strand 8), as schematically illustrated in FIGS. 11*d*, 11E and in FIGS. 12A and 12B (FIG. 12A is identical to FIG. 11E and appears for easy reference). The linkers prepared were of a length of one (1) through five (5) NNK nucleotides of totally random sequences coding for random one to five amino acid residues linkers.

Moreover, in some of the constructs random linkers having a length of one to three NNK nucleotides of totally random sequences coding for random one to three amino acid residues were introduced at either end of the constructs described above (namely 0-3 NNK sequences at each end). In order to achieve the above combinatorial complexity the approach illustrated in FIG. 12 was taken, as follows. Single stranded DNA oligonucleotides that correspond to the amino acid sequences of the β strands 7 and 8 were constructed. The amino acid sequences thereof are depicted in red and blue in FIG. 12A, 12B, respectively and are denoted by SEQ ID NO: 37 and SEQ ID NO: 38. Each one of the oligonucleotides differed from the rest in the number of NNK linkers used to connect residues 546 to 551, hence five types of oligonucleotides with one, two, three, four or five (1, 2, 3, 4 or 5) random NNK repeats were prepared.

In order to produce double-stranded DNA templates (dsDNA) for PCR, a single antisense 20 bases-long oligonucleotide was used to prime a Klenow fragment DNA polymerase fill-in reaction, thus producing five of distinct templates. Synthesis of the complementary strand by Klenow fragment is illustrated for example in FIG. 12C and the dsDNA thus formed is illustrated in FIG. 12D.

Then, the templates were amplified by PCR reactions using 5' and 3' forward (F) and reverse (R) primers, as illustrated in FIG. 12E. The forward and reverse primers contained 1, 2 or 3 NNK repeats linkers in their 5' end or no NNK at all. Thus there were four (4) different forward and four (4) different reverse primers. The PCR reaction was ran in five separate reactions that differ only in the template used (1-5 NNKs described above), where all of the primers (4 forward and 4 reverse primers) were used in a single mix together. Thus a total of 5 reactions were ran simultaneously yielding a total of 80 different possible random conformer libraries (4×4×5).

The PCR products were then cloned into the Sfi1 sites of precut fth1 vector as described above, via Gibson assembly. Three clones from each linker library (containing linkers with 1, 2, 3, 4 or 5 NNK linkers) were selected and sent to sequencing and 12 clones gave correct in frame sequences with various linkers preceding or following the insert. As is seen in Table 2, the internal linker length correctly corresponded to the library from which it was produced. Moreover, the preceding and following linkers demonstrated samples of 0, 1, 2 and 3 NNK codons. Examples for the various amino acid sequences encoded by the above described sequences are listed in Table 2 below.

TABLE 2

Sequences of 15 randomly selected clones

| #NNK | 5' NNK | Linker NNK | 3' NNK | SEQ ID NO: |
|---|---|---|---|---|
| 5 | CF | WEDGDYYRKQLS-GFDEQ-GGWLVASGST | QLT | 48 |
| | | WEDGDYYRKQLS-PYNYH-GGWLVASGST | | 50 |
| | | WEDGDYYRKQLS-SQAPL-GGWLVASGST | | 52 |
| 4 | | no sequence | | |
| | LG | WEDGDYYRKQLS-LHLP-GGWLVASGST | IRK | 54 |
| | | WEDGDYYRKQLS-VVAT-GGWLVASGST | | 56 |

TABLE 2-continued

Sequences of 15 randomly selected clones

| #NNK | 5' NNK | Linker NNK | 3' NNK | SEQ ID NO: |
|---|---|---|---|---|
| 3 | | no sequence | | |
| | FQS | WEDGDYYRKQLS-VYS-GGWLVASGST | LQ | 58 |
| | | no sequence | | |
| 2 | | WEDGDYYRKQLS-RQ-GGWLVASGST | | 59 |
| | | WEDGDYYRKQLS-SY-GGWLVASGST | PT | 60 |
| | | WEDGDYYRKQLS-FS-GGWLVASGST | RTK | 61 |
| 1 | SIR | WEDGDYYRKQLS-C-GGWLVASGST | RTK | 62 |
| | | WDDGDYYRKQLS-C-GGWLVASGST | LP | 63 |
| | A | WEDGDYYRKQLS-Y-GGWLVASGST | | 64 |

As shown in Table 2, a MERS CoV receptor binding motif-linker constructs comprise amino acid sequences of the β strands 7 and 8, separated by one, two, three, four or five amino acid residues (encoded by the inner linker described above). In addition, some of the constructs further comprise at least one terminal linker which comprises at least one amino acid residue.

For example, the MERS CoV receptor binding motif-linker construct denoted by SEQ ID NO: 58 comprises an N-terminal linker having the amino acid sequence FQS, followed by the amino acid sequences of the β strand 7 and 8 (WEDGDYYRKQLS and GGWLVASGST, denoted by SEQ ID NO: 37 and SEQ ID NO: 38, respectively) separated by the inner linker having the amino acid sequence VYS and followed by the terminal linker having the amino acid sequence LQ.

The amino acid sequences of the various linkers and of the β strands 7 and 8 are denoted by SEQ ID NO: 48, 50, 52, 54, 56, 58, 59, 60, 61, 62, 63, 64.

The isolated conformers are then assayed for binding (for example to the DPP4 receptor or to the m336 antibody) and conformers suitable for subsequent assays are identified, as further detailed below.

Example 8

Screening the Libraries and Selection of Functional Constructs

Once the construct libraries of MERS are produced they are screened against the viral receptor protein huDPP4 and a panel of suitable neutralizing antibodies (nAbs). The recombinant receptor-protein is readily available through a number of commercial suppliers (e.g., Sigma/Aldrich, Sino Biological Inc., ProSpec and RayBiotech). Alternatively, it can be expressed in house with a C-terminal His Tag (residues 39-766) as previously published (Du et al. 2014). Finally, a third option would be to screen using DPP4-expressing Huh-7 cells as bait (Ying et al. 2014).

Two panels of nAbs (a total of 10 different antibodies, Ying et al. 2014; Tang et al. 2014) in mg quantities are available for screening. It is important to emphasize that each binding ligand, receptor or nAb, has its unique idiosyncrasies and demands for binding. Thus for example, much of the contacts for DPP4 reside in strand 537-545 (FIG. 9C, red, denoted by SEQ ID NO: 21) while all three strands contact the heavy chain of nAb m336 isolated by Dimitrov and colleagues (Ying et al. 2014). The panel of 7 nAbs isolated by the Marasco Lab recognizes 3 overlapping epitopes (defined by nAbs 1E9, 1F8 and 3B11 respectively (Tang et al. 2014)). Thus screening with a diversity of probes should drive the selection of reconstituted constructs that faithfully represent detailed nuances of the native conformation. Thus the ultimate RBM's to be taken for further development to immunogens will be ranked by their ability to be bound by more than one defining probe. This has already proven to be an effective approach for the SARS CoV where the inventors used three different probes to characterize the various RBMs obtained as described above (Freund et al. 2015).

Example 9

Production of Reconstituted Immunogens

Ultimately, the discovery of functional CoV RBM constructs is translated into practical production of immunogens. To this end, two approaches are taken; the production of recombinant constructs and the chemical synthesis of peptide immunogens. Although the CoV RBMs are selected via phage-display as described above, their implementation as immunogens requires a more refined and less complex presentation. This is achieved by expressing them as fusion proteins using various scaffolds. For this the inventors introduced the RBM sequence at the C-terminus of the N-terminal HIS tagged MBP using the pMALc-NHNN vector. Moreover, flanking the insert with asymmetric AvaI sites (TCTGGG) allowed the inventors to isolate a series of 1-5 tandem repeats of the RBM. Such multimeric constructs may improve their immunogenicity in vivo. Hence, the SARS and MERS CoV RBM are expressed as MBP fusions. In addition, the RBM inserts of the most successful MBP constructs are cloned into a second scaffold using glutathione Stransferase (pGEX expression vector (Smith, D. B., and K. S. Johnson. 1988). This promotes more efficient focus of the immune response towards the insert of interest in serially boosted animals.

The production of chemically synthesized RBM constructs is also considered. Thus the production of synthetic RBM may be advantageous as it could benefit from the use of specific backbone cross linking and other specific chemistries to stabilize the construct into its physiological conformation. Moreover, the selected introduction of D-amino acids at strategic positions may increase the half-life of the immunogen. Polymerization using dendrimers may also provide a more efficacious immunogen and therefore will also be considered.

Example 10

Immunization Studies

Once produced, the immunogens are characterized first for their ability to efficiently bind their cognate ligands, namely huDPP4 and nAbs for MERS CoV. The most active immunogens (i.e., best recognized by their ligands) are then used in animal immunization studies. Moreover, two control immunogens are tested, as follows. First, a construct harboring a linker that fails to reconstitute a functional RBM thus providing a "negative control RBM" is used. This will represent the presence of the identical RBM segments yet in a dysfunctional, denatured conformation. Such a control is imperative as it enables to survey the production of antibodies that are truly conformation-dependent and thus have the highest chance to effectively recognize the native antigen and neutralize the virus. Next, full length RBD, RBD-hFc (51349-590 (Tang et al. 2014)) or a more focused RBD S377-588-Fc (Ma et al. 2014)) which will serve as a "positive control immunogen" that provides the baseline response towards the RBM as part of the entire RBD are tested. The general scheme is depicted in FIG. 13.

In view of the fact that we intend to comprehensively analyze the humoral response towards the RBM constructs rabbits are used so to ensure ample amounts of polyclonal sera from each animal and immunization regimen tested. The general format is multi-armed studies in groups of 4-5 animals for each arm. Pre-immune serum is collected one week prior immunization for each animal. The initial immunization is MBP-RBM for which a number of RBM variants are tested, each with different linkers which could result in diverse binding characteristics. Arms for the positive and negative control immunogens are also tested.

Following an MBP-construct boost, animals are boosted with GST-constructs and sera is collected 2 weeks after each immunization. All the animals are sacrificed by exsanguination at 16 weeks for final blood collection. All injections and exsanguinations are performed by the University Veterinarian at the animal housing facility in accordance with the Ministry of Health approval. In the event that chemically synthesized RBMs meet the criteria for potentially effective immunogens (i.e., recognized and efficiently bind huDPP4 and nAbs) immunization of rabbits with dendrimers are performed as well.

Example 11

Serum Analyses

The polyclonal sera collected from each animal undergoes a series of immunoassays to critically evaluate the efficacy of immunization regimens and potential utility of each RBM tested as a vaccine-lead for future development for human use. Serum collected at each time point is tested by ELISA to determine the specificity and titer raised against the RBM. ELISA tests using the phage displayed RBM as plated antigen gives an indication of the specific response towards the RBM moiety as opposed to the antibodies mounted against the MBP or GST carrier proteins. Moreover, use of recombinant RBD-hFc (S1349-590, Tang et al. 2014) as the plated antigen indicates the degree of cross reactivity with viral antigen as opposed to reconstituted RBM. These activities are compared to the binding of sera derived from rabbits immunized with the positive and negative controls.

Neutralization assays are conducted using VLP/Luciferase assays, plaque reduction neutralization tests and inhibition of cytopathic effects (Ying et al. 2014; Tang et al. 2014). For each of these assays the extent of inhibition of infections is measured for the polyclonal sera collected for each animal and immunization scheme for the various RBM constructs. Finally, systematic IgOme profiling (Ryvkin et al. 2012; Weiss-Ottolenghi, Y., and J. M. Gershoni. 2013) is performed at the beginning (preimmune) and end point for each rabbit used. These tests provide high resolution profiles of the complexities of antibodies mounted in the different regimens to be examined. IgOme profiling also allows to evaluate the degree of successful focusing of the response to the RBM as compared to the RBM specific response generated when using intact RBD as the vaccine.

The invention claimed is:

1. A polypeptide comprising an amino acid sequence of at least one reconstituted Receptor Binding Motif (RBM) of a Spike protein of a Coronavirus (CoV) or of any fragment thereof, wherein said reconstituted RBM comprises at least one non-native linker and at least two fragments of the native RBM, said native RBM is a 30 to 200 amino acid sequence comprised within the Receptor Binding Domain (RBD) of said Spike protein forming a binding interface that interacts with the viral receptor, wherein said native RBM forms an extended 30 to 100 or more amino acid excursion juxtaposed along the edge of the core of the RBD and tacked to said core via a loop, and wherein at least one of said linker/s replaces or is added to at least one of: said loop, any part or amino acid residue/s thereof and any RBM fragment or amino acid residue/s thereof.

2. The polypeptide according to claim 1, wherein said spike protein of a CoV is 51 protein of a CoV, said CoV is capable of infecting mammalian subject/s, avian subject/s or any other vertebrates.

3. The polypeptide according to claim 2, wherein said CoV is Middle East Respiratory Syndrome coronavirus (MERS CoV), and wherein said native RBM comprises any one of: (a) residues 498 to 562 of the amino acid sequence of MERS-CoV Spike protein as denoted by SEQ ID NO: 34; (b) residues 498 to 562 of the amino acid sequence as denoted by SEQ ID NO: 34, with at least one flanking amino acid residue/s; or (c) any fragments thereof, and wherein said loop comprises any one of: (d) residues 515 to 527 of the amino acid sequence of MERS-CoV Spike protein as denoted by SEQ ID NO: 34; (e) residues 515 to 527 of the amino acid sequence as denoted by SEQ ID NO: 34, with at least one flanking amino acid residue/s; or (f) any fragments thereof.

4. The polypeptide according to claim 3, wherein the reconstituted RBM comprises:

(a) at least one linker and wherein at least one of said linker/s replace/s said loop or any part thereof; or (b) at least one linker and wherein at least one of said linker/s replace/s at least one RBM fragment or amino acid residue/s not directly involved in receptor binding.

5. The polypeptide according to claim 2, wherein said CoV is Severe Acute Respiratory Syndrome coronavirus (SARS CoV), and wherein said native RBM comprises residues 432 to 486 of the SARS-CoV Spike protein as denoted by SEQ ID NO: 3, and wherein said loop comprises residues 444 to 459 of the SARS-CoV Spike protein as denoted by SEQ ID NO: 2.

6. The polypeptide according to claim 5, wherein the reconstituted RBM comprises at least one linker, and wherein at least one of said linker/s replaces said loop, or any part thereof.

7. The polypeptide according to claim 6, wherein said linker comprises the amino acid sequence of $Xaa_{(n)}$-$Xaa^2$-$Xaa^3$-$Xaa^4$-$Xaa_{(n)}$ as denoted by SEQ ID NO: 27 or any fragment thereof, wherein Xaa is any amino acid and n is zero or an integer of from 1 to 5, and wherein:

$X^2$, is a Gly, Glu, Leu or Thr;

$X^3$, is Glu or Asp; and $X^4$, is Glu, Asn, Pro, Met, Val or Asp.

8. The polypeptide according to claim 7, wherein said linker comprises the amino acid sequence of $Xaa^1$-$Xaa^2$-$Xaa^3$ or any fragment thereof, wherein Xaa is any amino acid, and wherein:

$X^1$, is a Gly, Glu or Thr;

$X^2$, is Glu; and $X^3$, is Glu, Asn, Pro, Met, Val or Asp.

9. The polypeptide according to claim 8, wherein said linker comprises the amino acid sequence of any one of:

Gly-Glu-Met, as denoted by SEQ ID NO: 7 and Glu-Glu-Pro, as denoted by SEQ ID NO: 8.

10. The polypeptide according to claim 7, wherein said linker comprises the amino acid sequence of $Xaa^1$-$Xaa^2$-$Xaa^3$-$Xaa^4$ as denoted by SEQ ID NO: 29 or any fragment thereof, wherein Xaa is any amino acid, and wherein:

$X^1$, is a Gly or Leu;

$X^2$, is Glu or Asp; and $X^3$, is Pro, Val or Gly; and $X^4$, is Gly, Met, Asn, Asp or Leu.

11. The polypeptide according to claim 10, wherein said linker comprises the amino acid sequence of any one of:

Gly-Asp-Pro-Met, as denoted by SEQ ID NO: 9, Gly-Asp-Pro-Asn as denoted by SEQ ID NO: 10, Gly-Glu-Val-Asp as denoted by SEQ ID NO: 11 and Gly-Glu-Pro-Leu, as denoted by SEQ ID NO: 12.

12. The polypeptide according to claim 5, wherein said reconstituted SARS-CoV RBM comprises residues $_{432}STGNYNYKYRL_{443}$ as denoted by SEQ ID NO: 5 and $_{460}FSPDGKPCTPCTPPALNCYWPLNDYGFYTT_{486}$ as denoted by SEQ ID NO: 6 or any fragments, mutants or derivatives thereof, linked by said at least one linker that replaces the loop or any parts thereof.

13. The polypeptide according to claim 12, wherein said reconstituted SARS-CoV RBM is a mutated RBM having a K465I mutation, said RBM comprises residues $_{432}$STGNYNYKYRL$_{443}$ as denoted by SEQ ID NO: 5 and $_{460}$FSPDGIPCTPCTPPALNCYWPLNDYGFYTT$_{486}$ as denoted by SEQ ID NO: 30 or any fragments or derivatives thereof, linked by said at least one linker that replaces the loop or any parts thereof.

14. The polypeptide according to claim 1, or any derivative, enantiomer, fusion protein, conjugate or polyvalent dendrimer thereof, comprised in a composition or an epitope based CoV vaccine, said composition or vaccine optionally further comprises at least one pharmaceutically acceptable carrier/s, excipient/s, auxiliaries, and/or diluent/s.

15. A method for preventing, inhibiting, reducing, eliminating, protecting or delaying the onset of an infection or an infectious clinical condition caused by coronavirus, or of inducing an immune response against a coronavirus, in a subject in need thereof, the method comprising the step of administrating to said subject an effective amount of at least one polypeptide comprising an amino acid sequence of at least one reconstituted RBM of CoV Spike protein or of any fragment thereof, any derivative, enantiomer, fusion protein, conjugate or polyvalent dendrimer thereof or of any composition or vaccine comprising the same, wherein said reconstituted RBM comprises at least one linker and at least two fragments of the native RBM, said native RBM is a 30 to 200 amino acid sequence comprised within the RBD of said Spike protein forming a binding interface that interacts with the viral receptor.

16. The method according to claim 15, wherein said CoV is capable of infecting mammalian subject/s, avian subject/s or any other vertebrates, said coronavirus is any one of MERS CoV and SARS-CoV.

17. A method for the preparation of a functional reconstituted RBM of Spike protein of a CoV, said method comprises the step of:
a) providing a conformer library of RBMs of said Spike protein of a CoV, comprising plurality of bacteriophages, each expressing a reconstituted RBM comprising an amino acid sequence of at least two fragments of an RBM of a viral Spike protein of a CoV and at least one exogenous combinatorial linker;
b) screening said library with a binding molecule; and
c) identifying and producing reconstituted RBM peptides which bind at least one of said binding molecules.

18. The method according to claim 17, wherein said spike protein of a CoV is a 51 protein of CoV, and wherein said binding molecule is at least one of: (a) the receptor for said CoV or any fragments thereof; (b) a neutralizing antibody directed against the wild type CoV RBM and any combinations thereof.

19. The method according to claim 18, wherein:
(a) said CoV RBM is MERS CoV RBM, and said receptor is CD26/DPP4 or any fragment thereof; or
(b) wherein said CoV RBM is SARS CoV RBM, and said receptor is Angiotensin-Converting Enzyme 2 (ACE2) or any fragment thereof.

20. The method according to claim 17, for producing epitope based CoV vaccine comprising reconstituted RBM, the method further comprising the step of: admixing at least one of said reconstituted functional RBM/s of a CoV Spike protein identified and produced by step (c), or any derivative or enantiomer thereof, or any fusion protein, conjugate, or polyvalent dendrimer comprising the same with at least one adjuvant/s, carrier/s, excipient/s, auxiliaries, and/or diluent/s.

* * * * *

SEQUENCE LISTING

```
<160> NUMBER OF SEQ ID NOS: 110

<210> SEQ ID NO 1
<211> LENGTH: 80
<212> TYPE: PRT
<213> ORGANISM: Artificial Sequence
<220> FEATURE:
<223> OTHER INFORMATION: SARS L421 through S500

<400> SEQUENCE: 1

Leu Ala Trp Asn Thr Arg Asn Ile Asp Ala Thr Ser Thr Gly Asn Tyr
1               5                   10                  15

Asn Tyr Lys Tyr Arg Tyr Leu Arg His Gly Lys Leu Arg Pro Phe Glu
            20                  25                  30

Arg Asp Ile Ser Asn Val Pro Phe Ser Pro Asp Gly Lys Pro Cys Thr
        35                  40                  45

Pro Pro Ala Leu Asn Cys Tyr Trp Pro Leu Asn Asp Tyr Gly Phe Tyr
    50                  55                  60

Thr Thr Thr Gly Ile Gly Tyr Gln Pro Tyr Arg Val Val Val Leu Ser
65                  70                  75                  80


<210> SEQ ID NO 2
```

-continued

<211> LENGTH: 16
<212> TYPE: PRT
<213> ORGANISM: Artificial Sequence
<220> FEATURE:
<223> OTHER INFORMATION: SARS RBM R444-P459

<400> SEQUENCE: 2

Arg His Gly Lys Leu Arg Pro Phe Glu Arg Asp Ile Ser Asn Val Pro
1 5 10 15

<210> SEQ ID NO 3
<211> LENGTH: 55
<212> TYPE: PRT
<213> ORGANISM: Artificial Sequence
<220> FEATURE:
<223> OTHER INFORMATION: SARS RBM region S432-T486

<400> SEQUENCE: 3

Ser Thr Gly Asn Tyr Asn Tyr Lys Tyr Arg Tyr Leu Arg His Gly Lys
1 5 10 15

Leu Arg Pro Phe Glu Arg Asp Ile Ser Asn Val Pro Phe Ser Pro Asp
20 25 30

Gly Lys Pro Cys Thr Pro Pro Ala Leu Asn Cys Tyr Trp Pro Leu Asn
35 40 45

Asp Tyr Gly Phe Tyr Thr Thr
50 55

<210> SEQ ID NO 4
<211> LENGTH: 51
<212> TYPE: PRT
<213> ORGANISM: Artificial Sequence
<220> FEATURE:
<223> OTHER INFORMATION: SARS RBM residues Y436-T486

<400> SEQUENCE: 4

Tyr Asn Tyr Lys Tyr Arg Tyr Leu Arg His Gly Lys Leu Arg Pro Phe
1 5 10 15

Glu Arg Asp Ile Ser Asn Val Pro Phe Ser Pro Asp Gly Lys Pro Cys
20 25 30

Thr Pro Pro Ala Leu Asn Cys Tyr Trp Pro Leu Asn Asp Tyr Gly Phe
35 40 45

Tyr Thr Thr
50

<210> SEQ ID NO 5
<211> LENGTH: 11
<212> TYPE: PRT
<213> ORGANISM: Artificial Sequence
<220> FEATURE:
<223> OTHER INFORMATION: SARS RBM residues S432-L443

<400> SEQUENCE: 5

Ser Thr Gly Asn Tyr Asn Tyr Lys Tyr Arg Leu
1 5 10

<210> SEQ ID NO 6
<211> LENGTH: 30
<212> TYPE: PRT
<213> ORGANISM: Artificial Sequence
<220> FEATURE:
<223> OTHER INFORMATION: SARS RBM residues F460-T486

<400> SEQUENCE: 6

Phe Ser Pro Asp Gly Lys Pro Cys Thr Pro Cys Thr Pro Pro Ala Leu

-continued

```
1               5                   10                  15

Asn Cys Tyr Trp Pro Leu Asn Asp Tyr Gly Phe Tyr Thr Thr
            20                  25                  30


<210> SEQ ID NO 7
<211> LENGTH: 16
<212> TYPE: PRT
<213> ORGANISM: Artificial Sequence
<220> FEATURE:
<223> OTHER INFORMATION: SARS RBM residues 443-458

<400> SEQUENCE: 7

Leu Arg His Gly Lys Leu Arg Pro Phe Glu Arg Asp Ile Ser Asn Val
1               5                   10                  15


<210> SEQ ID NO 8
<211> LENGTH: 23
<212> TYPE: PRT
<213> ORGANISM: Artificial Sequence
<220> FEATURE:
<223> OTHER INFORMATION: MERS Residues 492-514

<400> SEQUENCE: 8

Thr Lys Pro Leu Lys Tyr Ser Tyr Ile Asn Lys Cys Ser Arg Leu Leu
1               5                   10                  15

Ser Asp Asp Arg Thr Glu Val
            20


<210> SEQ ID NO 9
<211> LENGTH: 4
<212> TYPE: PRT
<213> ORGANISM: Artificial Sequence
<220> FEATURE:
<223> OTHER INFORMATION: Linker

<400> SEQUENCE: 9

Gly Asp Pro Met
1


<210> SEQ ID NO 10
<211> LENGTH: 4
<212> TYPE: PRT
<213> ORGANISM: Artificial Sequence
<220> FEATURE:
<223> OTHER INFORMATION: Linker

<400> SEQUENCE: 10

Gly Asp Pro Asn
1


<210> SEQ ID NO 11
<211> LENGTH: 4
<212> TYPE: PRT
<213> ORGANISM: Artificial Sequence
<220> FEATURE:
<223> OTHER INFORMATION: Linker

<400> SEQUENCE: 11

Gly Glu Val Asp
1


<210> SEQ ID NO 12
<211> LENGTH: 4
<212> TYPE: PRT
<213> ORGANISM: Artificial Sequence
<220> FEATURE:
```

<223> OTHER INFORMATION: Linker

<400> SEQUENCE: 12

Gly Glu Pro Leu
1

<210> SEQ ID NO 13
<211> LENGTH: 77
<212> TYPE: PRT
<213> ORGANISM: Artificial Sequence
<220> FEATURE:
<223> OTHER INFORMATION: MERS Residues 491-567

<400> SEQUENCE: 13

Ile Thr Lys Pro Leu Lys Tyr Ser Tyr Ile Asn Lys Cys Ser Arg Leu
1 5 10 15

Leu Ser Asp Asp Arg Thr Glu Val Pro Gln Leu Val Asn Ala Asn Gln
20 25 30

Tyr Ser Pro Cys Val Ser Ile Val Pro Ser Thr Val Trp Glu Asp Gly
35 40 45

Asp Tyr Tyr Arg Lys Gln Leu Ser Pro Leu Glu Gly Gly Gly Trp Leu
50 55 60

Val Ala Ser Gly Ser Thr Val Ala Met Thr Glu Gln Leu
65 70 75

<210> SEQ ID NO 14
<211> LENGTH: 15
<212> TYPE: PRT
<213> ORGANISM: Artificial Sequence
<220> FEATURE:
<223> OTHER INFORMATION: MERS 14aa loop residues 515-529

<400> SEQUENCE: 14

Pro Gln Leu Val Asn Ala Asn Gln Tyr Ser Pro Cys Val Ser Ile
1 5 10 15

<210> SEQ ID NO 15
<211> LENGTH: 68
<212> TYPE: PRT
<213> ORGANISM: Artificial Sequence
<220> FEATURE:
<223> OTHER INFORMATION: MERS RBM residues 498-565

<400> SEQUENCE: 15

Ser Tyr Ile Asn Lys Cys Ser Arg Leu Leu Ser Asp Asp Arg Thr Glu
1 5 10 15

Val Pro Gln Leu Val Asn Ala Asn Gln Tyr Ser Pro Cys Val Ser Ile
20 25 30

Val Pro Ser Thr Val Trp Glu Asp Gly Asp Tyr Tyr Arg Lys Gln Leu
35 40 45

Ser Pro Leu Glu Gly Gly Gly Trp Leu Val Ala Ser Gly Ser Thr Val
50 55 60

Ala Met Thr Glu
65

<210> SEQ ID NO 16
<211> LENGTH: 86
<212> TYPE: PRT
<213> ORGANISM: Artificial Sequence
<220> FEATURE:
<223> OTHER INFORMATION: MERS RBM residues 483-568

<400> SEQUENCE: 16

```
Thr Val Pro His Asn Leu Thr Thr Ile Thr Lys Pro Leu Lys Tyr Ser
1               5                   10                  15

Tyr Ile Asn Lys Cys Ser Arg Leu Leu Ser Asp Asp Arg Thr Glu Val
            20                  25                  30

Pro Gln Leu Val Asn Ala Asn Gln Tyr Ser Pro Cys Val Ser Ile Val
        35                  40                  45

Pro Ser Thr Val Trp Glu Asp Gly Asp Tyr Tyr Arg Lys Gln Leu Ser
    50                  55                  60

Pro Leu Glu Gly Gly Gly Trp Leu Val Ala Ser Gly Ser Thr Val Ala
65                  70                  75                  80

Met Thr Glu Gln Leu Gln
                85


<210> SEQ ID NO 17
<211> LENGTH: 19
<212> TYPE: PRT
<213> ORGANISM: Artificial Sequence
<220> FEATURE:
<223> OTHER INFORMATION: MERS RBM loop residues 512-530

<400> SEQUENCE: 17

Thr Glu Val Pro Gln Leu Val Asn Ala Asn Gln Tyr Ser Pro Cys Val
1               5                   10                  15

Ser Ile Val


<210> SEQ ID NO 18
<211> LENGTH: 39
<212> TYPE: PRT
<213> ORGANISM: Artificial Sequence
<220> FEATURE:
<223> OTHER INFORMATION: MERS RBM Residues 527-565

<400> SEQUENCE: 18

Val Ser Ile Val Pro Ser Thr Val Trp Glu Asp Gly Asp Tyr Tyr Arg
1               5                   10                  15

Lys Gln Leu Ser Pro Leu Glu Gly Gly Gly Trp Leu Val Ala Ser Gly
            20                  25                  30

Ser Thr Val Ala Met Thr Glu
        35


<210> SEQ ID NO 19
<211> LENGTH: 9
<212> TYPE: PRT
<213> ORGANISM: Artificial Sequence
<220> FEATURE:
<223> OTHER INFORMATION: MERS RBM Residues 497-505

<400> SEQUENCE: 19

Tyr Ser Tyr Ile Asn Lys Cys Ser Arg
1               5


<210> SEQ ID NO 20
<211> LENGTH: 11
<212> TYPE: PRT
<213> ORGANISM: Artificial Sequence
<220> FEATURE:
<223> OTHER INFORMATION: MERS RBM Residues 552-562

<400> SEQUENCE: 20

Gly Trp Leu Val Ala Ser Gly Ser Thr Val Ala
1               5                   10
```

<210> SEQ ID NO 21
<211> LENGTH: 9
<212> TYPE: PRT
<213> ORGANISM: Artificial Sequence
<220> FEATURE:
<223> OTHER INFORMATION: MERS RBM Residues 537-545

<400> SEQUENCE: 21

Asp Gly Asp Tyr Tyr Arg Lys Gln Leu
1 5

<210> SEQ ID NO 22
<211> LENGTH: 10
<212> TYPE: PRT
<213> ORGANISM: Artificial Sequence
<220> FEATURE:
<223> OTHER INFORMATION: MERS residues 497-506

<400> SEQUENCE: 22

Tyr Ser Tyr Ile Asn Lys Cys Ser Arg Leu
1 5 10

<210> SEQ ID NO 23
<211> LENGTH: 9
<212> TYPE: PRT
<213> ORGANISM: Artificial Sequence
<220> FEATURE:
<223> OTHER INFORMATION: MERS residues 536-544

<400> SEQUENCE: 23

Glu Asp Gly Asp Tyr Tyr Arg Lys Gln
1 5

<210> SEQ ID NO 24
<211> LENGTH: 13
<212> TYPE: PRT
<213> ORGANISM: Artificial Sequence
<220> FEATURE:
<223> OTHER INFORMATION: MERS residues 553-565

<400> SEQUENCE: 24

Trp Leu Val Ala Ser Gly Ser Thr Val Ala Met Thr Glu
1 5 10

<210> SEQ ID NO 25
<211> LENGTH: 11
<212> TYPE: PRT
<213> ORGANISM: Artificial Sequence
<220> FEATURE:
<223> OTHER INFORMATION: MERS residues 515-525

<400> SEQUENCE: 25

Pro Gln Leu Val Asn Ala Asn Gln Tyr Ser Pro
1 5 10

<210> SEQ ID NO 26
<211> LENGTH: 191
<212> TYPE: PRT
<213> ORGANISM: Artificial Sequence
<220> FEATURE:
<223> OTHER INFORMATION: SARS RBD 319-509

<400> SEQUENCE: 26

Ile Thr Asn Leu Cys Pro Phe Gly Glu Val Phe Asn Ala Thr Lys Phe
1 5 10 15

Pro Ser Val Tyr Ala Trp Glu Arg Lys Lys Ile Ser Asn Cys Val Ala

```
            20                  25                  30

Asp Tyr Ser Val Leu Tyr Asn Ser Thr Phe Phe Ser Thr Phe Lys Cys
        35                  40                  45

Tyr Gly Val Ser Ala Thr Lys Leu Asn Asp Leu Cys Phe Ser Asn Val
    50                  55                  60

Tyr Ala Asp Ser Phe Val Val Lys Gly Asp Asp Val Arg Gln Ile Ala
65                  70                  75                  80

Pro Gly Gln Thr Gly Val Ile Ala Asp Tyr Asn Tyr Lys Leu Pro Asp
                85                  90                  95

Asp Phe Met Gly Cys Val Leu Ala Trp Asn Thr Arg Asn Ile Asp Ala
            100                 105                 110

Thr Ser Thr Gly Asn Tyr Asn Tyr Lys Tyr Arg Tyr Leu Arg His Gly
        115                 120                 125

Lys Leu Arg Pro Phe Glu Arg Asp Ile Ser Asn Val Pro Phe Ser Pro
    130                 135                 140

Asp Gly Lys Pro Cys Thr Pro Pro Ala Leu Asn Cys Tyr Trp Pro Leu
145                 150                 155                 160

Asn Asp Tyr Gly Phe Tyr Thr Thr Thr Gly Ile Gly Tyr Gln Pro Tyr
                165                 170                 175

Arg Val Val Val Leu Ser Phe Glu Leu Leu Asn Ala Pro Ala Thr
            180                 185                 190
```

<210> SEQ ID NO 27
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: MISC_FEATURE
<222> LOCATION: (1)..(1)
<223> OTHER INFORMATION: x is any amino acid repeated n times, wherein n is zero or an integer of from 1 to 5
<220> FEATURE:
<221> NAME/KEY: MISC_FEATURE
<222> LOCATION: (2)..(2)
<223> OTHER INFORMATION: x is equal to Gly, or Glu, or Leu or Thr
<220> FEATURE:
<221> NAME/KEY: MISC_FEATURE
<222> LOCATION: (3)..(3)
<223> OTHER INFORMATION: x is equal to Glu, or Asp
<220> FEATURE:
<221> NAME/KEY: MISC_FEATURE
<222> LOCATION: (4)..(4)
<223> OTHER INFORMATION: x is equal to Glu, or Asn, or Pro, or Met, or Val, or Asp
<220> FEATURE:
<221> NAME/KEY: MISC_FEATURE
<222> LOCATION: (5)..(5)
<223> OTHER INFORMATION: x is any amino acid repeated n times, wherein n is zero or an integer of from 1 to 5

<400> SEQUENCE: 27

```
Xaa Xaa Xaa Xaa Xaa
1               5
```

<210> SEQ ID NO 28
<211> LENGTH: 112
<212> TYPE: PRT
<213> ORGANISM: Artificial Sequence
<220> FEATURE:
<223> OTHER INFORMATION: SARS RBD 319-430

<400> SEQUENCE: 28

```
Ile Thr Asn Leu Cys Pro Phe Gly Glu Val Phe Asn Ala Thr Lys Phe
```

-continued 1 5 10 15

Pro Ser Val Tyr Ala Trp Glu Arg Lys Lys Ile Ser Asn Cys Val Ala
20 25 30

Asp Tyr Ser Val Leu Tyr Asn Ser Thr Phe Phe Ser Thr Phe Lys Cys
35 40 45

Tyr Gly Val Ser Ala Thr Lys Leu Asn Asp Leu Cys Phe Ser Asn Val
50 55 60

Tyr Ala Asp Ser Phe Val Val Lys Gly Asp Asp Val Arg Gln Ile Ala
65 70 75 80

Pro Gly Gln Thr Gly Val Ile Ala Asp Tyr Asn Tyr Lys Leu Pro Asp
85 90 95

Asp Phe Met Gly Cys Val Leu Ala Trp Asn Thr Arg Asn Ile Asp Ala
100 105 110

<210> SEQ ID NO 29
<211> LENGTH: 4
<212> TYPE: PRT
<213> ORGANISM: Artificial Sequence
<220> FEATURE:
<223> OTHER INFORMATION: linker
<220> FEATURE:
<221> NAME/KEY: MISC_FEATURE
<222> LOCATION: (1)..(1)
<223> OTHER INFORMATION: x is equal to Gly or Leu
<220> FEATURE:
<221> NAME/KEY: MISC_FEATURE
<222> LOCATION: (2)..(2)
<223> OTHER INFORMATION: x is equal to Glu or Asp
<220> FEATURE:
<221> NAME/KEY: MISC_FEATURE
<222> LOCATION: (3)..(3)
<223> OTHER INFORMATION: x is equal to Pro, or Val, or Gly
<220> FEATURE:
<221> NAME/KEY: MISC_FEATURE
<222> LOCATION: (4)..(4)
<223> OTHER INFORMATION: x is equal to Gly, or Met, or Asn, or Asp, or Leu

<400> SEQUENCE: 29

Xaa Xaa Xaa Xaa
1

<210> SEQ ID NO 30
<211> LENGTH: 30
<212> TYPE: PRT
<213> ORGANISM: Artificial Sequence
<220> FEATURE:
<223> OTHER INFORMATION: SARS mutated residues 460-486

<400> SEQUENCE: 30

Phe Ser Pro Asp Gly Ile Pro Cys Thr Pro Cys Thr Pro Pro Ala Leu
1 5 10 15

Asn Cys Tyr Trp Pro Leu Asn Asp Tyr Gly Phe Tyr Thr Thr
20 25 30

<210> SEQ ID NO 31
<211> LENGTH: 1255
<212> TYPE: PRT
<213> ORGANISM: Severe Acute Respiratory Syndrome coronavirus (SARS coronavirus)
<220> FEATURE:
<221> NAME/KEY: MISC_FEATURE
<223> OTHER INFORMATION: S1 protein, GenBank : AAR86788.,AA86788.1,AAR86788, accession AY463059.1

<400> SEQUENCE: 31

-continued

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
```

-continued

```
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ala Phe Gly Gly Val Ser Val Ile Thr Pro Gly Thr Asn Ala Ser Ser
            580                 585                 590

Glu Val Ala Val Leu Tyr Gln Asp Val Asn Cys Thr Asn Val Ser Ala
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845
```

-continued

```
Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
    1025                1030                1035

Pro His  Gly Val Val Phe Leu  His Val Thr Tyr Val  Pro Ser Gln
    1040                1045                1050

Glu Arg  Asn Phe Thr Thr Ala  Pro Ala Ile Cys His  Glu Gly Lys
    1055                1060                1065

Ala Tyr  Phe Pro Arg Glu Gly  Val Phe Val Phe Asn  Gly Thr Ser
    1070                1075                1080

Trp Phe  Ile Thr Gln Arg Asn  Phe Phe Ser Pro Gln  Ile Ile Thr
    1085                1090                1095

Thr Asp  Asn Thr Phe Val Ser  Gly Asn Cys Asp Val  Val Ile Gly
    1100                1105                1110

Ile Ile  Asn Asn Thr Val Tyr  Asp Pro Leu Gln Pro  Glu Leu Asp
    1115                1120                1125

Ser Phe  Lys Gly Glu Leu Asp  Lys Tyr Phe Lys Asn  His Thr Ser
    1130                1135                1140

Pro Asp  Val Asp Leu Gly Asp  Ile Ser Gly Ile Asn  Ala Ser Val
    1145                1150                1155

Val Asn  Ile Gln Lys Glu Ile  Asp Arg Leu Asn Glu  Val Ala Lys
    1160                1165                1170

Asn Leu  Asn Glu Ser Leu Ile  Asp Leu Gln Glu Leu  Gly Lys Tyr
    1175                1180                1185

Glu Gln  Tyr Ile Lys Trp Pro  Trp Tyr Val Trp Leu  Gly Phe Ile
    1190                1195                1200

Ala Gly  Leu Ile Ala Ile Val  Met Val Thr Ile Leu  Leu Cys Cys
    1205                1210                1215

Met Thr  Ser Cys Cys Ser Cys  Leu Lys Gly Ala Cys  Ser Cys Gly
    1220                1225                1230

Ser Cys  Cys Lys Phe Asp Glu  Asp Asp Ser Glu Pro  Val Leu Lys
    1235                1240                1245
```

```
Gly Val  Lys Leu His Tyr Thr
    1250                1255


<210> SEQ ID NO 32
<211> LENGTH: 203
<212> TYPE: PRT
<213> ORGANISM: Artificial Sequence
<220> FEATURE:
<223> OTHER INFORMATION: SARS RBD PDB: 2GHW_A GI:116667256 PUBMED
      16954221

<400> SEQUENCE: 32

Met Ala Asp Pro Asn Ile Thr Asn Leu Cys Pro Phe Gly Glu Val Phe
1               5                   10                  15

Asn Ala Thr Lys Phe Pro Ser Val Tyr Ala Trp Glu Arg Lys Lys Ile
            20                  25                  30

Ser Asn Cys Val Ala Asp Tyr Ser Val Leu Tyr Asn Ser Thr Phe Phe
        35                  40                  45

Ser Thr Phe Lys Cys Tyr Gly Val Ser Ala Thr Lys Leu Asn Asp Leu
    50                  55                  60

Cys Phe Ser Asn Val Tyr Ala Asp Ser Phe Val Val Lys Gly Asp Asp
65                  70                  75                  80

Val Arg Gln Ile Ala Pro Gly Gln Thr Gly Val Ile Ala Asp Tyr Asn
                85                  90                  95

Tyr Lys Leu Pro Asp Asp Phe Met Gly Cys Val Leu Ala Trp Asn Thr
            100                 105                 110

Arg Asn Ile Asp Ala Thr Ser Thr Gly Asn Tyr Asn Tyr Lys Tyr Arg
        115                 120                 125

Tyr Leu Arg His Gly Lys Leu Arg Pro Phe Glu Arg Asp Ile Ser Asn
    130                 135                 140

Val Pro Phe Ser Pro Asp Gly Lys Pro Cys Thr Pro Pro Ala Leu Asn
145                 150                 155                 160

Cys Tyr Trp Pro Leu Asn Asp Tyr Gly Phe Tyr Thr Thr Thr Gly Ile
                165                 170                 175

Gly Tyr Gln Pro Tyr Arg Val Val Val Leu Ser Phe Glu Leu Leu Asn
            180                 185                 190

Ala Pro Ala Thr Val Ser Gly Leu Val Pro Arg
        195                 200


<210> SEQ ID NO 33
<211> LENGTH: 194
<212> TYPE: PRT
<213> ORGANISM: Artificial Sequence
<220> FEATURE:
<223> OTHER INFORMATION: SARS coronavirus RBD residues 317-510

<400> SEQUENCE: 33

Pro Asn Ile Thr Asn Leu Cys Pro Phe Gly Glu Val Phe Asn Ala Thr
1               5                   10                  15

Lys Phe Pro Ser Val Tyr Ala Trp Glu Arg Lys Lys Ile Ser Asn Cys
            20                  25                  30

Val Ala Asp Tyr Ser Val Leu Tyr Asn Ser Thr Phe Phe Ser Thr Phe
        35                  40                  45

Lys Cys Tyr Gly Val Ser Ala Thr Lys Leu Asn Asp Leu Cys Phe Ser
    50                  55                  60

Asn Val Tyr Ala Asp Ser Phe Val Val Lys Gly Asp Asp Val Arg Gln
65                  70                  75                  80

Ile Ala Pro Gly Gln Thr Gly Val Ile Ala Asp Tyr Asn Tyr Lys Leu
```

```
                85                  90                  95

Pro Asp Asp Phe Met Gly Cys Val Leu Ala Trp Asn Thr Arg Asn Ile
            100                 105                 110

Asp Ala Thr Ser Thr Gly Asn Tyr Asn Tyr Lys Tyr Arg Tyr Leu Arg
        115                 120                 125

His Gly Lys Leu Arg Pro Phe Glu Arg Asp Ile Ser Asn Val Pro Phe
    130                 135                 140

Ser Pro Asp Gly Lys Pro Cys Thr Pro Pro Ala Leu Asn Cys Tyr Trp
145                 150                 155                 160

Pro Leu Asn Asp Tyr Gly Phe Tyr Thr Thr Thr Gly Ile Gly Tyr Gln
                165                 170                 175

Pro Tyr Arg Val Val Val Leu Ser Phe Glu Leu Leu Asn Ala Pro Ala
            180                 185                 190

Thr Val


<210> SEQ ID NO 34
<211> LENGTH: 1353
<212> TYPE: PRT
<213> ORGANISM: Middle East respiratory syndrome coronavirus [MERS]
<220> FEATURE:
<221> NAME/KEY: MISC_FEATURE
<223> OTHER INFORMATION: spike S1 protein GenBank : AHX00731.1
      G1:612348173

<400> SEQUENCE: 34

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240
```

-continued

```
Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Gly Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
```

-continued

```
            660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
    690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
        755                 760                 765

Gln Val Asp Gln Phe Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Ile Cys Asn Gly Phe Gln Lys
                805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
    850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990

Asn Gln Lys Leu Ile Ala Asn Lys  Phe Asn Gln Ala Leu  Gly Ala Met
        995                 1000                1005

Gln Thr  Gly Phe Thr Thr Thr  Asn Glu Ala Phe Arg  Lys Val Gln
    1010                1015                1020

Asp Ala  Val Asn Asn Asn Ala  Gln Ala Leu Ser Lys  Leu Ala Ser
    1025                1030                1035

Glu Leu  Ser Asn Thr Phe Gly  Ala Ile Ser Ala Ser  Ile Gly Asp
    1040                1045                1050

Ile Ile  Gln Arg Leu Asp Val  Leu Glu Gln Asp Ala  Gln Ile Asp
    1055                1060                1065

Arg Leu  Ile Asn Gly Arg Leu  Thr Thr Leu Asn Ala  Phe Val Ala
    1070                1075                1080
```

Gln Gln Leu Val Arg Ser Glu Ser Ala Ala Leu Ser Ala Gln Leu
1085 1090 1095

Ala Lys Asp Lys Val Asn Glu Cys Val Lys Ala Gln Ser Lys Arg
1100 1105 1110

Ser Gly Phe Cys Gly Gln Gly Thr His Ile Val Ser Phe Val Val
1115 1120 1125

Asn Ala Pro Asn Gly Leu Tyr Phe Met His Val Gly Tyr Tyr Pro
1130 1135 1140

Ser Asn His Ile Glu Val Val Ser Ala Tyr Gly Leu Cys Asp Ala
1145 1150 1155

Ala Asn Pro Thr Asn Cys Ile Ala Pro Val Asn Gly Tyr Phe Ile
1160 1165 1170

Lys Thr Asn Asn Thr Arg Ile Val Asp Glu Trp Ser Tyr Thr Gly
1175 1180 1185

Ser Ser Phe Tyr Ser Pro Glu Pro Ile Thr Ser Leu Asn Thr Lys
1190 1195 1200

Tyr Val Ala Pro Gln Val Thr Tyr Gln Asn Ile Ser Thr Asn Leu
1205 1210 1215

Pro Pro Pro Leu Leu Gly Asn Ser Thr Gly Ile Asp Phe Gln Asp
1220 1225 1230

Glu Leu Asp Glu Phe Phe Lys Asn Val Ser Thr Ser Ile Pro Asn
1235 1240 1245

Phe Gly Ser Leu Thr Gln Ile Asn Thr Thr Leu Leu Asp Leu Thr
1250 1255 1260

Tyr Glu Met Leu Ser Leu Gln Gln Val Val Lys Ala Leu Asn Glu
1265 1270 1275

Ser Tyr Ile Asp Leu Lys Glu Leu Gly Asn Tyr Thr Tyr Tyr Asn
1280 1285 1290

Lys Trp Pro Trp Tyr Ile Trp Leu Gly Phe Ile Ala Gly Leu Val
1295 1300 1305

Ala Leu Ala Leu Cys Val Phe Phe Ile Leu Cys Cys Thr Gly Cys
1310 1315 1320

Gly Thr Asn Cys Met Gly Lys Leu Lys Cys Asn Arg Cys Cys Asp
1325 1330 1335

Arg Tyr Glu Glu Tyr Asp Leu Glu Pro His Lys Val His Val His
1340 1345 1350

<210> SEQ ID NO 35
<211> LENGTH: 251
<212> TYPE: PRT
<213> ORGANISM: Artificial Sequence
<220> FEATURE:
<223> OTHER INFORMATION: Chain B, Structure Of The Receptor Binding Domain (RBD) Of Mers-cov SpikePDB: 4KQZ_B LOCUS 4KQZ_B 251 aa GI:523309906

<400> SEQUENCE: 35

Ala Asp Gly Ile Gln Glu Ala Lys Pro Ser Gly Ser Val Val Glu Gln
1 5 10 15

Ala Glu Gly Val Glu Cys Asp Phe Ser Pro Leu Leu Ser Gly Thr Pro
20 25 30

Pro Gln Val Tyr Asn Phe Lys Arg Leu Val Phe Thr Asn Cys Asn Tyr
35 40 45

Asn Leu Thr Lys Leu Leu Ser Leu Phe Ser Val Asn Asp Phe Thr Cys
50 55 60

-continued

Ser Gln Ile Ser Pro Ala Ala Ile Ala Ser Asn Cys Tyr Ser Ser Leu
65 70 75 80

Ile Leu Asp Tyr Phe Ser Tyr Pro Leu Ser Met Lys Ser Asp Leu Ser
85 90 95

Val Ser Ser Ala Gly Pro Ile Ser Gln Phe Asn Tyr Lys Gln Ser Phe
100 105 110

Ser Asn Pro Thr Cys Leu Ile Leu Ala Thr Val Pro His Asn Leu Thr
115 120 125

Thr Ile Thr Lys Pro Leu Lys Tyr Ser Tyr Ile Asn Lys Cys Ser Arg
130 135 140

Leu Leu Ser Asp Asp Arg Thr Glu Val Pro Gln Leu Val Asn Ala Asn
145 150 155 160

Gln Tyr Ser Pro Cys Val Ser Ile Val Pro Ser Thr Val Trp Glu Asp
165 170 175

Gly Asp Tyr Tyr Arg Lys Gln Leu Ser Pro Leu Glu Gly Gly Gly Trp
180 185 190

Leu Val Ala Ser Gly Ser Thr Val Ala Met Thr Glu Gln Leu Gln Met
195 200 205

Gly Phe Gly Ile Thr Val Gln Tyr Gly Thr Asp Thr Asn Ser Val Cys
210 215 220

Pro Lys Leu Glu Phe Ala Asn Asp Thr Lys Ile Ala Ser Gln Leu Gly
225 230 235 240

Asn Cys Val Glu Tyr His His His His His His
245 250

<210> SEQ ID NO 36
<211> LENGTH: 240
<212> TYPE: PRT
<213> ORGANISM: Artificial Sequence
<220> FEATURE:
<223> OTHER INFORMATION: MERS coronavirus RBD

<400> SEQUENCE: 36

Glu Ala Lys Pro Ser Gly Ser Val Val Glu Gln Ala Glu Gly Val Glu
1 5 10 15

Cys Asp Phe Ser Pro Leu Leu Ser Gly Thr Pro Pro Gln Val Tyr Asn
20 25 30

Phe Lys Arg Leu Val Phe Thr Asn Cys Asn Tyr Asn Leu Thr Lys Leu
35 40 45

Leu Ser Leu Phe Ser Val Asn Asp Phe Thr Cys Ser Gln Ile Ser Pro
50 55 60

Ala Ala Ile Ala Ser Asn Cys Tyr Ser Ser Leu Ile Leu Asp Tyr Phe
65 70 75 80

Ser Tyr Pro Leu Ser Met Lys Ser Asp Leu Gly Val Ser Ser Ala Gly
85 90 95

Pro Ile Ser Gln Phe Asn Tyr Lys Gln Ser Phe Ser Asn Pro Thr Cys
100 105 110

Leu Ile Leu Ala Thr Val Pro His Asn Leu Thr Thr Ile Thr Lys Pro
115 120 125

Leu Lys Tyr Ser Tyr Ile Asn Lys Cys Ser Arg Leu Leu Ser Asp Asp
130 135 140

Arg Thr Glu Val Pro Gln Leu Val Asn Ala Asn Gln Tyr Ser Pro Cys
145 150 155 160

Val Ser Ile Val Pro Ser Thr Val Trp Glu Asp Gly Asp Tyr Tyr Arg
165 170 175

-continued

```
Lys Gln Leu Ser Pro Leu Glu Gly Gly Gly Trp Leu Val Ala Ser Gly
            180                 185                 190

Ser Thr Val Ala Met Thr Glu Gln Leu Gln Met Gly Phe Gly Ile Thr
        195                 200                 205

Val Gln Tyr Gly Thr Asp Thr Asn Ser Val Cys Pro Lys Leu Glu Phe
    210                 215                 220

Ala Asn Asp Thr Lys Ile Ala Ser Gln Leu Gly Asn Cys Val Glu Tyr
225                 230                 235                 240


<210> SEQ ID NO 37
<211> LENGTH: 12
<212> TYPE: PRT
<213> ORGANISM: Artificial Sequence
<220> FEATURE:
<223> OTHER INFORMATION: MERS residues 535-546

<400> SEQUENCE: 37

Trp Glu Asp Gly Asp Tyr Tyr Arg Lys Gln Leu Ser
1               5                   10


<210> SEQ ID NO 38
<211> LENGTH: 10
<212> TYPE: PRT
<213> ORGANISM: Artificial Sequence
<220> FEATURE:
<223> OTHER INFORMATION: MERS residues 551-560

<400> SEQUENCE: 38

Gly Gly Trp Leu Val Ala Ser Gly Ser Thr
1               5                   10


<210> SEQ ID NO 39
<211> LENGTH: 4
<212> TYPE: PRT
<213> ORGANISM: Artificial Sequence
<220> FEATURE:
<223> OTHER INFORMATION: linker

<400> SEQUENCE: 39

Gly Glu Pro Gly
1


<210> SEQ ID NO 40
<211> LENGTH: 4
<212> TYPE: PRT
<213> ORGANISM: Artificial Sequence
<220> FEATURE:
<223> OTHER INFORMATION: linker

<400> SEQUENCE: 40

Gly Asp Pro Gly
1


<210> SEQ ID NO 41
<211> LENGTH: 4
<212> TYPE: PRT
<213> ORGANISM: Artificial Sequence
<220> FEATURE:
<223> OTHER INFORMATION: linker

<400> SEQUENCE: 41

Gly Glu Pro Met
1


<210> SEQ ID NO 42
```

<211> LENGTH: 72
<212> TYPE: PRT
<213> ORGANISM: Artificial Sequence
<220> FEATURE:
<223> OTHER INFORMATION: MERS Residues 493-564

<400> SEQUENCE: 42

Lys Pro Leu Lys Tyr Ser Tyr Ile Asn Lys Cys Ser Arg Leu Leu Ser
1               5                   10                  15

Asp Asp Arg Thr Glu Val Pro Gln Leu Val Asn Ala Asn Gln Tyr Ser
            20                  25                  30

Pro Cys Val Ser Ile Val Pro Ser Thr Val Trp Glu Asp Gly Asp Tyr
        35                  40                  45

Tyr Arg Lys Gln Leu Ser Pro Leu Glu Gly Gly Gly Trp Leu Val Ala
    50                  55                  60

Ser Gly Ser Thr Val Ala Met Thr
65                  70

<210> SEQ ID NO 43
<211> LENGTH: 14
<212> TYPE: PRT
<213> ORGANISM: Artificial Sequence
<220> FEATURE:
<223> OTHER INFORMATION: MERS Residues 514-527

<400> SEQUENCE: 43

Val Pro Gln Leu Val Asn Ala Asn Gln Tyr Ser Pro Cys Val
1               5                   10

<210> SEQ ID NO 44
<211> LENGTH: 22
<212> TYPE: PRT
<213> ORGANISM: Artificial Sequence
<220> FEATURE:
<223> OTHER INFORMATION: MERS Residues 493-514

<400> SEQUENCE: 44

Lys Pro Leu Lys Tyr Ser Tyr Ile Asn Lys Cys Ser Arg Leu Leu Ser
1               5                   10                  15

Asp Asp Arg Thr Glu Val
            20

<210> SEQ ID NO 45
<211> LENGTH: 38
<212> TYPE: PRT
<213> ORGANISM: Artificial Sequence
<220> FEATURE:
<223> OTHER INFORMATION: MERS Residues 527-564

<400> SEQUENCE: 45

Val Ser Ile Val Pro Ser Thr Val Trp Glu Asp Gly Asp Tyr Tyr Arg
1               5                   10                  15

Lys Gln Leu Ser Pro Leu Glu Gly Gly Gly Trp Leu Val Ala Ser Gly
            20                  25                  30

Ser Thr Val Ala Met Thr
        35

<210> SEQ ID NO 46
<211> LENGTH: 8
<212> TYPE: PRT
<213> ORGANISM: Artificial Sequence
<220> FEATURE:
<223> OTHER INFORMATION: MERS Residues 538-545

<400> SEQUENCE: 46

Gly Asp Tyr Tyr Arg Lys Gln Leu
1               5

<210> SEQ ID NO 47
<211> LENGTH: 8
<212> TYPE: PRT
<213> ORGANISM: Artificial Sequence
<220> FEATURE:
<223> OTHER INFORMATION: MERS Residues 552-559

<400> SEQUENCE: 47

Gly Trp Leu Val Ala Ser Gly Ser
1               5

<210> SEQ ID NO 48
<211> LENGTH: 32
<212> TYPE: PRT
<213> ORGANISM: Artificial Sequence
<220> FEATURE:
<223> OTHER INFORMATION: MERS reconstituted RBM

<400> SEQUENCE: 48

Cys Phe Trp Glu Asp Gly Asp Tyr Tyr Arg Lys Gln Leu Ser Gly Phe
1               5                   10                  15

Asp Glu Gln Gly Gly Trp Leu Val Ala Ser Gly Ser Thr Gln Leu Thr
            20                  25                  30

<210> SEQ ID NO 49
<211> LENGTH: 5
<212> TYPE: PRT
<213> ORGANISM: Artificial Sequence
<220> FEATURE:
<223> OTHER INFORMATION: linker

<400> SEQUENCE: 49

Gly Phe Asp Glu Gln
1               5

<210> SEQ ID NO 50
<211> LENGTH: 27
<212> TYPE: PRT
<213> ORGANISM: Artificial Sequence
<220> FEATURE:
<223> OTHER INFORMATION: MERS reconstituted RBM

<400> SEQUENCE: 50

Trp Glu Asp Gly Asp Tyr Tyr Arg Lys Gln Leu Ser Pro Tyr Asn Tyr
1               5                   10                  15

His Gly Gly Trp Leu Val Ala Ser Gly Ser Thr
            20                  25

<210> SEQ ID NO 51
<211> LENGTH: 5
<212> TYPE: PRT
<213> ORGANISM: Artificial Sequence
<220> FEATURE:
<223> OTHER INFORMATION: linker

<400> SEQUENCE: 51

Pro Tyr Asn Tyr His
1               5

<210> SEQ ID NO 52
<211> LENGTH: 27

-continued

<212> TYPE: PRT
<213> ORGANISM: Artificial Sequence
<220> FEATURE:
<223> OTHER INFORMATION: MERS reconstituted RBM

<400> SEQUENCE: 52

Trp Glu Asp Gly Asp Tyr Tyr Arg Lys Gln Leu Ser Ser Gln Ala Pro
1 5 10 15

Leu Gly Gly Trp Leu Val Ala Ser Gly Ser Thr
20 25

<210> SEQ ID NO 53
<211> LENGTH: 5
<212> TYPE: PRT
<213> ORGANISM: Artificial Sequence
<220> FEATURE:
<223> OTHER INFORMATION: linker

<400> SEQUENCE: 53

Ser Gln Ala Pro Leu
1 5

<210> SEQ ID NO 54
<211> LENGTH: 31
<212> TYPE: PRT
<213> ORGANISM: Artificial Sequence
<220> FEATURE:
<223> OTHER INFORMATION: MERS reconstituted RBM

<400> SEQUENCE: 54

Leu Gly Trp Glu Asp Gly Asp Tyr Tyr Arg Lys Gln Leu Ser Leu His
1 5 10 15

Leu Pro Gly Gly Trp Leu Val Ala Ser Gly Ser Thr Ile Arg Lys
20 25 30

<210> SEQ ID NO 55
<211> LENGTH: 4
<212> TYPE: PRT
<213> ORGANISM: Artificial Sequence
<220> FEATURE:
<223> OTHER INFORMATION: linker

<400> SEQUENCE: 55

Leu His Leu Pro
1

<210> SEQ ID NO 56
<211> LENGTH: 26
<212> TYPE: PRT
<213> ORGANISM: Artificial Sequence
<220> FEATURE:
<223> OTHER INFORMATION: MERS reconstituted RBM

<400> SEQUENCE: 56

Trp Glu Asp Gly Asp Tyr Tyr Arg Lys Gln Leu Ser Val Val Ala Thr
1 5 10 15

Gly Gly Trp Leu Val Ala Ser Gly Ser Thr
20 25

<210> SEQ ID NO 57
<211> LENGTH: 4
<212> TYPE: PRT
<213> ORGANISM: Artificial Sequence
<220> FEATURE:
<223> OTHER INFORMATION: linker

<400> SEQUENCE: 57

Val Val Ala Thr
1

<210> SEQ ID NO 58
<211> LENGTH: 30
<212> TYPE: PRT
<213> ORGANISM: Artificial Sequence
<220> FEATURE:
<223> OTHER INFORMATION: MERS reconstituted RBM

<400> SEQUENCE: 58

```
Phe Gln Ser Trp Glu Asp Gly Asp Tyr Tyr Arg Lys Gln Leu Ser Val
1               5                   10                  15

Tyr Ser Gly Gly Trp Leu Val Ala Ser Gly Ser Thr Leu Gln
            20                  25                  30
```

<210> SEQ ID NO 59
<211> LENGTH: 24
<212> TYPE: PRT
<213> ORGANISM: Artificial Sequence
<220> FEATURE:
<223> OTHER INFORMATION: MERS reconstituted RBM

<400> SEQUENCE: 59

```
Trp Glu Asp Gly Asp Tyr Tyr Arg Lys Gln Leu Ser Arg Gln Gly Gly
1               5                   10                  15

Trp Leu Val Ala Ser Gly Ser Thr
            20
```

<210> SEQ ID NO 60
<211> LENGTH: 26
<212> TYPE: PRT
<213> ORGANISM: Artificial Sequence
<220> FEATURE:
<223> OTHER INFORMATION: MERS reconstituted RBM

<400> SEQUENCE: 60

```
Trp Glu Asp Gly Asp Tyr Tyr Arg Lys Gln Leu Ser Ser Tyr Gly Gly
1               5                   10                  15

Trp Leu Val Ala Ser Gly Ser Thr Pro Thr
            20                  25
```

<210> SEQ ID NO 61
<211> LENGTH: 27
<212> TYPE: PRT
<213> ORGANISM: Artificial Sequence
<220> FEATURE:
<223> OTHER INFORMATION: MERS reconstituted RBM

<400> SEQUENCE: 61

```
Trp Glu Asp Gly Asp Tyr Tyr Arg Lys Gln Leu Ser Phe Ser Gly Gly
1               5                   10                  15

Trp Leu Val Ala Ser Gly Ser Thr Arg Thr Lys
            20                  25
```

<210> SEQ ID NO 62
<211> LENGTH: 29
<212> TYPE: PRT
<213> ORGANISM: Artificial Sequence
<220> FEATURE:
<223> OTHER INFORMATION: MERS reconstituted RBM

<400> SEQUENCE: 62

```
Ser Ile Arg Trp Glu Asp Gly Asp Tyr Tyr Arg Lys Gln Leu Ser Cys
1               5                   10                  15

Gly Gly Trp Leu Val Ala Ser Gly Ser Thr Arg Leu Thr
            20                  25


<210> SEQ ID NO 63
<211> LENGTH: 25
<212> TYPE: PRT
<213> ORGANISM: Artificial Sequence
<220> FEATURE:
<223> OTHER INFORMATION: MERS reconstituted RBM

<400> SEQUENCE: 63

Trp Glu Asp Gly Asp Tyr Tyr Arg Lys Gln Leu Ser Cys Gly Gly Trp
1               5                   10                  15

Leu Val Ala Ser Gly Ser Thr Leu Pro
            20                  25


<210> SEQ ID NO 64
<211> LENGTH: 24
<212> TYPE: PRT
<213> ORGANISM: Artificial Sequence
<220> FEATURE:
<223> OTHER INFORMATION: MERS reconstituted RBM

<400> SEQUENCE: 64

Ala Trp Glu Asp Gly Asp Tyr Tyr Arg Lys Gln Leu Ser Tyr Gly Gly
1               5                   10                  15

Trp Leu Val Ala Ser Gly Ser Thr
            20


<210> SEQ ID NO 65
<211> LENGTH: 37
<212> TYPE: PRT
<213> ORGANISM: Artificial Sequence
<220> FEATURE:
<223> OTHER INFORMATION: MERS CoV 530-566

<400> SEQUENCE: 65

Val Pro Ser Thr Val Trp Glu Asp Gly Asp Tyr Tyr Arg Lys Gln Leu
1               5                   10                  15

Ser Pro Leu Glu Gly Gly Gly Trp Leu Val Ala Ser Gly Ser Thr Val
            20                  25                  30

Ala Met Thr Glu Gln
        35


<210> SEQ ID NO 66
<211> LENGTH: 24
<212> TYPE: PRT
<213> ORGANISM: Artificial Sequence
<220> FEATURE:
<223> OTHER INFORMATION: MERS CoV residues 491-514

<400> SEQUENCE: 66

Ile Thr Lys Pro Leu Lys Tyr Ser Tyr Ile Asn Lys Cys Ser Arg Leu
1               5                   10                  15

Leu Ser Asp Asp Arg Thr Glu Val
            20


<210> SEQ ID NO 67
<211> LENGTH: 38
<212> TYPE: PRT
<213> ORGANISM: Artificial Sequence
<220> FEATURE:
```

-continued

<223> OTHER INFORMATION: MERS CoV residues 530-567

<400> SEQUENCE: 67

Val Pro Ser Thr Val Trp Glu Asp Gly Asp Tyr Tyr Arg Lys Gln Leu
1 5 10 15

Ser Pro Leu Glu Gly Gly Gly Trp Leu Val Ala Ser Gly Ser Thr Val
20 25 30

Ala Met Thr Glu Gln Leu
35

<210> SEQ ID NO 68
<211> LENGTH: 23
<212> TYPE: PRT
<213> ORGANISM: Artificial Sequence
<220> FEATURE:
<223> OTHER INFORMATION: MERS CoV S1 residues 491-513

<400> SEQUENCE: 68

Ile Thr Lys Pro Leu Lys Tyr Ser Tyr Ile Asn Lys Cys Ser Arg Leu
1 5 10 15

Leu Ser Asp Asp Arg Thr Glu
20

<210> SEQ ID NO 69
<211> LENGTH: 40
<212> TYPE: PRT
<213> ORGANISM: Artificial Sequence
<220> FEATURE:
<223> OTHER INFORMATION: MERS CoV S1 residues 528-567

<400> SEQUENCE: 69

Ser Ile Val Pro Ser Thr Val Trp Glu Asp Gly Asp Tyr Tyr Arg Lys
1 5 10 15

Gln Leu Ser Pro Leu Glu Gly Gly Gly Trp Leu Val Ala Ser Gly Ser
20 25 30

Thr Val Ala Met Thr Glu Gln Leu
35 40

<210> SEQ ID NO 70
<211> LENGTH: 21
<212> TYPE: PRT
<213> ORGANISM: Artificial Sequence
<220> FEATURE:
<223> OTHER INFORMATION: MERS CoV S1 residues 493-513

<400> SEQUENCE: 70

Lys Pro Leu Lys Tyr Ser Tyr Ile Asn Lys Cys Ser Arg Leu Leu Ser
1 5 10 15

Asp Asp Arg Thr Glu
20

<210> SEQ ID NO 71
<211> LENGTH: 37
<212> TYPE: PRT
<213> ORGANISM: Artificial Sequence
<220> FEATURE:
<223> OTHER INFORMATION: MERS CoV S1 residues 528-564

<400> SEQUENCE: 71

Ser Ile Val Pro Ser Thr Val Trp Glu Asp Gly Asp Tyr Tyr Arg Lys
1 5 10 15

Gln Leu Ser Pro Leu Glu Gly Gly Gly Trp Leu Val Ala Ser Gly Ser
20 25 30

```
Thr Val Ala Met Thr
        35


<210> SEQ ID NO 72
<211> LENGTH: 8
<212> TYPE: PRT
<213> ORGANISM: Artificial Sequence
<220> FEATURE:
<223> OTHER INFORMATION: MERS CoV S1 residues 545-552

<400> SEQUENCE: 72

Leu Ser Pro Leu Glu Gly Gly Gly
1               5


<210> SEQ ID NO 73
<211> LENGTH: 6
<212> TYPE: PRT
<213> ORGANISM: Artificial Sequence
<220> FEATURE:
<223> OTHER INFORMATION: MERS CoV S1 residues 546-551

<400> SEQUENCE: 73

Ser Pro Leu Glu Gly Gly
1               5


<210> SEQ ID NO 74
<211> LENGTH: 7
<212> TYPE: PRT
<213> ORGANISM: Artificial Sequence
<220> FEATURE:
<223> OTHER INFORMATION: MERS-Cov S1 residues 538-544

<400> SEQUENCE: 74

Gly Asp Tyr Tyr Arg Lys Gln
1               5


<210> SEQ ID NO 75
<211> LENGTH: 7
<212> TYPE: PRT
<213> ORGANISM: Artificial Sequence
<220> FEATURE:
<223> OTHER INFORMATION: MERS-Cov S1 residues 553-559

<400> SEQUENCE: 75

Trp Leu Val Ala Ser Gly Ser
1               5


<210> SEQ ID NO 76
<211> LENGTH: 75
<212> TYPE: PRT
<213> ORGANISM: Artificial Sequence
<220> FEATURE:
<223> OTHER INFORMATION: MERS-Cov S1 residues 492-566

<400> SEQUENCE: 76

Thr Lys Pro Leu Lys Tyr Ser Tyr Ile Asn Lys Cys Ser Arg Leu Leu
1               5                   10                  15

Ser Asp Asp Arg Thr Glu Val Pro Gln Leu Val Asn Ala Asn Gln Tyr
            20                  25                  30

Ser Pro Cys Val Ser Ile Val Pro Ser Thr Val Trp Glu Asp Gly Asp
        35                  40                  45

Tyr Tyr Arg Lys Gln Leu Ser Pro Leu Glu Gly Gly Gly Trp Leu Val
    50                  55                  60

Ala Ser Gly Ser Thr Val Ala Met Thr Glu Gln
```

65 70 75

<210> SEQ ID NO 77
<211> LENGTH: 26
<212> TYPE: PRT
<213> ORGANISM: Artificial Sequence
<220> FEATURE:
<223> OTHER INFORMATION: MERS S1 residues 535-560

<400> SEQUENCE: 77

Trp Glu Asp Gly Asp Tyr Tyr Arg Lys Gln Leu Ser Pro Leu Glu Gly
1 5 10 15

Gly Gly Trp Leu Val Ala Ser Gly Ser Thr
20 25

<210> SEQ ID NO 78
<211> LENGTH: 7
<212> TYPE: PRT
<213> ORGANISM: Artificial Sequence
<220> FEATURE:
<223> OTHER INFORMATION: MERS S1 residues 498-564

<400> SEQUENCE: 78

Ser Tyr Ile Asn Lys Cys Ser
1 5

<210> SEQ ID NO 79
<211> LENGTH: 5
<212> TYPE: PRT
<213> ORGANISM: Artificial Sequence
<220> FEATURE:
<223> OTHER INFORMATION: MERS S1 residues 498-562

<400> SEQUENCE: 79

Ser Tyr Ile Asn Lys
1 5

<210> SEQ ID NO 80
<211> LENGTH: 14
<212> TYPE: PRT
<213> ORGANISM: Artificial Sequence
<220> FEATURE:
<223> OTHER INFORMATION: MERS S1 residues 492-565

<400> SEQUENCE: 80

Thr Lys Pro Leu Lys Tyr Ser Tyr Ile Asn Lys Cys Ser Arg
1 5 10

<210> SEQ ID NO 81
<211> LENGTH: 208
<212> TYPE: PRT
<213> ORGANISM: Artificial Sequence
<220> FEATURE:
<223> OTHER INFORMATION: MERS RBD 381-588

<400> SEQUENCE: 81

Val Glu Cys Asp Phe Ser Pro Leu Leu Ser Gly Thr Pro Pro Gln Val
1 5 10 15

Tyr Asn Phe Lys Arg Leu Val Phe Thr Asn Cys Asn Tyr Asn Leu Thr
20 25 30

Lys Leu Leu Ser Leu Phe Ser Val Asn Asp Phe Thr Cys Ser Gln Ile
35 40 45

Ser Pro Ala Ala Ile Ala Ser Asn Cys Tyr Ser Ser Leu Ile Leu Asp
50 55 60

-continued

```
Tyr Phe Ser Tyr Pro Leu Ser Met Lys Ser Asp Leu Gly Val Ser Ser
65                  70                  75                  80

Ala Gly Pro Ile Ser Gln Phe Asn Tyr Lys Gln Ser Phe Ser Asn Pro
                85                  90                  95

Thr Cys Leu Ile Leu Ala Thr Val Pro His Asn Leu Thr Thr Ile Thr
            100                 105                 110

Lys Pro Leu Lys Tyr Ser Tyr Ile Asn Lys Cys Ser Arg Leu Leu Ser
        115                 120                 125

Asp Asp Arg Thr Glu Val Pro Gln Leu Val Asn Ala Asn Gln Tyr Ser
    130                 135                 140

Pro Cys Val Ser Ile Val Pro Ser Thr Val Trp Glu Asp Gly Asp Tyr
145                 150                 155                 160

Tyr Arg Lys Gln Leu Ser Pro Leu Glu Gly Gly Gly Trp Leu Val Ala
                165                 170                 175

Ser Gly Ser Thr Val Ala Met Thr Glu Gln Leu Gln Met Gly Phe Gly
            180                 185                 190

Ile Thr Val Gln Tyr Gly Thr Asp Thr Asn Ser Val Cys Pro Lys Leu
        195                 200                 205


<210> SEQ ID NO 82
<211> LENGTH: 240
<212> TYPE: PRT
<213> ORGANISM: Artificial Sequence
<220> FEATURE:
<223> OTHER INFORMATION: MERS RBD 367-606

<400> SEQUENCE: 82

Glu Ala Lys Pro Ser Gly Ser Val Val Glu Gln Ala Glu Gly Val Glu
1               5                   10                  15

Cys Asp Phe Ser Pro Leu Leu Ser Gly Thr Pro Pro Gln Val Tyr Asn
            20                  25                  30

Phe Lys Arg Leu Val Phe Thr Asn Cys Asn Tyr Asn Leu Thr Lys Leu
        35                  40                  45

Leu Ser Leu Phe Ser Val Asn Asp Phe Thr Cys Ser Gln Ile Ser Pro
    50                  55                  60

Ala Ala Ile Ala Ser Asn Cys Tyr Ser Ser Leu Ile Leu Asp Tyr Phe
65                  70                  75                  80

Ser Tyr Pro Leu Ser Met Lys Ser Asp Leu Gly Val Ser Ser Ala Gly
                85                  90                  95

Pro Ile Ser Gln Phe Asn Tyr Lys Gln Ser Phe Ser Asn Pro Thr Cys
            100                 105                 110

Leu Ile Leu Ala Thr Val Pro His Asn Leu Thr Thr Ile Thr Lys Pro
        115                 120                 125

Leu Lys Tyr Ser Tyr Ile Asn Lys Cys Ser Arg Leu Leu Ser Asp Asp
    130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
            180                 185                 190

Ser Thr Val Ala Met Thr Glu Gln Leu Gln Met Gly Phe Gly Ile Thr
        195                 200                 205

Val Gln Tyr Gly Thr Asp Thr Asn Ser Val Cys Pro Lys Leu Glu Phe
    210                 215                 220
```

```
Ala Asn Asp Thr Lys Ile Ala Ser Gln Leu Gly Asn Cys Val Glu Tyr
225                 230                 235                 240


<210> SEQ ID NO 83
<211> LENGTH: 22
<212> TYPE: PRT
<213> ORGANISM: Artificial Sequence
<220> FEATURE:
<223> OTHER INFORMATION: MERS S1 538-559

<400> SEQUENCE: 83

Gly Asp Tyr Tyr Arg Lys Gln Leu Ser Pro Leu Glu Gly Gly Gly Trp
1               5                   10                  15

Leu Val Ala Ser Gly Ser
            20


<210> SEQ ID NO 84
<211> LENGTH: 24
<212> TYPE: PRT
<213> ORGANISM: Artificial Sequence
<220> FEATURE:
<223> OTHER INFORMATION: SARS S1 393-416

<400> SEQUENCE: 84

Asp Val Arg Gln Ile Ala Pro Gly Gln Thr Gly Val Ile Ala Asp Tyr
1               5                   10                  15

Asn Tyr Lys Leu Pro Asp Asp Phe
            20


<210> SEQ ID NO 85
<211> LENGTH: 180
<212> TYPE: PRT
<213> ORGANISM: Artificial Sequence
<220> FEATURE:
<223> OTHER INFORMATION: SARS RBD S1 323-502

<400> SEQUENCE: 85

Cys Pro Phe Gly Glu Val Phe Asn Ala Thr Lys Phe Pro Ser Val Tyr
1               5                   10                  15

Ala Trp Glu Arg Lys Lys Ile Ser Asn Cys Val Ala Asp Tyr Ser Val
            20                  25                  30

Leu Tyr Asn Ser Thr Phe Phe Ser Thr Phe Lys Cys Tyr Gly Val Ser
        35                  40                  45

Ala Thr Lys Leu Asn Asp Leu Cys Phe Ser Asn Val Tyr Ala Asp Ser
    50                  55                  60

Phe Val Val Lys Gly Asp Asp Val Arg Gln Ile Ala Pro Gly Gln Thr
65                  70                  75                  80

Gly Val Ile Ala Asp Tyr Asn Tyr Lys Leu Pro Asp Asp Phe Met Gly
                85                  90                  95

Cys Val Leu Ala Trp Asn Thr Arg Asn Ile Asp Ala Thr Ser Thr Gly
            100                 105                 110

Asn Tyr Asn Tyr Lys Tyr Arg Tyr Leu Arg His Gly Lys Leu Arg Pro
        115                 120                 125

Phe Glu Arg Asp Ile Ser Asn Val Pro Phe Ser Pro Asp Gly Lys Pro
    130                 135                 140

Cys Thr Pro Pro Ala Leu Asn Cys Tyr Trp Pro Leu Asn Asp Tyr Gly
145                 150                 155                 160

Phe Tyr Thr Thr Thr Gly Ile Gly Tyr Gln Pro Tyr Arg Val Val Val
                165                 170                 175

Leu Ser Phe Glu
```

180

<210> SEQ ID NO 86
<211> LENGTH: 13
<212> TYPE: PRT
<213> ORGANISM: Artificial Sequence
<220> FEATURE:
<223> OTHER INFORMATION: MERS S1 515-527

<400> SEQUENCE: 86

Pro Gln Leu Val Asn Ala Asn Gln Tyr Ser Pro Cys Val
1 5 10

<210> SEQ ID NO 87
<211> LENGTH: 192
<212> TYPE: PRT
<213> ORGANISM: Artificial Sequence
<220> FEATURE:
<223> OTHER INFORMATION: SARS S1 N318-T509

<400> SEQUENCE: 87

Asn Ile Thr Asn Leu Cys Pro Phe Gly Glu Val Phe Asn Ala Thr Lys
1 5 10 15

Phe Pro Ser Val Tyr Ala Trp Glu Arg Lys Lys Ile Ser Asn Cys Val
20 25 30

Ala Asp Tyr Ser Val Leu Tyr Asn Ser Thr Phe Phe Ser Thr Phe Lys
35 40 45

Cys Tyr Gly Val Ser Ala Thr Lys Leu Asn Asp Leu Cys Phe Ser Asn
50 55 60

Val Tyr Ala Asp Ser Phe Val Val Lys Gly Asp Asp Val Arg Gln Ile
65 70 75 80

Ala Pro Gly Gln Thr Gly Val Ile Ala Asp Tyr Asn Tyr Lys Leu Pro
85 90 95

Asp Asp Phe Met Gly Cys Val Leu Ala Trp Asn Thr Arg Asn Ile Asp
100 105 110

Ala Thr Ser Thr Gly Asn Tyr Asn Tyr Lys Tyr Arg Tyr Leu Arg His
115 120 125

Gly Lys Leu Arg Pro Phe Glu Arg Asp Ile Ser Asn Val Pro Phe Ser
130 135 140

Pro Asp Gly Lys Pro Cys Thr Pro Pro Ala Leu Asn Cys Tyr Trp Pro
145 150 155 160

Leu Asn Asp Tyr Gly Phe Tyr Thr Thr Thr Gly Ile Gly Tyr Gln Pro
165 170 175

Tyr Arg Val Val Val Leu Ser Phe Glu Leu Leu Asn Ala Pro Ala Thr
180 185 190

<210> SEQ ID NO 88
<211> LENGTH: 18
<212> TYPE: PRT
<213> ORGANISM: Artificial Sequence
<220> FEATURE:
<223> OTHER INFORMATION: SARS S1 443-460

<400> SEQUENCE: 88

Leu Arg His Gly Lys Leu Arg Pro Phe Glu Arg Asp Ile Ser Asn Val
1 5 10 15

Pro Phe

<210> SEQ ID NO 89
<211> LENGTH: 44

<212> TYPE: PRT
<213> ORGANISM: Artificial Sequence
<220> FEATURE:
<223> OTHER INFORMATION: SARS reconstituted RBM

<400> SEQUENCE: 89

```
Ser Thr Gly Asn Tyr Asn Tyr Lys Tyr Arg Leu Gly Glu Met Phe Ser
1               5                   10                  15

Pro Asp Gly Lys Pro Cys Thr Pro Cys Thr Pro Pro Ala Leu Asn Cys
            20                  25                  30

Tyr Trp Pro Leu Asn Asp Tyr Gly Phe Tyr Thr Thr
        35                  40
```

<210> SEQ ID NO 90
<211> LENGTH: 44
<212> TYPE: PRT
<213> ORGANISM: Artificial Sequence
<220> FEATURE:
<223> OTHER INFORMATION: SARS reconstituted RBM

<400> SEQUENCE: 90

```
Ser Thr Gly Asn Tyr Asn Tyr Lys Tyr Arg Leu Glu Glu Pro Phe Ser
1               5                   10                  15

Pro Asp Gly Lys Pro Cys Thr Pro Cys Thr Pro Pro Ala Leu Asn Cys
            20                  25                  30

Tyr Trp Pro Leu Asn Asp Tyr Gly Phe Tyr Thr Thr
        35                  40
```

<210> SEQ ID NO 91
<211> LENGTH: 44
<212> TYPE: PRT
<213> ORGANISM: Artificial Sequence
<220> FEATURE:
<223> OTHER INFORMATION: SARS reconstituted RBM

<400> SEQUENCE: 91

```
Ser Thr Gly Asn Tyr Asn Tyr Lys Tyr Arg Leu Gly Glu Glu Phe Ser
1               5                   10                  15

Pro Asp Gly Lys Pro Cys Thr Pro Cys Thr Pro Pro Ala Leu Asn Cys
            20                  25                  30

Tyr Trp Pro Leu Asn Asp Tyr Gly Phe Tyr Thr Thr
        35                  40
```

<210> SEQ ID NO 92
<211> LENGTH: 44
<212> TYPE: PRT
<213> ORGANISM: Artificial Sequence
<220> FEATURE:
<223> OTHER INFORMATION: SARS reconstituted RBM

<400> SEQUENCE: 92

```
Ser Thr Gly Asn Tyr Asn Tyr Lys Tyr Arg Leu Gly Glu Asn Phe Ser
1               5                   10                  15

Pro Asp Gly Lys Pro Cys Thr Pro Cys Thr Pro Pro Ala Leu Asn Cys
            20                  25                  30

Tyr Trp Pro Leu Asn Asp Tyr Gly Phe Tyr Thr Thr
        35                  40
```

<210> SEQ ID NO 93
<211> LENGTH: 45
<212> TYPE: PRT
<213> ORGANISM: Artificial Sequence
<220> FEATURE:

<223> OTHER INFORMATION: SARS reconstituted RBM

<400> SEQUENCE: 93

```
Ser Thr Gly Asn Tyr Asn Tyr Lys Tyr Arg Leu Gly Asp Pro Met Phe
1               5                   10                  15

Ser Pro Asp Gly Lys Pro Cys Thr Pro Cys Thr Pro Pro Ala Leu Asn
            20                  25                  30

Cys Tyr Trp Pro Leu Asn Asp Tyr Gly Phe Tyr Thr Thr
        35                  40                  45
```

<210> SEQ ID NO 94
<211> LENGTH: 45
<212> TYPE: PRT
<213> ORGANISM: Artificial Sequence
<220> FEATURE:
<223> OTHER INFORMATION: SARS reconstituted RBM

<400> SEQUENCE: 94

```
Ser Thr Gly Asn Tyr Asn Tyr Lys Tyr Arg Leu Gly Asp Pro Asn Phe
1               5                   10                  15

Ser Pro Asp Gly Lys Pro Cys Thr Pro Cys Thr Pro Pro Ala Leu Asn
            20                  25                  30

Cys Tyr Trp Pro Leu Asn Asp Tyr Gly Phe Tyr Thr Thr
        35                  40                  45
```

<210> SEQ ID NO 95
<211> LENGTH: 45
<212> TYPE: PRT
<213> ORGANISM: Artificial Sequence
<220> FEATURE:
<223> OTHER INFORMATION: SARS reconstituted RBM

<400> SEQUENCE: 95

```
Ser Thr Gly Asn Tyr Asn Tyr Lys Tyr Arg Leu Gly Glu Val Asp Phe
1               5                   10                  15

Ser Pro Asp Gly Lys Pro Cys Thr Pro Cys Thr Pro Pro Ala Leu Asn
            20                  25                  30

Cys Tyr Trp Pro Leu Asn Asp Tyr Gly Phe Tyr Thr Thr
        35                  40                  45
```

<210> SEQ ID NO 96
<211> LENGTH: 45
<212> TYPE: PRT
<213> ORGANISM: Artificial Sequence
<220> FEATURE:
<223> OTHER INFORMATION: SARS reconstituted RBM

<400> SEQUENCE: 96

```
Ser Thr Gly Asn Tyr Asn Tyr Lys Tyr Arg Leu Gly Glu Pro Leu Phe
1               5                   10                  15

Ser Pro Asp Gly Lys Pro Cys Thr Pro Cys Thr Pro Pro Ala Leu Asn
            20                  25                  30

Cys Tyr Trp Pro Leu Asn Asp Tyr Gly Phe Tyr Thr Thr
        35                  40                  45
```

<210> SEQ ID NO 97
<211> LENGTH: 45
<212> TYPE: PRT
<213> ORGANISM: Artificial Sequence
<220> FEATURE:
<223> OTHER INFORMATION: SARS reconstituted RBM

<400> SEQUENCE: 97

```
Ser Thr Gly Asn Tyr Asn Tyr Lys Tyr Arg Leu Gly Glu Pro Gly Phe
1               5                   10                  15

Ser Pro Asp Gly Lys Pro Cys Thr Pro Cys Thr Pro Pro Ala Leu Asn
            20                  25                  30

Cys Tyr Trp Pro Leu Asn Asp Tyr Gly Phe Tyr Thr Thr
        35                  40                  45


<210> SEQ ID NO 98
<211> LENGTH: 45
<212> TYPE: PRT
<213> ORGANISM: Artificial Sequence
<220> FEATURE:
<223> OTHER INFORMATION: SARS reconstituted RBM

<400> SEQUENCE: 98

Ser Thr Gly Asn Tyr Asn Tyr Lys Tyr Arg Leu Gly Asp Pro Gly Phe
1               5                   10                  15

Ser Pro Asp Gly Lys Pro Cys Thr Pro Cys Thr Pro Pro Ala Leu Asn
            20                  25                  30

Cys Tyr Trp Pro Leu Asn Asp Tyr Gly Phe Tyr Thr Thr
        35                  40                  45


<210> SEQ ID NO 99
<211> LENGTH: 45
<212> TYPE: PRT
<213> ORGANISM: Artificial Sequence
<220> FEATURE:
<223> OTHER INFORMATION: SARS reconstituted RBM

<400> SEQUENCE: 99

Ser Thr Gly Asn Tyr Asn Tyr Lys Tyr Arg Leu Gly Glu Pro Met Phe
1               5                   10                  15

Ser Pro Asp Gly Lys Pro Cys Thr Pro Cys Thr Pro Pro Ala Leu Asn
            20                  25                  30

Cys Tyr Trp Pro Leu Asn Asp Tyr Gly Phe Tyr Thr Thr
        35                  40                  45


<210> SEQ ID NO 100
<211> LENGTH: 44
<212> TYPE: PRT
<213> ORGANISM: Artificial Sequence
<220> FEATURE:
<223> OTHER INFORMATION: SARS reconstituted RBM, K465I

<400> SEQUENCE: 100

Ser Thr Gly Asn Tyr Asn Tyr Lys Tyr Arg Leu Gly Glu Met Phe Ser
1               5                   10                  15

Pro Asp Gly Ile Pro Cys Thr Pro Cys Thr Pro Pro Ala Leu Asn Cys
            20                  25                  30

Tyr Trp Pro Leu Asn Asp Tyr Gly Phe Tyr Thr Thr
        35                  40


<210> SEQ ID NO 101
<211> LENGTH: 44
<212> TYPE: PRT
<213> ORGANISM: Artificial Sequence
<220> FEATURE:
<223> OTHER INFORMATION: SARS reconstituted RBM, K465I

<400> SEQUENCE: 101

Ser Thr Gly Asn Tyr Asn Tyr Lys Tyr Arg Leu Glu Glu Pro Phe Ser
1               5                   10                  15
```

Pro Asp Gly Ile Pro Cys Thr Pro Cys Thr Pro Pro Ala Leu Asn Cys
20 25 30

Tyr Trp Pro Leu Asn Asp Tyr Gly Phe Tyr Thr Thr
35 40

<210> SEQ ID NO 102
<211> LENGTH: 44
<212> TYPE: PRT
<213> ORGANISM: Artificial Sequence
<220> FEATURE:
<223> OTHER INFORMATION: SARS reconstituted RBM, K465I STGNYNYKYRL GEE

<400> SEQUENCE: 102

Ser Thr Gly Asn Tyr Asn Tyr Lys Tyr Arg Leu Gly Glu Glu Phe Ser
1 5 10 15

Pro Asp Gly Ile Pro Cys Thr Pro Cys Thr Pro Pro Ala Leu Asn Cys
20 25 30

Tyr Trp Pro Leu Asn Asp Tyr Gly Phe Tyr Thr Thr
35 40

<210> SEQ ID NO 103
<211> LENGTH: 44
<212> TYPE: PRT
<213> ORGANISM: Artificial Sequence
<220> FEATURE:
<223> OTHER INFORMATION: SARS reconstituted RBM, K465I

<400> SEQUENCE: 103

Ser Thr Gly Asn Tyr Asn Tyr Lys Tyr Arg Leu Gly Glu Asn Phe Ser
1 5 10 15

Pro Asp Gly Ile Pro Cys Thr Pro Cys Thr Pro Pro Ala Leu Asn Cys
20 25 30

Tyr Trp Pro Leu Asn Asp Tyr Gly Phe Tyr Thr Thr
35 40

<210> SEQ ID NO 104
<211> LENGTH: 45
<212> TYPE: PRT
<213> ORGANISM: Artificial Sequence
<220> FEATURE:
<223> OTHER INFORMATION: SARS reconstituted RBM, K465I

<400> SEQUENCE: 104

Ser Thr Gly Asn Tyr Asn Tyr Lys Tyr Arg Leu Gly Asp Pro Met Phe
1 5 10 15

Ser Pro Asp Gly Ile Pro Cys Thr Pro Cys Thr Pro Pro Ala Leu Asn
20 25 30

Cys Tyr Trp Pro Leu Asn Asp Tyr Gly Phe Tyr Thr Thr
35 40 45

<210> SEQ ID NO 105
<211> LENGTH: 45
<212> TYPE: PRT
<213> ORGANISM: Artificial Sequence
<220> FEATURE:
<223> OTHER INFORMATION: SARS reconstituted RBM, K465I

<400> SEQUENCE: 105

Ser Thr Gly Asn Tyr Asn Tyr Lys Tyr Arg Leu Gly Asp Pro Asn Phe
1 5 10 15

Ser Pro Asp Gly Ile Pro Cys Thr Pro Cys Thr Pro Pro Ala Leu Asn
20 25 30

```
Cys Tyr Trp Pro Leu Asn Asp Tyr Gly Phe Tyr Thr Thr
        35                  40                  45


<210> SEQ ID NO 106
<211> LENGTH: 45
<212> TYPE: PRT
<213> ORGANISM: Artificial Sequence
<220> FEATURE:
<223> OTHER INFORMATION: SARS reconstituted RBM, K465I

<400> SEQUENCE: 106

Ser Thr Gly Asn Tyr Asn Tyr Lys Tyr Arg Leu Gly Glu Val Asp Phe
1               5                   10                  15

Ser Pro Asp Gly Ile Pro Cys Thr Pro Cys Thr Pro Pro Ala Leu Asn
            20                  25                  30

Cys Tyr Trp Pro Leu Asn Asp Tyr Gly Phe Tyr Thr Thr
        35                  40                  45


<210> SEQ ID NO 107
<211> LENGTH: 45
<212> TYPE: PRT
<213> ORGANISM: Artificial Sequence
<220> FEATURE:
<223> OTHER INFORMATION: SARS reconstituted RBM, K465I

<400> SEQUENCE: 107

Ser Thr Gly Asn Tyr Asn Tyr Lys Tyr Arg Leu Gly Glu Pro Leu Phe
1               5                   10                  15

Ser Pro Asp Gly Ile Pro Cys Thr Pro Cys Thr Pro Pro Ala Leu Asn
            20                  25                  30

Cys Tyr Trp Pro Leu Asn Asp Tyr Gly Phe Tyr Thr Thr
        35                  40                  45


<210> SEQ ID NO 108
<211> LENGTH: 45
<212> TYPE: PRT
<213> ORGANISM: Artificial Sequence
<220> FEATURE:
<223> OTHER INFORMATION: SARS reconstituted RBM, K465I

<400> SEQUENCE: 108

Ser Thr Gly Asn Tyr Asn Tyr Lys Tyr Arg Leu Gly Glu Pro Gly Phe
1               5                   10                  15

Ser Pro Asp Gly Ile Pro Cys Thr Pro Cys Thr Pro Pro Ala Leu Asn
            20                  25                  30

Cys Tyr Trp Pro Leu Asn Asp Tyr Gly Phe Tyr Thr Thr
        35                  40                  45


<210> SEQ ID NO 109
<211> LENGTH: 45
<212> TYPE: PRT
<213> ORGANISM: Artificial Sequence
<220> FEATURE:
<223> OTHER INFORMATION: SARS reconstituted RBM, K465I

<400> SEQUENCE: 109

Ser Thr Gly Asn Tyr Asn Tyr Lys Tyr Arg Leu Gly Asp Pro Gly Phe
1               5                   10                  15

Ser Pro Asp Gly Ile Pro Cys Thr Pro Cys Thr Pro Pro Ala Leu Asn
            20                  25                  30

Cys Tyr Trp Pro Leu Asn Asp Tyr Gly Phe Tyr Thr Thr
        35                  40                  45
```

-continued

```
<210> SEQ ID NO 110
<211> LENGTH: 45
<212> TYPE: PRT
<213> ORGANISM: Artificial Sequence
<220> FEATURE:
<223> OTHER INFORMATION: SARS reconstituted RBM, K465I

<400> SEQUENCE: 110

Ser Thr Gly Asn Tyr Asn Tyr Lys Tyr Arg Leu Gly Glu Pro Met Phe
1               5                   10                  15

Ser Pro Asp Gly Ile Pro Cys Thr Pro Cys Thr Pro Pro Ala Leu Asn
            20                  25                  30

Cys Tyr Trp Pro Leu Asn Asp Tyr Gly Phe Tyr Thr Thr
        35                  40                  45
```